US008771714B2

(12) United States Patent
Spinale et al.

(10) Patent No.: US 8,771,714 B2
(45) Date of Patent: Jul. 8, 2014

(54) SYSTEMS AND METHODS FOR IN VIVO MEASUREMENT OF INTERSTITIAL BIOLOGICAL ACTIVITY, PROCESSES AND/OR COMPOSITIONS

(75) Inventors: Francis G. Spinale, Charleston, SC (US); Robert Stroud, Mount Pleasant, SC (US); Michael Looper, Mount Pleasant, SC (US); Anne Deschamps, Mount Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 1250 days.

(21) Appl. No.: 12/513,116

(22) PCT Filed: Oct. 31, 2007

(86) PCT No.: PCT/US2007/083212
§ 371 (c)(1),
(2), (4) Date: Sep. 22, 2009

(87) PCT Pub. No.: WO2008/055225
PCT Pub. Date: May 8, 2008

(65) Prior Publication Data
US 2010/0016697 A1    Jan. 21, 2010

Related U.S. Application Data

(60) Provisional application No. 60/855,419, filed on Oct. 31, 2006.

(51) Int. Cl.
*A61K 9/00* (2006.01)
*A61B 5/0275* (2006.01)
*C12Q 1/34* (2006.01)
*C12Q 1/37* (2006.01)
*C12Q 1/06* (2006.01)
*G01N 33/574* (2006.01)
*G01N 33/573* (2006.01)
*G01N 33/00* (2006.01)
*A61K 51/00* (2006.01)

(52) U.S. Cl.
USPC ......... 424/400; 600/342; 435/7.22; 435/7.93; 435/18; 435/24; 435/39

(58) Field of Classification Search
USPC .............. 424/400; 435/7.22, 7.93, 22, 24, 39; 600/342
See application file for complete search history.

(56) References Cited

U.S. PATENT DOCUMENTS

| 4,409,140 A * | 10/1983 | Smith et al. ............... 530/330 |
| 7,132,249 B1 * | 11/2006 | Salter et al. ............... 435/8 |
| 2004/0166554 A1 | 8/2004 | Chamoles |
| 2006/0205671 A1 * | 9/2006 | Vinten-Johansen ............ 514/18 |

OTHER PUBLICATIONS

Deschamps et al. 2005a. Trafficking of the Membrane Type-1 Matrix Metalloproteinase in Ischemia and Reperfusion: Relation to Interstitial Membrane Type-1 Matrix Metalloproteinase Activity. Circulation, vol. 111, pp. 1166-1174.*
Tomaselli et al. 1999. Electro-physiological remodeling in hypertrophy and heart failure. Cardiovascular Research, vol. 42, pp. 270-283.*
Deschamps et al. 2005b. Myocardial Interstitial Matrix Metalloproteinase Activity is Altered by Mechanical Changes in LV Load Interaction With the Angiotensin Type 1 Receptor. Circulation Research, vol. 96, pp. 1110-1118.*
Ahmed, et al., "Matrix metalloproteinases / tissue inhibitors of metalloproteinases: relationship between changes in proteolytic determinants of matrix composition and structural, functional & clinical manifestations of hypertensive heart disease", Circulation, 113(17):2089-96 (2006).
Bonnema, et al., "Effects of age on plasma matrix metalloproteinases (MMPs) and tissue inhibitors of metalloproteinases (TIMPs)", J Card Fail., 13(7):530-40 (2007).
Deschamps, et al., "Interruption of endothelin signaling modifies membrane type-1 matrix metalloproteinase activity during ischemia and reperfusion", Am J Physiol, 294(2):H875-83 (2008).
Dixon, et al., "Heterogeneity in MT1-MMP activity with ischemia-reperfusion and previous myocardial infarction: relation to regional myocardial function", Am J Physiol, 299(6):H1947-58 (2010).
Dorman, et al., "Differential effects of epsilon-aminocaproic acid and aprotinin on matrix metalloproteinase release in patients following cardiopulmonary bypass", J Cardiovasc Pharmacol., 51(4):418-23 (2008).
Hsia, et al., "Determinants of extracellular matrix remodeling are differentially expressed in pediatric and adult dilated cardiomyopathy", Eur J Heart Fail., 13(3):271-7 (2010).
Hsia, et al., "Effects of aprotinin or tranexamic acid on proteolytic / cytokine profiles in infants following cardiac surgery", Ann Thorac Surg, 89(6):1843-52 (2010).
Hsia, et al., "Plasma profiling determinants of matrix homeostasis in pediatric dilated cardiomyopathy", Cardiol Young, 27:1-10 (2010).
McEvoy, et al., "Aprotinin modifies left ventricular contractility and cytokine release following ischemia-reperfusion in a dose-dependent manner in a murine model", Anesth Analg. 108(2):399-406 (2009).
McEvoy, et al., "Aprotinin exerts differential and dose dependent effects on myocardial contractility, oxidative stress and cytokine release after ischemia-reperfusion". Ann Thorac Surg, 86(2):568-75 (2008).
McQuinn, et al., "Circulating matrix metalloproteinase levels after ventricular septal defect repair in infants", J Thorac Cardiovasc Surg., 140(6): 1257-65 (2010).
Mukherjee, et al., "Cardiac function and circulating cytokines following endotoxin exposure in neonatal mice", Pediatr Res., 68(5):381-6 (2010).
Pearson, et al., "Automated enzyme assays by use of a centrifugal analyzer with fluorescence detection", Clinical Chem., 27(2):256-62 (1981).
Reust, et al., "Continuous localized monitoring of plasmin activity identifies differential and regional effects of the serine protease inhibitor aprotinin: relevance to antifibrinolytic therapy", J Cardiov Pharm.,57(4):400-6 (2011).
Reust, et al., "Temporally and regionally disparate differences in plasmin activity by tranexamic acid", Anesth Analg, 110(3):694-701 (2010).
Reust et al., "Interstitial plasmin activity with epsilon-aminocaproic acid: temporal and regional heterogeneity", Ann Thorac Surg, 89(5):1538-45 (2010).

(Continued)

*Primary Examiner* — Jon P Weber
*Assistant Examiner* — Kailash C Srivastava
(74) *Attorney, Agent, or Firm* — Meunier Carlin & Curfman LLC

(57) ABSTRACT

Provided are systems and methods for detecting and/or measuring in vivo interstitial biological activity, processes, and or compounds in human or animal subjects.

29 Claims, 28 Drawing Sheets

(56) References Cited

OTHER PUBLICATIONS

Sabbagh, et al., "Aprotinin exacerbates LV dysfunction after ischemia-reperfusion in mice lacking tumor necrosis factor receptor I", J Card Pharm. 52(4):355-62 (2008).

Shah, et al., "Differential matrix metalloproteinase levels in adenocarcinoma and sqamous cell carcinoma of the lung", J Thorac Cardiovasc Surg, 139(4):984-90 (2010).

Spinale, et al., "Cardiac restricted over-expression of membrane type-1 matrix metalloproteinase causes adverse myocardial remodeling following myocardial infarction", J Bio Chem., 24;285(39):30316-27 (2010).

Spinale, et al., "Dynamic changes in matrix metalloproteinase activity within the human myocardial interstitium during ischemia reperfusion", Circulation, 30;118;S16-23 (2008).

Webb, et al., "Specific temporal profile of matrix metalloproteinase release occurs in patients following myocardial infarcion: relation to left ventricular remodeling", Circulation 5; 114(10);1020-7 (2006).

Yan, et al., "Plasma matrix metalloproteinase-9 level is correlated with left ventricular volumes and ejection fraction in patients with heart failure", J Card Fail, 12(7):514-9(2006).

Yan, et al., "Relationship between plasma levels of matrix metalloproteinase and neurohormonal profile in patients with heart failure", Eur, J Heart Fail., 10(2):125-8 (2008).

Zile, et al., Plasma biomarkers that reflect determinants of matrix composition identify the presence of left ventricular hypertrophy and diastolic heart failure. Circulation Heart Fail, 1;4(3):246-56 (2011).

\* cited by examiner

SEQUENCE LISTING

```
<160> NUMBER OF SEQ ID NOS: 11

<210> SEQ ID NO 1
<211> LENGTH: 7
<212> TYPE: PRT
<213> ORGANISM: Artificial Sequence
<220> FEATURE:
<221> NAME/KEY: MOD_RES
<222> LOCATION: 1
<223> OTHER INFORMATION: Pro is bound by DNP moiety 2,4-Dinitrophenyl
<220> FEATURE:
<221> NAME/KEY: MOD_RES
<222> LOCATION: 7
```

```
<223> OTHER INFORMATION: Arg in the D configuration
<220> FEATURE:
<221> NAME/KEY: AMIDATION
<222> LOCATION: 7
<220> FEATURE:
<223> OTHER INFORMATION: Description of Artificial Sequences; note =
      synthetic construct

<400> SEQUENCE: 1

Pro Leu Gly Leu Trp Ala Arg
 1               5

<210> SEQ ID NO 2
<211> LENGTH: 13
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa=Abu and is preceded and bound by DABCYL
      moiety 4-(4'-dimethylaminophenylazo) benzoic acid
<220> FEATURE:
<221> NAME/KEY: MOD_RES
<222> LOCATION: 8
<223> OTHER INFORMATION: Nva
<220> FEATURE:
<221> NAME/KEY: MOD_RES
<222> LOCATION: 11
<223> OTHER INFORMATION: Glu is modified with EDANS moiety
      5-(2'aminoethyl)aminonaphthalene-1-sulfonic acid
<220> FEATURE:
<221> NAME/KEY: AMIDATION
<222> LOCATION: 13
<220> FEATURE:
<223> OTHER INFORMATION: Description of Artificial Sequences; note =
      synthetic construct

<400> SEQUENCE: 2

Xaa Arg Pro Leu Pro Val Glu Val Trp Arg Glu Ala Lys
 1               5                  10

<210> SEQ ID NO 3
<211> LENGTH: 6
<212> TYPE: PRT
<213> ORGANISM: Artificial Sequence
<220> FEATURE:
<221> NAME/KEY: MOD_RES
<222> LOCATION: 1
<223> OTHER INFORMATION: Pro is bound by DNP moiety 2,4-Dinitrophenyl
<220> FEATURE:
<221> NAME/KEY: MOD_RES
<222> LOCATION: 6
<223> OTHER INFORMATION: Arg is modified with a hydroxyl group
<220> FEATURE:
<223> OTHER INFORMATION: Description of Artificial Sequences; note =
      synthetic construct

<400> SEQUENCE: 3

Pro Leu Ala Leu Trp Arg
 1               5

<210> SEQ ID NO 4
<211> LENGTH: 7
<212> TYPE: PRT
<213> ORGANISM: Artificial Sequence
<220> FEATURE:
<221> NAME/KEY: MOD_RES
<222> LOCATION: 1
<223> OTHER INFORMATION: Pro is bound by DNP moiety 2,4-Dinitrophenyl
<220> FEATURE:
<221> NAME/KEY: MOD_RES
<222> LOCATION: 7
<223> OTHER INFORMATION: Arg is modified with a hydroxyl group
```

-continued

```
<220> FEATURE:
<223> OTHER INFORMATION: Description of Artificial Sequences; note =
      synthetic construct

<400> SEQUENCE: 4

Pro Tyr Ala Tyr Trp Met Arg
1               5

<210> SEQ ID NO 5
<211> LENGTH: 8
<212> TYPE: PRT
<213> ORGANISM: Artificial Sequence
<220> FEATURE:
<221> NAME/KEY: MOD_RES
<222> LOCATION: 1
<223> OTHER INFORMATION: Arg is bound by DNP moiety 2,4-Dinitrophenyl
<220> FEATURE:
<221> NAME/KEY: MOD_RES
<222> LOCATION: 8
<223> OTHER INFORMATION: Ser is modified with a hydroxyl group
<220> FEATURE:
<223> OTHER INFORMATION: Description of Artificial Sequences; note =
      synthetic construct

<400> SEQUENCE: 5

Arg Pro Leu Ala Leu Trp Arg Ser
1               5

<210> SEQ ID NO 6
<211> LENGTH: 7
<212> TYPE: PRT
<213> ORGANISM: Artificial Sequence
<220> FEATURE:
<221> NAME/KEY: MOD_RES
<222> LOCATION: 1
<223> OTHER INFORMATION: Pro is bound by DNP moiety 2,4-Dinitrophenyl
<220> FEATURE:
<221> NAME/KEY: MOD_RES
<222> LOCATION: 7
<223> OTHER INFORMATION: Arg is modified with a hydroxyl group
<220> FEATURE:
<223> OTHER INFORMATION: Description of Artificial Sequences; note =
      synthetic construct

<400> SEQUENCE: 6

Pro Leu Ala Tyr Trp Ala Arg
1               5

<210> SEQ ID NO 7
<211> LENGTH: 6
<212> TYPE: PRT
<213> ORGANISM: Artificial Sequence
<220> FEATURE:
<221> NAME/KEY: MOD_RES
<222> LOCATION: 1
<223> OTHER INFORMATION: Pro is bound by MCA moiety
      (7-methoxycoumarin-4-yl)acetyl
<220> FEATURE:
<221> NAME/KEY: VARIANT
<222> LOCATION: 2
<223> OTHER INFORMATION: Xaa = Cha
<220> FEATURE:
<221> NAME/KEY: MOD_RES
<222> LOCATION: 4
<223> OTHER INFORMATION: Nva
<220> FEATURE:
<221> NAME/KEY: MOD_RES
<222> LOCATION: 6
<223> OTHER INFORMATION: Ala is bound by DPA moiety
      3-(2,4-dinitrophenyl)-L-2,3-diaminopropionyl
<220> FEATURE:
<223> OTHER INFORMATION: Description of Artificial Sequences; note =
      synthetic construct
```

```
<220> FEATURE:
<221> NAME/KEY: AMIDATION
<222> LOCATION: 6

<400> SEQUENCE: 7

Pro Xaa Gly Val His Ala
 1               5

<210> SEQ ID NO 8
<211> LENGTH: 7
<212> TYPE: PRT
<213> ORGANISM: Artificial Sequence
<220> FEATURE:
<221> NAME/KEY: MOD_RES
<222> LOCATION: 1
<223> OTHER INFORMATION: Pro is bound by moiety MCA =
      (7-methoxycoumarin-4-yl)acetyl
<220> FEATURE:
<221> NAME/KEY: MOD_RES
<222> LOCATION: 4
<223> OTHER INFORMATION: Cys is bound by p-OmeBz moiety(
      S-para-methoxybenzyl)
<220> FEATURE:
<221> NAME/KEY: MOD_RES
<222> LOCATION: 7
<223> OTHER INFORMATION: Arg is bound by Dpa  moiety
      3-(2,4-dinitrophenyl)-L-2,3-diaminopropionyl
<220> FEATURE:
<221> NAME/KEY: AMIDATION
<222> LOCATION: 7
<220> FEATURE:
<223> OTHER INFORMATION: Description of Artificial Sequences; note =
      synthetic construct

<400> SEQUENCE: 8

Pro Leu Ala Cys Trp Ala Arg
 1               5

<210> SEQ ID NO 9
<211> LENGTH: 7
<212> TYPE: PRT
<213> ORGANISM: Artificial Sequence
<220> FEATURE:
<221> NAME/KEY: MOD_RES
<222> LOCATION: 1
<223> OTHER INFORMATION: Pro is bound by DNP moiety 2,4-Dinitrophenyl
<220> FEATURE:
<221> NAME/KEY: MOD_RES
<222> LOCATION: 7
<223> OTHER INFORMATION: Arg is modified with a hydroxyl group
<220> FEATURE:
<223> OTHER INFORMATION: Description of Artificial Sequences; note =
      synthetic construct

<400> SEQUENCE: 9

Pro Leu Gly Met Trp Ser Arg
 1               5

<210> SEQ ID NO 10
<211> LENGTH: 6
<212> TYPE: PRT
<213> ORGANISM: Artificial Sequence
<220> FEATURE:
<221> NAME/KEY: MOD_RES
<222> LOCATION: 1
<223> OTHER INFORMATION: Ala is bound to and preceded by an energy
      acceptor moiety (X)
<220> FEATURE:
<221> NAME/KEY: MOD_RES
<222> LOCATION: 4
<223> OTHER INFORMATION: Asn is bound by subsequent hydrophobic residue
      (Y)
<220> FEATURE:
```

```
<221> NAME/KEY: VARIANT
<222> LOCATION: 5
<223> OTHER INFORMATION: Xaa = Lys or Arg
<220> FEATURE:
<223> OTHER INFORMATION: Description of Artificial Sequences; note =
      synthetic construct
<220> FEATURE:
<221> NAME/KEY: MOD_RES
<222> LOCATION: 6
<223> OTHER INFORMATION: Asp is bound by a subsequent energy donor
      moiety capable of emitting energy (Z)

<400> SEQUENCE: 10

Ala Gly Glu Asn Xaa Asp
 1               5

<210> SEQ ID NO 11
<211> LENGTH: 3
<212> TYPE: PRT
<213> ORGANISM: Artificial Sequence
<220> FEATURE:
<221> NAME/KEY: MOD_RES
<222> LOCATION: 3
<223> OTHER INFORMATION: Lys is bound to a subsequent fluorophore
<220> FEATURE:
<223> OTHER INFORMATION: Description of Artificial Sequences; note =
      synthetic construct

<400> SEQUENCE: 11

Ala Leu Lys
 1
```

SYSTEMS AND METHODS FOR IN VIVO MEASUREMENT OF INTERSTITIAL BIOLOGICAL ACTIVITY, PROCESSES AND/OR COMPOSITIONS

CROSS REFERENCE TO RELATED APPLICATIONS

This application claims the benefit of U.S. Provisional Application No. 60/855,419, filed Oct. 31, 2006, which is hereby incorporated by reference in its entirety.

ACKNOWLEDGEMENTS

This invention was made with government support under 5R01 HL059165-07, 2P01 HL048788-11 and 1R01 HL56603 awarded by the National Institutes of Health. The government has certain rights in the invention.

BACKGROUND OF THE INVENTION

The primary approaches currently used for measuring in vivo interstitial biological activity, processes, and/or compounds in human or animal subjects require collection of interstitial fluid samples followed by measurement using in vitro assay systems. These approaches generally do not allow for comprehensive detection or measurement of interstitial biological activity, processes, and/or compounds since endogenous regulatory mechanisms are removed. Moreover, such in vitro assay systems do not allow for real-time monitoring or continuous monitoring of interstitial fluid processes in normal or disease states.

SUMMARY

In accordance with the purposes of this invention, as embodied and broadly described herein, this invention, in one aspect, relates to systems and methods for in vivo detection and/or measurement of interstitial biological activity, processes, and or compounds in human or animal subjects.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several aspects of the invention and together with the description, serve to explain the principles of the invention.

(FIG. 15, top). FIG. 15 also shows results of incubation of full length MT1-MMP (pretreated with 10 μM p-aminophenylmercuric acetate) for 1 hour at 37° C. with or without an antibody specific for the catalytic domain of MT1-MMP (1000 ng/mL, Chemicon AB8102). After the incubation period, the MT1-MMP substrate was injected and fluorescence emission recorded. (FIG. 15, bottom).

FIG. 16, top), MMP-8 (10 ng/mL, Calbiochem; FIG. 16, middle), or a disintegrin and metalloproteinase (ADAM)-10 and -17 cocktail (200 ng/mL, R&D Systems; FIG. 16, bottom).

DETAILED DESCRIPTION OF THE INVENTION

Figure 1:
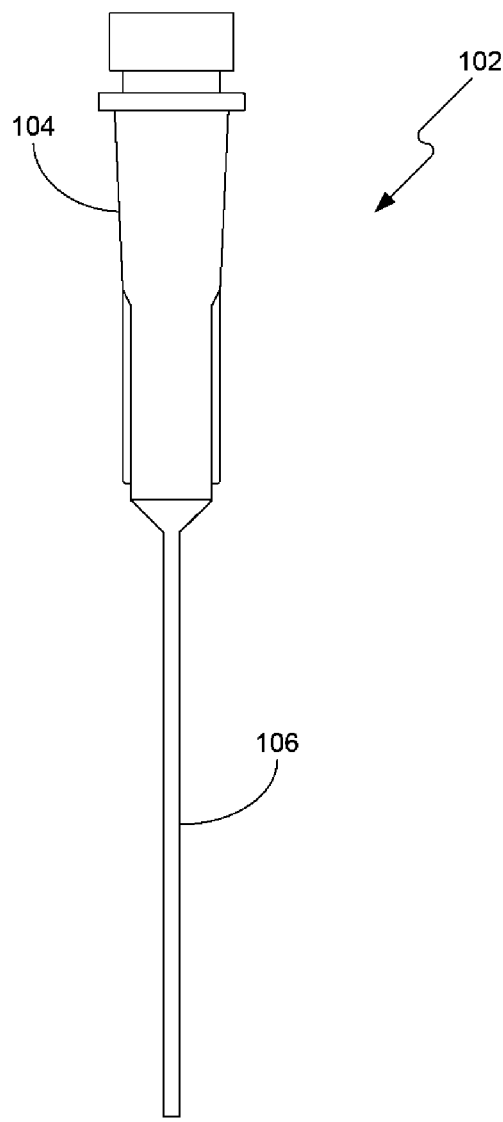
FIG. 1 is an exemplary introducer device for use with systems and methods of the present invention, according to one aspect.

The present invention may be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to a "substrate" can include two or more such substrates unless the context indicates otherwise. Similarly, reference to a "compound" can include two or more such compounds unless the context indicates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

By a "subject" is meant an individual. The term subject includes small or laboratory animals as well as primates, including humans. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included. The term "patient" includes human and veterinary patients.

Reference will now be made in detail to the present preferred aspects of the invention, examples of which are illustrated in the accompanying drawings. Wherever possible, the same reference numbers are used throughout the drawings to refer to the same or like parts.

Provided herein are systems and methods for in vivo detection and/or measurement of interstitial biological activity, processes, and/or compounds in human or animal subjects. The term "in vivo" means that which takes place inside an organism. It will be appreciated by one skilled in the art that that portions of the systems and methods of the present invention occur ex vivo.

An exemplary system of the present invention can include a substrate designed to interact with compounds in the subject's interstitium. For example, at least one fluorogenic substrate can be configured to interact with a compound of interest located within the interstitial fluid of a subject. Compounds of interest can be determined by one of skill in the art. For example, a given compound of interest can be determined based on the desired interstitial biological activity, process and/or compound to be monitored in the subject.

Depending on the compound of interest, a substrate can be designed and made that can interact with the compound of interest. For example, since the exemplary systems and methods as described herein can be used to monitor an in vivo biological process, the biological system to be measured can be identified. Such a biological system can include, but are not limited to, an enzyme system, a biological pathway or a structural protein. For example, in various degenerative diseases, as the degeneration increases, a greater number of specific proteins are released. Exemplary systems can be used to measure those proteins.

Once the desired biological process, activity and/or compound to be detected or measured is determined, one or more protein or target of the system of interest can be sequenced. The amino acid sequence for the particular protein can then be identified. A smaller sequence of amino acids that interacts with the protein can also be identified. For example, this latter sequence can be one that binds to the protein of interest. Optionally, the sequence can be processed by the protein of interest. Thus, it is contemplated that an amino acid sequence can be identified that would be recognized uniquely by the protein or system that is desired to be measured.

The amino acid sequence can then be linked to a fluorogenic moiety or other detectable moiety, which can become fluorescent or otherwise detectable once the target amino acid sequence is bound or recognized by the protein or system of interest.

In one exemplary aspect, the methods and systems of the present invention use one or more fluorogenic peptide substrates that exhibit intermolecular quenching. In these substrates, the peptide sequence separates a fluorescent donor group from an acceptor group that acts as a quencher of fluorescence. This phenomenon, in which excitation energy is transferred from an excited fluorescent donor to a quenching acceptor, is called resonance energy transfer. Cleavage of a peptide bond within the substrate leads to the separation of the donor-acceptor pair from the same molecule, thus allowing the increase of the fluorescence. The fluorescence increase is substantially proportional to the amount of peptide hydrolyzed. Some exemplary quenched fluorogenic substrates and concepts related to quenched fluorogenic substrates are described below.

In vitro experimental measurements can then be made to determine whether the fluorogenic moiety modifies the natural behavior and binding characteristics of the amino acid sequence. Thus, the process can be iterative to determine a combination of amino acid structures and fluorogenic moieties to obtain a sequence with a fluorogenic substrate tagged to it that would specifically bind to the protein or be reacted by the system of interest.

Once the particular combination is determined, in vitro testing can be performed to react the fluorogenic amino acid sequence in the biological system of interest in a well-confined and controlled environment, such as in, for example, a multi-well plate or spectrophotometer. Calibration standards can be developed to determine the amount of fluorescent signal that will be generated during the reaction. This process can again be iterated until a fluorogenic amino acid is found that has a linear reaction with the biological system or can be modeled with a mathematical equation that can allow the reaction to be calibrated and standardized.

Further in vitro tests can be performed by loading the fluorogenic compound into a described system. An interstitial probe, such as described herein, can be placed into target tissue or the site of interest with the targeted amino acid sequence that has the fluorogenic moiety. Steady state measurements can be taken in vitro that will directly relate the fluorogenic activity of the amino acid to the biological system itself.

It is contemplated that, in one aspect, an amino acid structure can be developed that binds to a unique protein and the fluorescence is diminished inversely to the amount of protein present in the tissue, without specifically having a catalytic or enzymatic reaction. In the case of a non-catalytic reaction, a fluorogenic moiety can be infused directly into the biological system of interest and the fluorescent signal, which would be inversely proportional to the amount of protein or substance of interest in the tissue, can be measured.

To detect the substrate, for example a fluorogenic substrate, the exemplary systems of the present invention can further comprise a detector apparatus having a substrate receptacle, an energy source and a detector element, wherein the substrate receptacle is in fluid communication with interstitial fluid comprising the substrate and is configured to accept interstitial fluid comprising the substrate.

The exemplary systems of the present invention can further comprise means for positioning the substrate receptacle, energy source and detector element within the detector apparatus such that energy generated by the energy source can be directed into the substrate receptacle to excite the accepted substrate and such that the excited substrate can be detected by the detector element.

The methods and systems of the present invention provide a reliable way to interrogate the interstitium and can provide a relative index of enzyme activity and/or composition presence within the interstitial space in vivo. The systems and methods can be used to determine the in vivo presence and/or activity and/or quantity of one or more interstitial composition or compound. For example, the presence and/or activity and/or quantity of one or more interstitial enzyme can be determined. Enzyme activities that can be monitored include, but are not limited to, MMP activity and protease activity.

Thus, the systems and methods of the present invention can allow for real-time measurement of interstitial compounds. In one aspect, the systems and methods can be used to measure matrix metalloproteinase (MMP) activity in a subject. MMP activity can be measured in normal or disease states including, without limitation, ischemia reperfusion, hypertrophy, and heart failure. In other aspects, a substrate can be designed for any proteolytic enzyme. Proteolytic enzymes are known to those skilled in the art. For example, substrates can be designed for the proteolytic enzymes described or disclosed by Alan Barrett et al., in "Handbook of Proteolytic Enzymes," Academic Press, 1998. The designed substrates can be specific for a given enzyme, process, activity or compound of interest. Also, one or more substrate can be used wherein each substrate is specific for a distinct enzyme, process, activity or compound of interest.

Moreover, the systems and methods of the present invention are not limited to interrogating cardiac interstitium or to detecting and/or monitoring MMP activity. Any interstitial fluid located in any organ system or portion thereof can be interrogated. For example, in some exemplary aspects, the systems and methods can be used to interrogate the interstitial fluid of muscle, skin, liver, uterus, kidney, joints, and the like. Further, it is contemplated that any compound located at least partially in the interstitial fluid can be detected and monitored. In one aspect, such compounds can be endogenous or exogenous. In another aspect, the activity of one or more enzymes can be detected or monitored using the systems and methods of the present invention.

Thus, the systems and methods of the present invention can be used to detect and monitor compositions and enzymes in any interstitial space located in any anatomic location in a subject. In regard to MMP activity, some exemplary indications include, without limitation: measuring MMP activity in cardiovascular disease; in cancer to help define the aggressive potential of the cancer; in rheumatology and inflammation to help define the nature of the inflammatory process and specific local levels of MMP activity.

The systems and methods of the present invention can be used to dynamically measure an interstitial compound, activity and/or process of interest. For example, a compound, activity and/or process can be measured continuously or in real-time. Thus, trends or changes in compounds, activities, and/or processes can be monitored over time. In these aspects, the detection systems described herein can include a processor system configured to monitor detected substrate over time.

The methods and systems of the present invention are also valuable in drug discovery and pharmacology. For example, the systems and methods of the present invention can provide a rapid means to determine drug efficacy. In one aspect, interstitial MMP or other enzyme activity can be measured before, during and/or after administration of a drug to a subject. The measured MMP activity can be used to assess activity of the administered drug in the subject.

In one aspect, a detection system comprises at least one substrate having a first state that can be altered by enzymatic activity within a subject's interstitial fluid to a second detectable state. The detection system also has a detector apparatus having a substrate receptacle, energy source and a detector element. The substrate receptacle can be in fluid communication with the at least one substrate in its detectable state. The detection system can also have means for positioning the substrate receptacle, energy source and detector element within the detector apparatus such that energy generated by the energy source can be directed into the substrate receptacle to excite the detectable substrate. In this aspect, the excited detectable substrate can be detected by the detector element.

In a further aspect, the detection system can comprise a probe configured for selective positioning within interstitial fluid of the subject. The probe can be configured to deliver the at least one substrate in the first state into the interstitial fluid of the subject and can be further configured to receive interstitial fluid having the at least one substrate in the second detectable state from the subject.

According to another aspect, a detection system is provided that comprises at least one fluorogenic substrate configured to interact with a compound of interest located within the interstitial fluid of a subject.

Fluorophores are compounds or molecules that luminescence. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO—TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis—BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFPNYFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD—Lipophilic Tracer; DiD (DilC18(5)); DIDS; Dihydrorhodamine 123 (DHR); Dil (DilC18(3)); 1Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP(S65T); GFP red shifted (rs-GFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/ Ethidium homodimer; LOLO-1; LO-PRO-i; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium lodid (Pl); PYMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline); Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22;

SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

The substrates can comprise a polypeptide. In one aspect, a polypeptide is provided that comprises the sequence X'-Ala-Gly-Glu-Asn-Y'-Lys/Arg-Asp-Z' (SEQ ID NO:10). Z' is an energy donor moiety that is capable of emitting energy, X' is an energy acceptor moiety that is capable of absorbing an amount of the emitted energy, and Y' is a hydrophobic residue. The acceptor moiety absorbs the amount of the emitted energy. According to yet another aspect, a polypeptide is provided that comprises the sequence Ala-Leu-Lys-V'(SEQ ID NO:11), where V' is a fluorophore. In one aspect, the polypeptide emits energy only if it remains intact. In another aspect, the polypeptide can cease to emit energy once the bond between the Lys and V' moiety is cleaved.

Sequence Similarities

Homologs of the present peptides are provided. It is understood that as discussed herein the use of the terms homology and identity mean the same thing as similarity. Thus, for example, if the word homology is used between two non-natural sequences it is understood that this is not necessarily indicating an evolutionary relationship between these two sequences, but rather is looking at the similarity or relatedness between their sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or polypeptides. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman, *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al., *Proc. Natl. Acad. Sci. USA* 86:7706-7710, 1989, Jaeger et al., *Methods Enzymol.* 183:281-306, 1989, which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Peptides and Proteins

There are numerous variants, modifications or derivatives of the disclosed substrates that disclosed and herein contemplated. Protein or peptide variants and derivatives are well understood to those of skill in the art and in can involve amino acid sequence modifications. For example, amino acid sequence modifications typically fall into one or more of three classes: substitutional, insertional or deletional variants.

Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by crosslinking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues.

Deletions or insertions can be made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure.

Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
| --- | --- |
| alanine | Ala/A |
| isoleucine | Ile/I |
| arginine | Arg/R |
| asparagine | Asn/N |
| aspartic acid | Asp/D |
| cysteine | Cys/C |
| glutamic acid | Glu/E |
| glutamine | Gln/K |
| glycine | Gly/G |
| histidine | His/H |
| isolelucine | Ile/I |
| leucine | Leu/L |
| lysine | Lys/K |
| phenylalanine | Phe/F |
| proline | Pro/P |
| pyroglutamic acidp | Glu/__ |
| serine | Ser/S |
| threonine | Thr/T |
| tyrosine | Tyr/Y |
| tryptophan | Trp/W |
| valine | Val/V |

TABLE 2

Amino Acid Substitutions

| Original Residue | Exemplary Conservative Substitutions, others are known in the art. |
| --- | --- |
| Ala | ser |
| Arg | lys, gln |
| Asn | gln; his |
| Asp | glu |
| Cys | ser |
| Gln | asn, lys |
| Glu | asp |
| Gly | pro |
| His | asn; gln |
| Ile | leu; val |
| Leu | ile; val |
| Lys | arg; gln; |
| Met | Leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g., Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, *Proteins: Structure and Molecular Properties*, W.H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins or polypeptides herein is through defining the variants and derivatives in terms of homology/identity to specific known sequences. Specifically disclosed are variants of these and other proteins or polypeptides herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% homology to the stated sequence. Those of skill in the art readily understand how to determine the homology of two proteins or polypeptides. For example, the homology can be calculated after aligning the two sequences so that the homology is at its highest level.

As described above, another way of calculating homology can be performed by published algorithms. Optimal alignment of sequences for comparison may be conducted by the local homology algorithm of Smith and Waterman, *Adv. Appl.*

Math. 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

It is understood that the description of conservative mutations and homology can be combined together in any combination, such as embodiments that have at least 70% homology to a particular sequence wherein the variants are conservative mutations.

As this specification discusses various proteins and protein sequences, polypeptides and polypeptide sequences it is understood that the nucleic acids that can encode those protein or polypeptide sequences are also disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is contemplated and understood that each and every sequence is in fact disclosed and described herein through the disclosed protein sequence. It is also contemplated and understood that while no amino acid sequence indicates what particular DNA sequence encodes that protein within an organism, where particular variants of a disclosed protein are disclosed herein, the known nucleic acid sequence that encodes that protein from which that protein arises is also known and herein disclosed and described.

It is contemplated and understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods in Molec. Biol.* 77:43-73 (1991), Zoller, *Current Opinion in Biotechnology,* 3:348-354 (1992); Ibba, *Biotechnology & Genetic Engineering Reviews* 13:197-216 (1995), Cahill et al., *TIBS,* 14(10):400-403 (1989); Benner, *TIB Tech,* 12:158-163 (1994); Ibba and Hennecke, *Bio/technology,* 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include CH2NH—, —CH2S-, —CH2-CH2-, —CH═CH- (cis and trans), —COCH2-, —CH(OH)CH2-, and —CHH2SO—(These and others can be found in Spatola, A. F. in *Chemistry and Biochemistry of Amino Acids, Peptides, and Proteins,* B. Weinstein, eds., Marcel Dekker, New York, p. 267 (1983); Spatola, A. F., *Vega Data* (March 1983), Vol. 1, Issue 3, "Peptide Backbone Modifications" (general review); Morley, *Trends Pharm Sci* (1980) pp. 463-468; Hudson, D. et al., *Int J Pept Prot Res* 14:177-185 (1979) (—CH2NH—, CH2CH2-); Spatola et al., *Life Sci* 38:1243-1249 (1986) (—CH H2-S); Hann J., *Chem. Soc Perkin Trans.* 1307-314 (1982) (—CH═CH—, cis and trans); Almquist et al., *J. Med. Chem.* 23:1392-1398 (1980) (—COCH2-); Jennings-White et al., *Tetrahedron Lett* 23:2533 (1982) (—COCH2-); Szelke et al., European Appln, EP 45665 CA (1982): 97:39405 (1982) (—CH(OH)CH2-); Holladay et al., *Tetrahedron. Lett* 24:4401-4404 (1983) (—C(OH)CH2-); and Hruby, *Life Sci* 31:189-199 (1982) (—CH2-S—); each of which is incorporated herein by reference. A particularly preferred non-peptide linkage is —CH2NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch, *Ann. Rev. Biochem.* 61:387 (1992), incorporated herein by reference).

Methods of Making the Compositions

The compositions disclosed herein and the compositions used to perform the disclosed methods can be made using any method known to those of skill in the art for that particular reagent or compound unless otherwise specifically noted.

Peptide Synthesis

The peptides of this invention can be readily synthesized by solid phase methods and a variety of combinations are possible to achieve specifically required results. An advantage of the use of solid phase techniques is that the product can be directly synthesized with the C-terminus amidated or otherwise blocked, which is beneficial in forming the procytotoxins of the invention.

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two step chemical reaction (Dawson et al., "Synthesis of Proteins by Native Chemical Ligation," *Science*, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini Met al. (1992) *FEBS Lett.* 307:97-101; Clark-Lewis I et al., J. Biol. Chem., 269:16075 (1994); Clark-Lewis I et al., *Biochemistry*, 30:3128 (1991); Rajarathnam K et al., *Biochemistry* 33:6623-30 (1994)). Alternatively, unprotected peptide segments are chemically linked where the bond formed between the peptide segments as a result of the chemical ligation is an unnatural (non-peptide) bond (Schnolzer, M et al., *Science*, 256:221 (1992)). This technique has been used to synthesize analogs of protein domains as well as large amounts of relatively pure proteins with full biological activity (deLisle Milton R C et al., *Techniques in Protein Chemistry I*, Academic Press, New York, pp. 257-267 (1992)). Another method of producing the disclosed proteins or polypeptides is to use recombinant DNA methods such as those described in U.S. Pat. No. 4,816,567. DNA encoding the proteins can be readily isolated and sequenced using conventional procedures. The hybridoma cells can serve as a source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce the protein, to obtain the synthesis of the protein in the recombinant host cells.

Substrates for use with the disclosed systems and methods can use fluorescence resonance energy transfer (FRET). Molecular energy transfer (MET) is a process by which energy is passed non-radiatively between a donor molecule and an acceptor molecule. Fluorescence resonance energy transfer (FRET) is a form of MET. FRET arises from the properties of certain chemical compounds; when excited by exposure to particular wavelengths of light, they emit light (i.e., they fluoresce) at a different wavelength. Such compounds are termed fluorophores. In FRET, energy is passed non-radiatively over a long distance (10-100 Å) between a donor molecule, which is a fluorophore, and an acceptor molecule. The donor absorbs a photon and transfers this energy nonradiatively to the acceptor (Forster, 1949, *Z. Naturforsch.* A4:321-327; Clegg, 1992, *Methods Enzymol.* 211: 353-388).

When two fluorophores whose excitation and emission spectra overlap are in close proximity, excitation of one fluorophore will cause it to emit light at wavelengths that are absorbed by and that stimulate the second fluorophore, causing it in turn to fluoresce. In other words, the excited-state energy of the first (donor) fluorophore is transferred by a resonance induced dipole—dipole interaction to the neighboring second (acceptor) fluorophore. As a result, the lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quencher.

Pairs of molecules that can engage in fluorescence resonance energy transfer (FRET) are termed FRET pairs. In order for energy transfer to occur, the donor and acceptor molecules can typically be in close proximity (up to 70 to 100 Å.) (Clegg, 1992, *Methods Enzymol.* 211: 353-388; Selvin, 1995, *Methods Enzymol.* 246: 300-334). The efficiency of energy transfer falls off rapidly with the distance between the donor and acceptor molecules. According to Forster (1949, *Z. Naturforsch.* A4:321-327), the efficiency of energy transfer is proportional to Dx10-6, where D is the distance between the donor and acceptor. Effectively, this means that FRET can most efficiently occur up to distances of about 70 Å.

Molecules that are commonly used in FRET include fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

In the 1970's, FRET labels were incorporated into immunofluorescent assays used to detect specific antigens (Ullman et al. U.S. Pat. Nos. 2,998,943; 3,996,345; 4,160,016; 4,174,384; and 4,199,559). Later, in the early 1980's, several patents were received by Heller and coworkers concerning the application of energy transfer for polynucleotide hybridization (U.S. Pat. Nos. 4,996,143, 5,532,129, and 5,565,322). In European Patent Application 82303699.1 (publication number EP 0 070 685 A2 dated Jan. 26, 1983), "Homogeneous Nucleic Acid Hybridization Diagnostics by Non-Radioactive Energy Transfer," the inventors claim that they can detect a unique single stranded polynucleotide sequence with two oligonucleotides: one containing the donor fluorophore, the other, an acceptor. When both oligonucleotides hybridize to adjacent fragments of analyzed DNA at a certain distance, energy transfer can be detected.

In European Patent Application 86116652.8 (publication number EP 0 229 943 A2 dated Jul. 29, 1987; "EP '943"), entitled "Fluorescent Stokes Shift Probes for Polynucleotide Hybridization Assays," applicants propose the same schema, but with specified distances between donor and acceptor for maximum FRET. They also disclose that the donor and acceptor labels can be located on the same probe (see, e.g., EP '943: Claim 2 and FIG. 1).

A similar application of energy transfer was disclosed by Cardullo et al. in a method of detecting nucleic acid hybridization (1988, *Proc. Natl. Acad. Sci. USA* 85: 8790-8794). Fluorescein (donor) and rhodamine (acceptor) are attached to 5' ends of complementary oligodeoxynucleotides. Upon hybridization, FRET may be detected. In other experiments, FRET occurred after hybridization of two fluorophore-labeled oligonucleotides to a longer unlabeled DNA. This system is the subject of U.S. patent application Ser. No. 661,071, and PCT Application PCT/US92/1591, Publication No. WO 92/14845 dated Sep. 3, 1992 ("PCT '845," entitled "Diagnosing Cystic Fibrosis and Other Genetic Diseases Using Fluorescence Resonance Energy Transfer"). PCT '845 discloses a method for detection of abnormalities in human chromosomal DNA associated with cystic fibrosis by hybridization. The FRET signal used in this method is generated in a manner similar to that disclosed by Heller et al. (see PCT '845 FIG. 1). Other publications have disclosed the use of energy transfer in a method for the estimation of distances between specific sites in DNA (Ozaki and McLaughlin, 1992, *Nucl. Acids Res.* 20: 5205-5214), in a method for the analysis of structure of four way DNA junction (Clegg et al. 1992, *Biochem.* 31: 4846-4856), and in a method for observing the helical geometry of DNA (Clegg et al., 1993, *Proc. Natl. Acad. Sci. USA* 90: 2994-2998).

As described above, fluorescence resonance energy transfer (FRET) is one form of molecular energy transfer (MET). In FRET, the energy donor is fluorescent, but the energy acceptor may be fluorescent or non-fluorescent. In the case of a fluorescent energy acceptor, energy transfer results in a decrease in the emission of the donor or an increase in emission of the acceptor (Clegg, 1992, *Methods Enzymol.* 211: 353-388; Selvin, 1995, *Methods Enzymol.* 246: 300-334; Stryer, 1978, *Ann. Rev. Biochem.* 47:819-846). In the case of a non-fluorescent acceptor, e.g., a chromophore or a quencher, energy transfer results in an increase in the emission of the donor (Matayoshi, et al., 1990, *Science* 247: 954-958; Tyagi and Kramer, 1996, Nature Biotech. 14:303-309; Steinberg, 1991, *Ann. Rev. Biochem.* 40:83-114).

In another form of MET, the energy donor is non-fluorescent, e.g., a chromophore, and the energy acceptor is fluorescent. In this case, energy transfer results in an increase in the emission of the acceptor (Heller, U.S. Pat. Nos. 5,532,129 and 5,565,322; Steinberg, 1991, *Ann. Rev. Biochem.* 40:83-114).

In yet another form of MET, the energy donor is luminescent, e.g., bioluminescent, chemiluminescent, electrochemiluminescent, and the acceptor is fluorescent. In this case, energy transfer results in an increase in the emission of the acceptor (Selvin, 1995, *Methods Enzymol.* 246: 300-334, Heller European Patent Publication 0070685A2, dated Jan. 26, 1993; Schutzbank and Smith, 1995, *J. Clin. Microbiol.* 33:2036-2041). An example of such an energy transfer system is described by Selvin (supra), wherein a luminescent lanthanide chelate, e.g., terbium chelate or lanthanide chelate, is the donor, and an organic dye such as fluorescein, rhodamine or CY-5, is the acceptor. Particularly efficient MET systems using this strategy include terbium as a donor and fluorescein or rhodamine as an acceptor, and europium as a donor and CY-5 as an acceptor. The reverse situation, i.e., wherein the donor is fluorescent and the acceptor is luminescent, is termed "sensitized luminescence," and energy transfer results in an increase in emission of the acceptor (Dexter, 1953, *J. Chem. Physics* 21: 836-850).

In a theoretically possible form of MET, the energy donor may be luminescent and the energy acceptor may be non-fluorescent. Energy transfer results in a decrease in the emission of the donor.

Thus, a detection system is provided for real-time in vivo monitoring of biological processes. The system, in one aspect, comprises at least one substrate having a first state that can be altered by enzymatic activity within a subject's interstitial fluid to a second detectable state. The system can further comprise an interstitial probe that can be selectively positioned within interstitial fluid of the subject. The probe can be configured to deliver substrate in the first state into the interstitial fluid of the subject and is further configured to receive interstitial fluid comprising substrate in the second detectable state. The system can also include a detector apparatus having a substrate receptacle, an energy source and a detector element. The substrate receptacle is in fluid communication with the probe and is configured to accept the interstitial fluid having substrate in the second detectable state. Means are provided for positioning the substrate receptacle, energy source and detector element within the detector apparatus such that energy generated by the energy source can be directed into the substrate receptacle to excite the detectable substrate such that the excited detectable substrate can be detected by the detector element.

Figure 8:
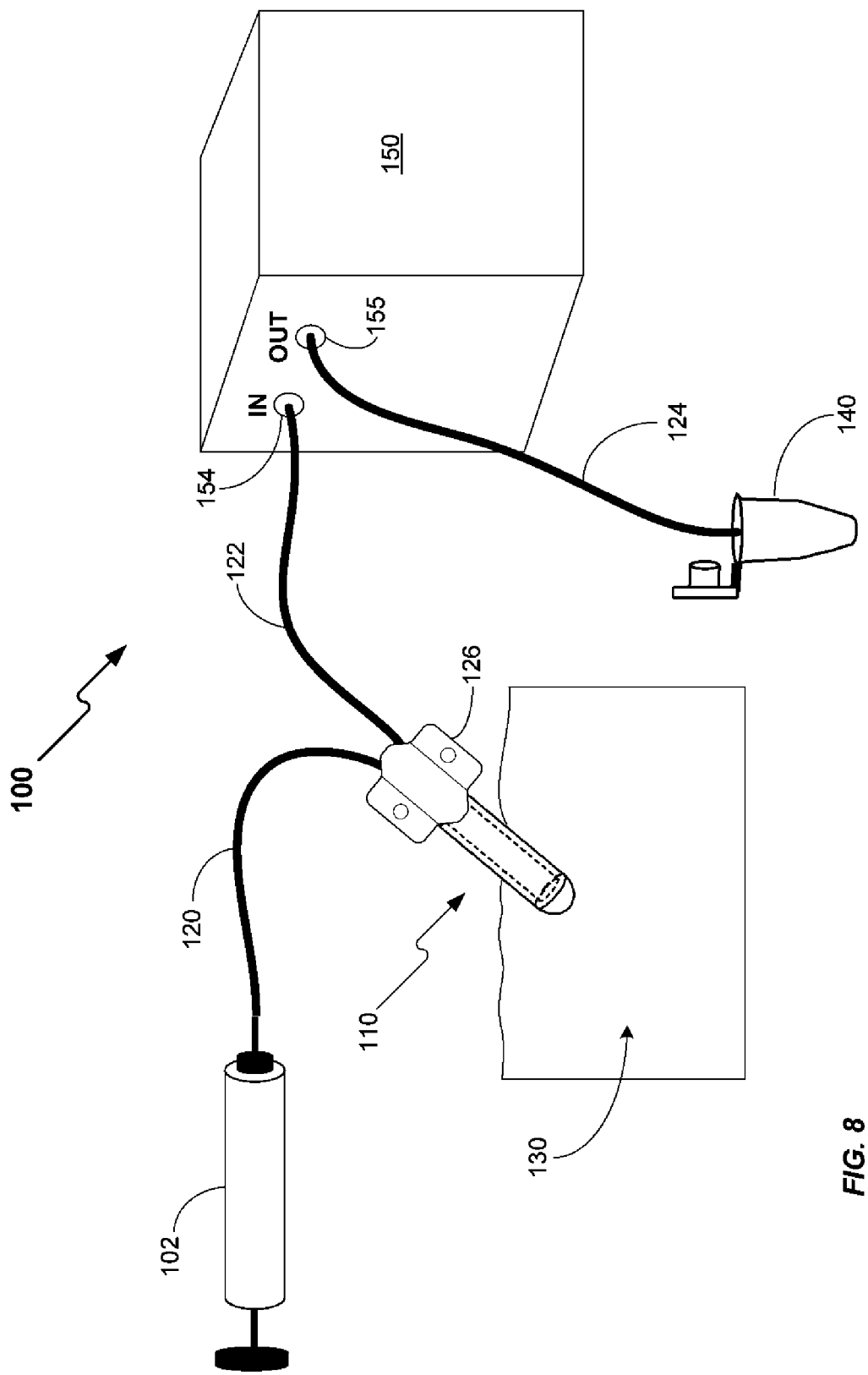
FIG. 8 is a schematic diagram of an exemplary system of the present invention, according to one aspect.

In a further aspect and as illustrated in FIG. 8, the system 100 comprises an introducer device 102 configured for delivering the substrate in the first state to the probe 110. As shown in FIG. 1, an exemplary introducer device 102 comprises a syringe 104 and a needle 106. The introducer device can further comprise a syringe pump and controller that controls the power to and the flow rate of the syringe pump (such as the Baby Bee® Syringe Pump and Worker Bee® Controller, respectively, of Bioanalytical Systems, Inc.). The exemplary controller allows for flow rates from about 0.1 µL/min to about 100 µL/min, such as, for example, 0.1, 0.2, 0.5, 0.8, 1.0, 1.5, 2.0, 2.5, 3, 4, 5, 8, 10, 20, 50 and 100 µL/min, when connected to a syringe. However, it is contemplated that other flow rates can be used BA, as can be determined based factors such as, for example, the biological process being measured, the substrate being used, the subject, and the anatomical location of the interstitial fluid. The syringe pump can comprise a holding unit that holds a syringe therein. One or more screws can be located on the top of the syringe pump that allow for the placement and movement of the syringe plunger. Syringes can range from about 1 mL to about 3 mL syringes, such as a 3 mL Becton Dickinson syringe having 1/10 mL gradations, although other syringes can be used. In some aspects, an ampule or cartridge can be used which can vary in volume of substrate. In one aspect, the substrate can be stored in the ampule or substrate in a lyophilized or dehydrated state. In this aspect, the substrate can be hydrated or reconstituted using fluid prior to administration to the interstitial fluid of a subject. In one aspect the ampule or cartridge can comprise lyophilized substrate and a fluid that can be mixed when desired for use with the systems and methods.

In a particular aspect, the syringe can comprise a material that is opaque and substantially impermeable to light. Optionally, the syringe can be wrapped in a material that is impermeable to light, such as foil or other opaque materials. The syringe can be filled with an MMP activity indicator, which in one aspect is a fluorogenic substrate that is quenched when intact, as will be described further herein below. Optionally, the MMP activity indicator is a non-fluorescent substrate that only fluoresces in an altered state.

A distal end of the syringe 104 can be connected to a needle 106 for delivery of the MMP activity indicator (i.e., the substrate in its first state) to an inlet tube. In one aspect, the needle comprises a blunt needle that connects to the syringe via luer lock. In yet a further aspect, the needle can be an aluminum hub blunt needle that is 23 gauge by approximately 1 inch, such as the Monoject™ Aluminum Hub Needle.

Figure 2:
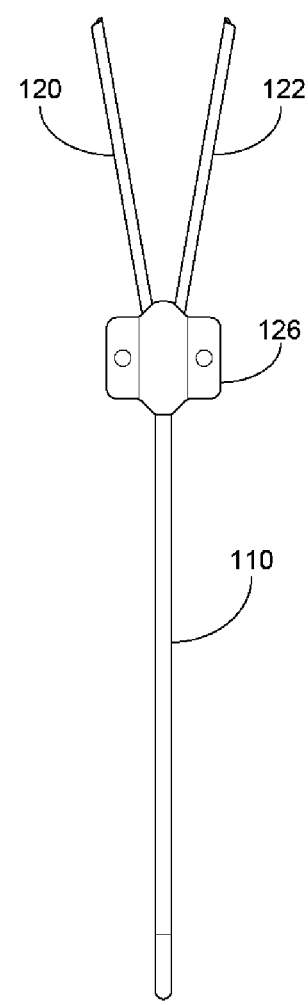
FIG. 2 is an exemplary probe for use with systems and methods of the present invention, according to another aspect.

The introducer device 102 can be connected to a probe 110, such as shown in FIG. 8, via an inlet tube 120. The inlet tube (as well as other tubes, such as outlet and discharge tubes described herein), in one aspect, can comprise polyetheretherketone (PEEK) tubing. PEEK tubing generally has high strength and heat resistant properties. In a particular aspect, the tubing as an outer diameter of about 0.65 mm and an inner diameter of about 0.12 mm. In one aspect, the tubing can be opaque and/or covered in an opaque material to protect the conduit of the tubing from light. As shown in FIG. 2, the inlet tube 120 can be connected to a proximal portion of the probe 110. A tubing connector 126 can be provided to connect multiple pieces of tubing such as shown in FIG. 2. As can be seen, the connector can "splice" together multiple pieces of tubing, or a piece of tubing and the probe and eliminate any dead space.

Figure 3:
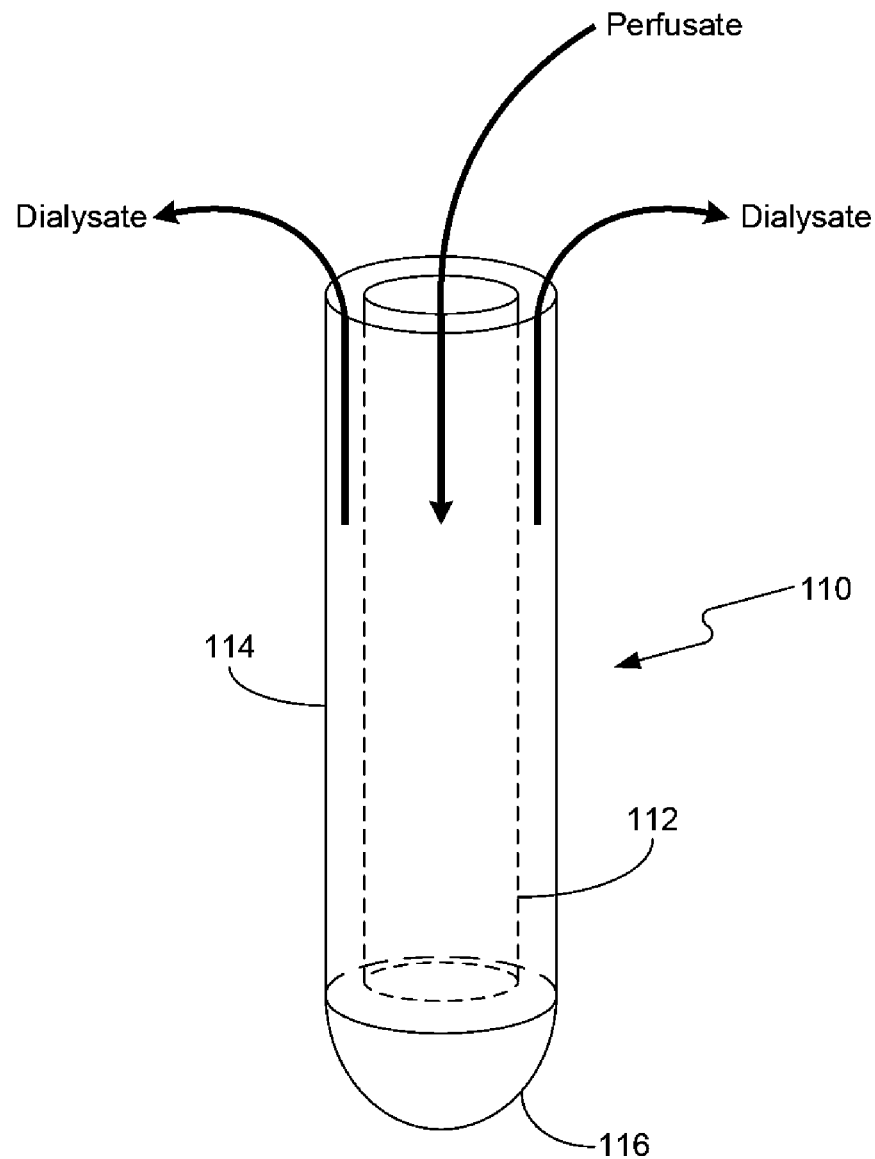
FIG. 3 illustrates the movement of substances therethrough a probe of the present invention, according to one aspect.

An exemplary probe 110 is illustrated in FIG. 3. The probe can comprise an inner shaft 112, outer shaft 114, and membrane portion 116 located at a distal end of the probe. The inner shaft can be formed substantially concentrically to the outer shaft, and can be spaced apart from the outer shaft, thereby defining a space between the two shafts. In one aspect, the probe is designed for dialysis in moving soft tissues, such as muscle, heart, skin and adipose tissue, among others. An exemplary probe that can be used is the CMA/20 Elite Microdialysis Probe (CMA Microdialysis AB, Solna, Sweden). This probe has a PAES membrane with 20,000 Daltons cut-off and has high recovery with a 4 mm long membrane.

As shown in FIG. 3, an exemplary probe is configured to receive perfusate (such as a substrate in a first, unaltered state) therein the inner shaft, which can flow from a proximal portion of the probe to the opposing distal portion. Dialysate can pass in the space between the inner and outer shaft from the distal portion of the probe to the proximal portion. An outlet tube 122 can be connected to the proximal end of the probe via the tubing connector 126, as shown in FIGS. 2 and 8, for example. The outlet tube can be configured to pass the dialysate from the probe to a detector 150, as described further below.

The probe can vary in size. The size of the probe can be selected by one of skill in the art based on the desired detection protocol. For example, any measurable parameter of the probe can vary including the length, width, lumen diameter, size of openings in the probe membrane for communication with the tissue. Optionally, a 4 mm-long membrane, 20 kDa membrane cutoff size; outer diameter of probe shaft, 0.77 mm; outer diameter of probe membrane, 0.5 mm, can be used (CMA/Microdialysis, North Chelmsford, Mass.).

Figure 9A:
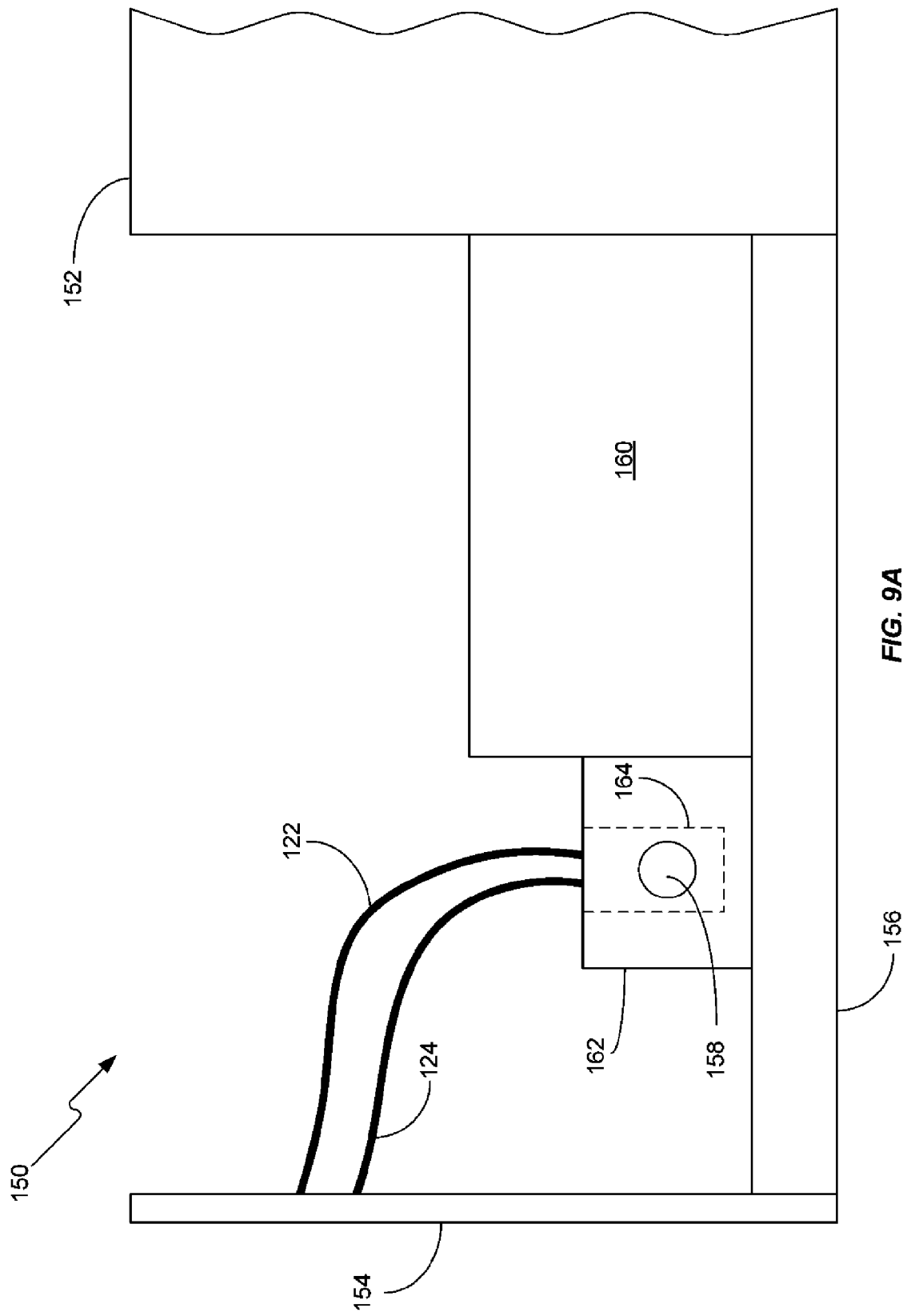
FIG. 9A is a side elevational view of an exemplary detector, according to one aspect of the present invention.
Figure 9B:
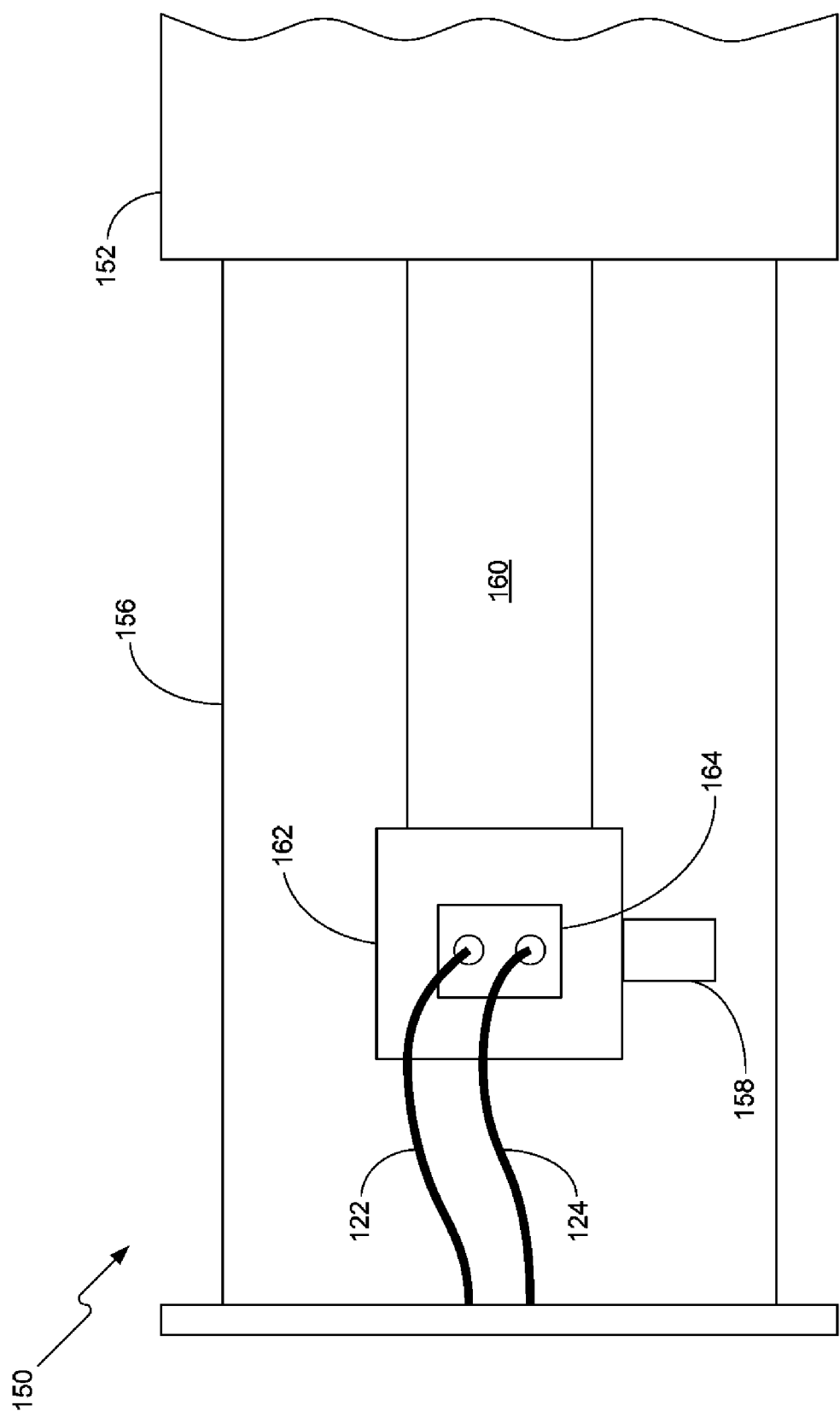
FIG. 9B is a top plan view of the exemplary detector of FIG. 9A, according to another aspect of the present invention.

A detector 150, according to various aspects, comprises a box 152 that substantially encompasses the detector components such as a substrate receptacle, energy source, and detector element. The box can have a front surface 154 that is separable from the remainder of the box. For example, as shown in FIG. 9A, a support base 156 can be provided that is configured to roll or slide in and out of the box, and the front cover can be positioned at a distal end of the support base. Thus, when closed, it is contemplated that the box fully surrounds the detector components. The box can be made of an opaque material such that when the box is closed, light is prevented from entering into the interior of the box.

The detector further comprises a cuvette holder 162 that is sized and shaped to receive a substrate receptacle, such as a cuvette 164. The cuvette, in one aspect, can be a UV-transparent, micro-volume cuvette configured for fluorescence analysis. For example, a CFV-series FluoroVettes cuvette (Ocean Optics, Inc., Dunedin, Fla.) can be used. These cuvettes have a 50 µL contained volume and can transmit UV light to 220 nm.

An energy source, such as, for example, a light source 158, can be positioned substantially adjacent the cuvette holder and is configured to direct light through the cuvette holder at the cuvette. The light source can be configured to direct light of a particular wavelength or wavelength band at the cuvette. Optionally, one or more filters can be provided that can be positioned between the light source and the cuvette. The filter(s) can filter the light to allow only light of a specific wavelength to pass therethrough. The detector 150 further comprises a detector element, such as a photomultiplier tube (PMT) 160. The PMT is aimed at the cuvette and is configured to detect light therein the cuvette when the light source directs light at the cuvette. As is known in the art, a PMT is configured to detect light and multiply the signal produced by the light, from which photons can be measured.

Figure 10:
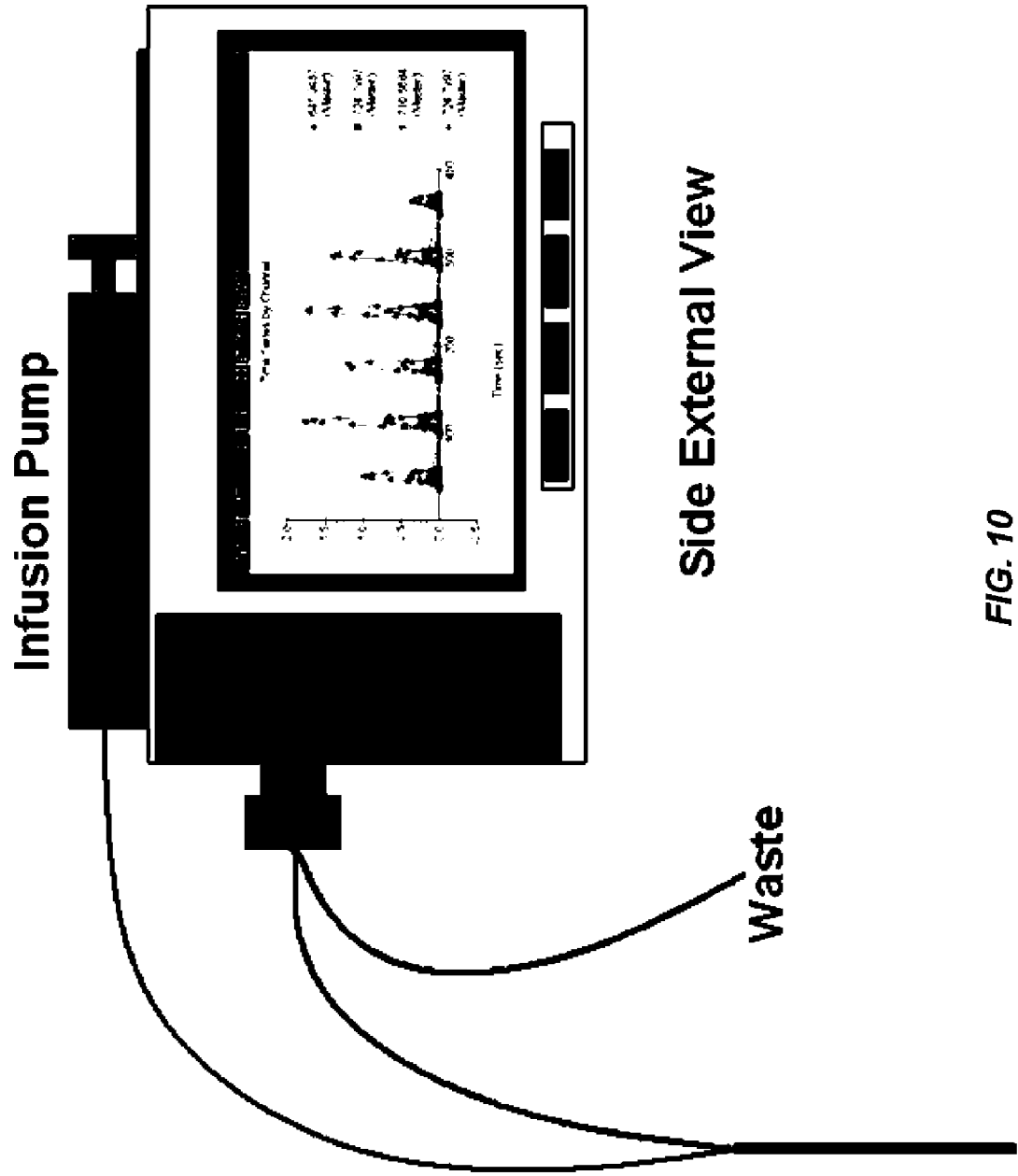
FIG. 10 illustrates an exemplary system comprising an infusion pump, dialysis probe, detector, and display, according to one aspect of the present invention.

An exemplary detector 150 is the FIAlab PMT-FL device (FIAlab Instruments, Inc., Bellevue, Wash.). This device is a flow-through, in-line fluorescence detector that can have a built-in 280 nm light emitting diode (LED). The device uses a PMT to measure fluorescence. The substrate in the second detectable state passes into the detector 150 via the probe-outlet tube 122 and passes through a cuvette 164 housed inside the detector. In one aspect, the cuvette has a volume of about 10 µL to about 50 µL. The FIAlab PMT-FL plugs into the RS-232 serial port of a computer and comes with Windows-based software. Thus, due to the flow-through nature of the detector 150, the detected substrate can be continuously monitored by a processor system, such as a computing device. The processor system can comprise a monitor for displaying the results of the detection, such as shown in FIG. 10.

Thus, aspects of the exemplary systems disclosed herein can be implemented via a general-purpose computing device in the form of a computer. The components of the computer can include, but are not limited to, one or more processors or processing units, a system memory, and a system bus that couples various system components including the processor to the system memory.

The system bus can represent one or more of several possible types of bus structures, including a memory bus or memory controller, a peripheral bus, an accelerated graphics port, and a processor or local bus using any of a variety of bus architectures. By way of example, such architectures can include an Industry Standard Architecture (USA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection. The bus, and all buses specified in this description can also be implemented over a wired or wireless network connection and each of the subsystems, including the processor, a mass storage device, an operating system, application software, data, a network adapter, system memory, an Input/Output Interface, a display adapter, a display device, and a human machine interface, can be contained within one or more remote computing devices at physically separate locations, connected through buses of this form, in effect implementing a fully distributed system.

The computer typically includes a variety of computer readable media. Such media can be any available media that is accessible by the computer and includes both volatile and non-volatile media, removable and non-removable media. The system memory can include computer readable media in the form of volatile memory, such as random access memory (RAM), and/or non-volatile memory, such as read only memory (ROM). The system memory typically contains data such as data and/or program modules such as operating system and application software that are immediately accessible to and/or are presently operated on by the processing unit. Application software can include emission detection and analysis software.

The computer may also include other removable/non-removable, volatile/non-volatile computer storage media. By way of example, a mass storage device can provide non-volatile storage of computer code, computer readable instructions, data structures, program modules, and other data for the computer. For example, a mass storage device can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device, including by way of example, an operating system and application software. Each of the operating system and application software (or some combination thereof) may include elements of the programming and the application software. Data can also be stored on the mass storage device. Data can be stored in any of one or more databases known in the art. Examples of such databases include, DB2®, Microsoft® Access, Microsoft® SQL Server, Oracle®, mySQL, PostgreSQL, and the like. The databases can be centralized or distributed across multiple systems.

A user can enter commands and information into the computer via an input device. Examples of such input devices include, but are not limited to, a keyboard, pointing device (e.g., a "mouse"), a microphone, a joystick, a serial port, a scanner, and the like. These and other input devices can be connected to the processing unit via a human machine interface that is coupled to the system bus, but may be connected by other interface and bus structures, such as a parallel port, game port, or a universal serial bus (USB).

In an exemplary system of an embodiment according to the present invention, the user interface can be chosen from one or more of the input devices listed above. Optionally, the user interface can also include various control devices such as toggle switches, sliders, variable resistors and other user interface devices known in the art. The user interface can be connected to the processing unit. It can also be connected to other functional portions of the exemplary system described herein in conjunction with or without connection with the processing unit connections described herein.

A display device can also be connected to the system bus via an interface, such as a display adapter. For example, a display device can be a monitor or an LCD (Liquid Crystal Display). In addition to the display device, other output peripheral devices can include components such as speakers (not shown) and a printer (not shown) which can be connected to the computer via an Input/Output Interface.

The computer can operate in a networked environment using logical connections to one or more remote computing devices. By way of example, a remote computing device can be a personal computer, portable computer, a server, a router, a network computer, a peer device or other common network node, and so on. Logical connections between the computer and a remote computing device can be made via a local area network (LAN) and a general wide area network (WAN). Such network connections can be through a network adapter. A network adapter can be implemented in both wired and wireless environments. Such networking environments are commonplace in offices, enterprise-wide computer networks, intranets, and the Internet. The remote computer may be a server, a router, a peer device or other common network node, and typically includes all or many of the elements already described for the computer. In a networked environment, program modules and data may be stored on the remote computer. The logical connections include a local area network ("LAN") and a wide area network ("WAN"). Other connection methods may be used, and networks may include such things as the "world wide web" or internet.

Application programs and other executable program components such as the operating system can reside at various times in different storage components of the computing device, and can be executed by the data processor(s) of the computer. An implementation of application software may be stored on or transmitted across some form of computer readable media. Computer readable media can be any available media that can be accessed by a computer. By way of example, and not limitation, computer readable media may comprise "computer storage media" and "communications media." Computer storage media include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer. An implementation of the disclosed method may be stored on or transmitted across some form of computer readable media.

The processing of the disclosed method and systems can be performed by software components. For example the processing of the detected light emissions can be performed by software components. The disclosed method may thus be described in the general context of computer-executable instructions, such as program modules, being executed by one or more computers or other devices. Generally, program modules include computer code, routines, programs, objects, components, data structures, etc. that perform particular tasks or implement particular abstract data types. The disclosed method may also be practiced in grid-based and distributed computing environments where tasks are performed by remote processing devices that are linked through a communications network. In a distributed computing environment, program modules may be located in both local and remote computer storage media including memory storage devices.

Aspects of the exemplary systems and methods can be implemented in various forms including hardware, software, and a combination thereof. The hardware implementation can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc. The software comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

The detector 150 can be operatively connected to the computer using any suitable means. For example, a modem cable with DB9 female to DB25 male can be used to connect the PMT-FL to a laptop computer.

As described above, the computer can comprise software for the detection and analysis of changes in fluorescence. The software can comprise a computer-readable medium having computer readable program code for determining and or quantifying fluorescence or light emissions of one or more substrates detected by the detector. Software can comprise program code to receive data from the detector device. The software can further comprise program code to determine the characteristics to the light detected by the detector. For example, the software can determine and analyze light detected by the detector at one or more wavelengths. Optionally, the software can determine the presence and/or extent of one or more substrates that has been excited to admit at one or more wavelengths as detected by the detector. The substrates may have been cleaved or activated by one or more enzymes, including one or more MMPs.

For example, a software analysis package (FIAlab ver. 5) can be used that allows for real-time detection of changes in fluorescence. Thus, the systems and methods can be used to determine the presence and/or activity and/or quantity of one or more enzymes in a subject's extracellular tissue by detecting activity of the one or more enzyme of a substrate introduced into the extracellular tissue using the described methods. The software can comprise algorithms and computer readable code to make these exemplary determinations from data or signals provided by the detector.

The substrate flows through the detector and exits via the discharge tube 124. The substrate can be discharged to a collection device 140 for further measurement or analysis, or can otherwise be disposed of.

Methods are provided for real-time in vivo monitoring of biological processes using exemplary systems as described herein and in vitro-validated substrates. In one aspect, the method comprises identifying a compound of interest that is located in the interstitium of a subject. It is contemplated that the activity or presence of the compound will be related to the in vivo biological process being monitored. As shown in FIG. 8, a probe 110 can be positioned within the interstitium of the subject. A fluorogenic substrate specific for the compound of interest can be placed in the introducer device 102, such as a syringe. The fluorogenic substrate can then be infused into the interstitium of the subject from the syringe, through the inlet tube 120 and into the probe. A syringe pump and controller can be used to control the flow rate from the syringe. Optionally, the syringe can be controlled manually.

If multiple substrates are used, each can be cleaved by the same enzyme or by different enzymes. Each substrate can also be excited by or emit light energy at the same wavelength or at different wave lengths. For example, a substrate can be located in the source that is excited by light having a wavelength of between about 100 and 500 nm. Optionally, substrates can be excited by light having a wavelength between about 190 and 410 nm.

Thus, any combination of substrates having differing excitation parameters is contemplated. For example, a substrate having an excitation wavelength of 330 nm can be combined with a substrate having an excitation frequency of 280 nm. Similarly, substrates having varied emission wavelengths can be combined in a source. Multiple sources can also be used. Each source can deliver substrate to the same probe, or multiple probes can be used. If multiple sources and probes are used, each can deliver a substrate having differing characteristics to the probe. For example, one source can comprise a substrate having an excitation wavelength of 330 nm and a substrate having an excitation wavelength of 280 nm. Both substrates can be delivered by this common source to a common probe 100. Also, a substrate having an excitation wavelength of 330 nm can be located in a first source and a substrate having an excitation wavelength of 280 nm can be located in a second source. Both substrates can be delivered to a first probe. Also, the 330 nm substrate can be delivered from the first source to a first probe and the 280 nm substrate can be delivered from the second source to a second probe. If multiple probes are used, they can be located in the same or different tissues of interest.

Figure 4:
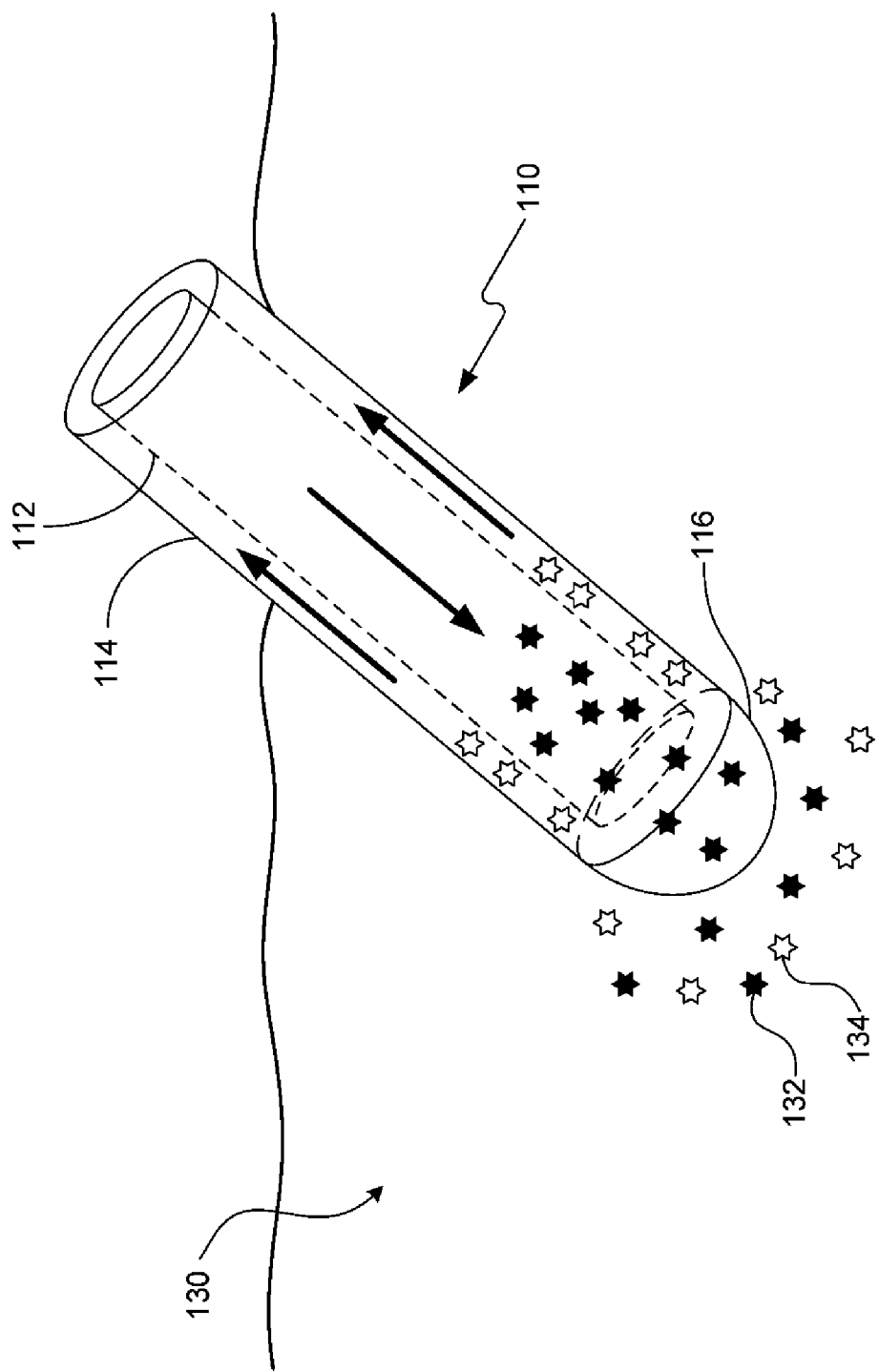
FIG. 4 illustrates a probe positioned therein tissue of a subject and the movement of substrate into and out of the tissue, according to yet another aspect of the present invention.
Figures 5A, 5B:
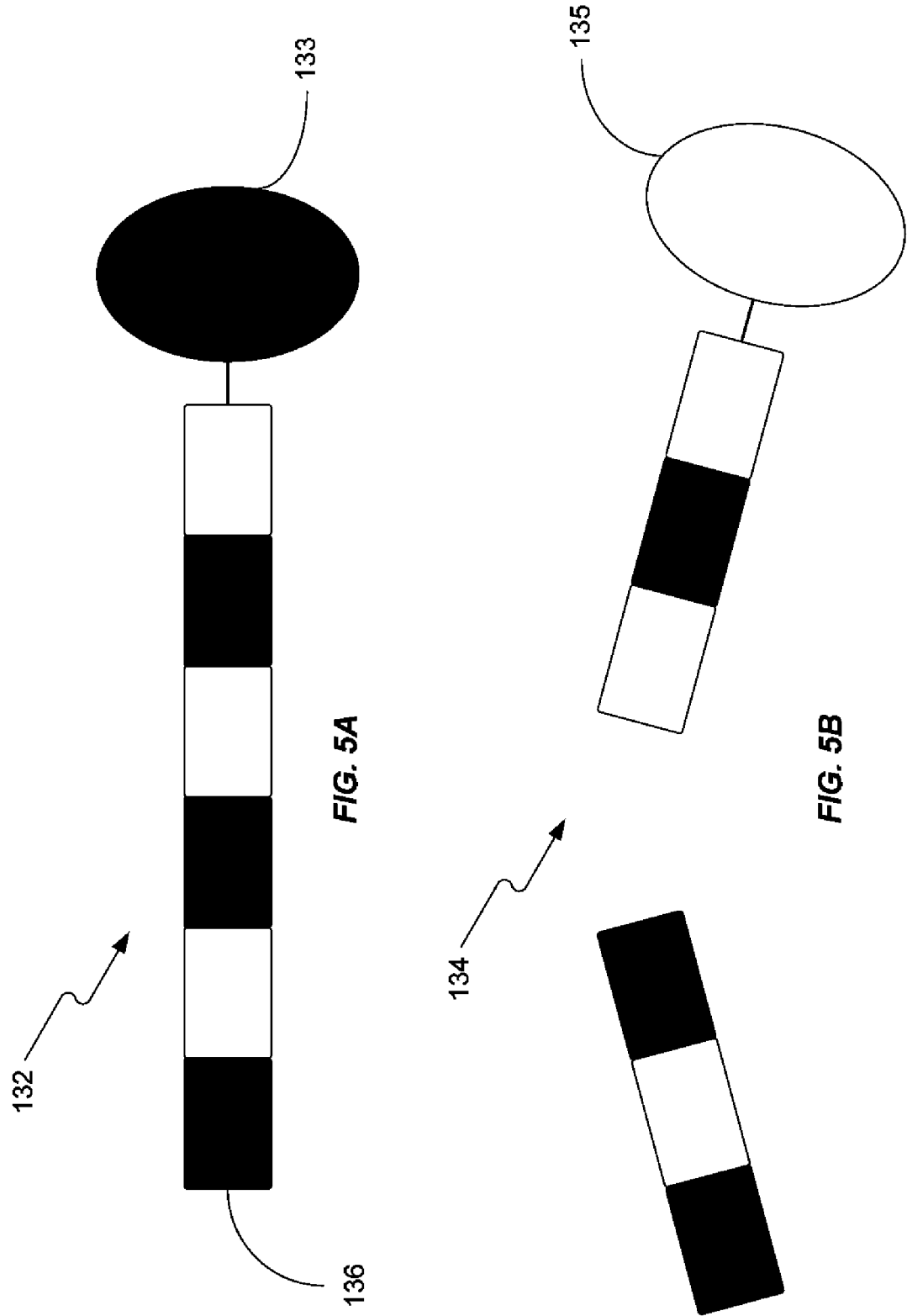
FIG. 5A shows an intact substrate molecule having a peptide sequence attached to a quenched fluorescent molecule, according to one aspect of the present invention.
FIG. 5B shows a cleaved substrate molecule having a cleaved peptide sequence and an exposed fluorescent molecule, according to another aspect of the present invention.
Figure 6:
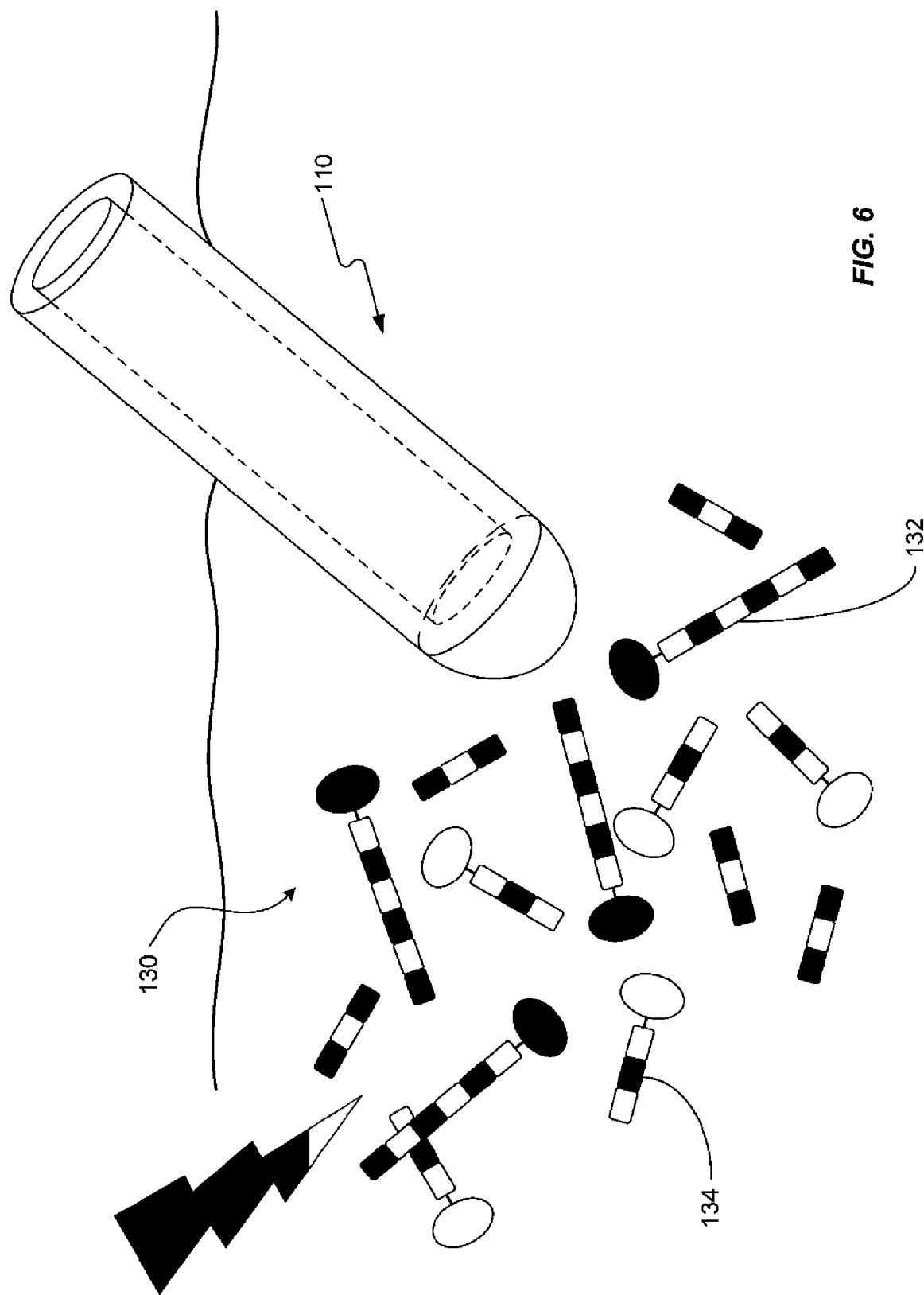
FIG. 6 illustrates a probe positioned therein tissue of a subject and the presence of intact and cleaved substrate molecules therein the tissue, according to yet another aspect of the present invention.
Figure 7:
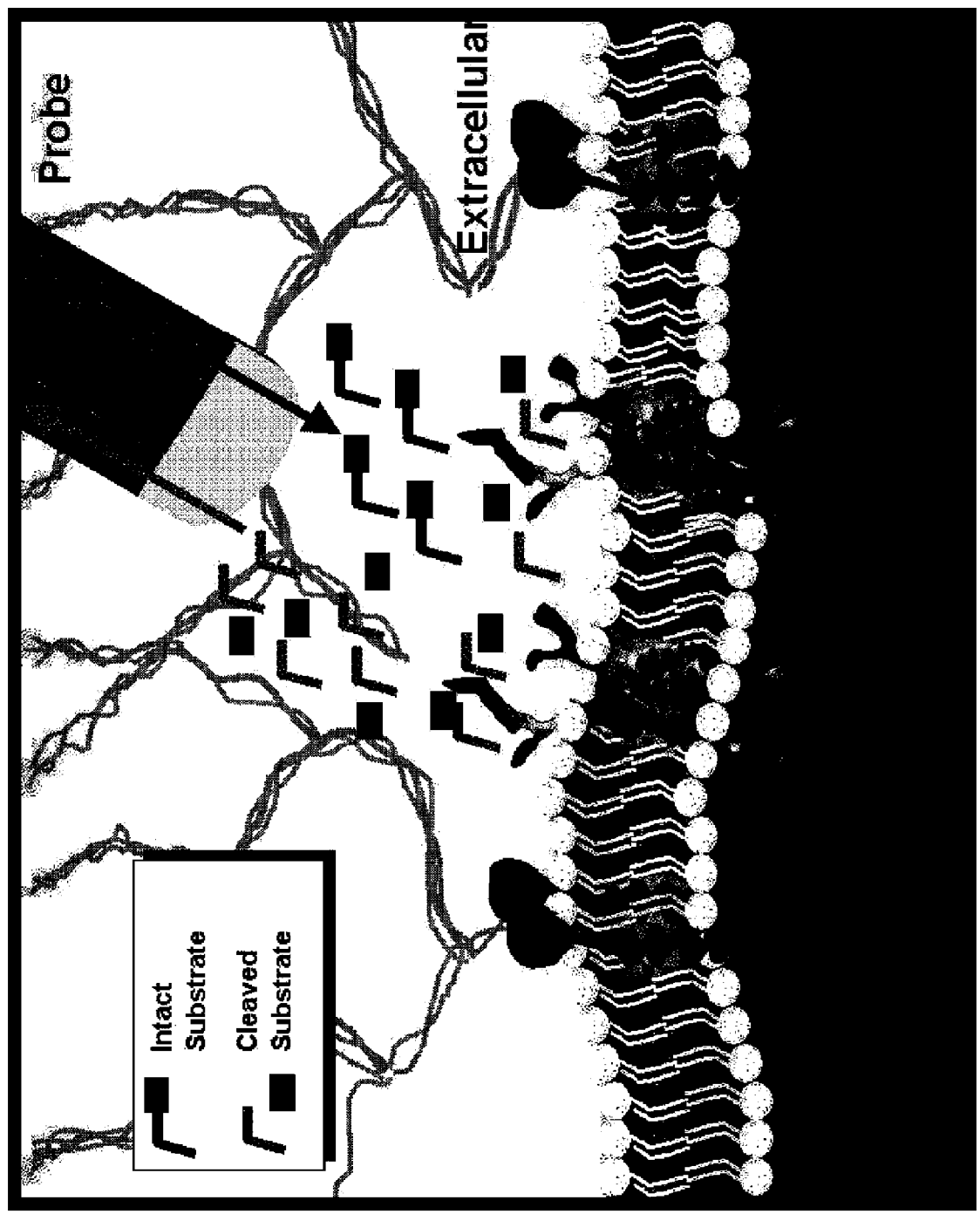
FIG. 7 is a further illustration of a probe positioned therein tissue of a subject and the presence of intact and cleaved substrate therein the tissue, according to a further aspect of the present invention.

As shown in FIG. 4, the introduced fluorogenic substrate can comprise intact substrate 132. As the substrate interacts with the interstitium of the subject, the substrate can be cleaved or otherwise modified by the compound of interest, resulting in the cleaved substrate 134. Thus, as illustrated in FIGS. 5A and 5B, the intact substrate can have a peptide sequence 136 attached to a quenched fluorescent molecule 133. When the peptide sequence is cleaved, it results in a cleaved substrate 134 having an exposed fluorescent molecule 135. The cleaved substrate passes through the membrane 116 and out of the probe, as shown by the arrows in FIG. 4.

The compound of interest can be an enzyme, which can modify the fluorogenic substrate to its detectable state. Further, the enzyme can be a catalytic enzyme and the substrate can comprise a quenched fluorescent moiety. The enzyme can alter the substrate to unquench the fluorophores, thereby producing a substrate comprising an exposed fluorescent moiety. Optionally, the compound of interest can be a protein that modifies the fluorogenic substrate into its detectable state. In yet another aspect, the compound of interest can be selected from the group consisting of a protein, an enzyme, a polypeptide and a nucleic acid, and the fluorogenic substrate can be modified into a detectable state by interaction with the compound of interest.

In yet another aspect, a plurality of substrates are provided, each having a first state that can be altered by enzymatic activity within the subject's interstitial fluid to a second detectable state. For example, a first substrate can be altered to its second detectable state by a first enzyme of the subject's interstitial fluid. A second substrate can likewise be altered to its second detectable state by a second enzyme located in the subject's interstitial fluid. According to a further aspect, the first and second substrates can be selected such that the first enzyme cannot alter the second substrate to its second detectable state, and the second enzyme cannot alter the first substrate to its second detectable state within the interstitial fluid.

The cleaved or otherwise altered substrate, or substrates, then flows through the outlet tube 122 into the detector 150 and, more specifically, into the cuvette 164. The light source 158 directs light into the cuvette so that the exposed fluorescent molecules within the cleaved substrate will fluoresce. The fluorescence is then measured by the PMT 160. The substrate continuously flows through the detector, thereby allowing for a real-time measurement of the fluorescence of the substrate.

In the aspect in which a plurality of substrates are provided, the detector can be configured to distinguishably detect the first substrate in its detectable state and the second substrate in its detectable state. For example, the first substrate in its detectable state can comprise a fluorophore that fluoresces when contacted by light of a first wavelength. Similarly, the second substrate in its detectable state can comprise a fluorophore that fluoresces when contacted by light of a second wavelength that is different from the first wavelength. Further, the fluorophore of the first substrate, when contacted by light, can fluoresce at a first wavelength. The fluorophore of the second substrate, when contacted by light, can fluoresce at a second wavelength.

As described above, in one aspect the detector comprises a filter that is operatively positioned between the light source and the substrate receptacle (e.g., a cuvette). The filter can be configured to allow for transmission of light of at least one selected wavelength into the cuvette. According to a further embodiment, a filter is provided that is configured to allow transmission of light having a first selected wavelength into the receptacle and can be selectively adjusted to allow for transmission of light having a second selected wavelength that is distinct from the first selected wavelength. The processor system can be configured to determine a ration relating the amount of first substrate in its detectable state to the amount of second substrate in its detectable state. This ration can be determined based on detected first and second substrate by the detection element (such as the PMT).

Figure 11:
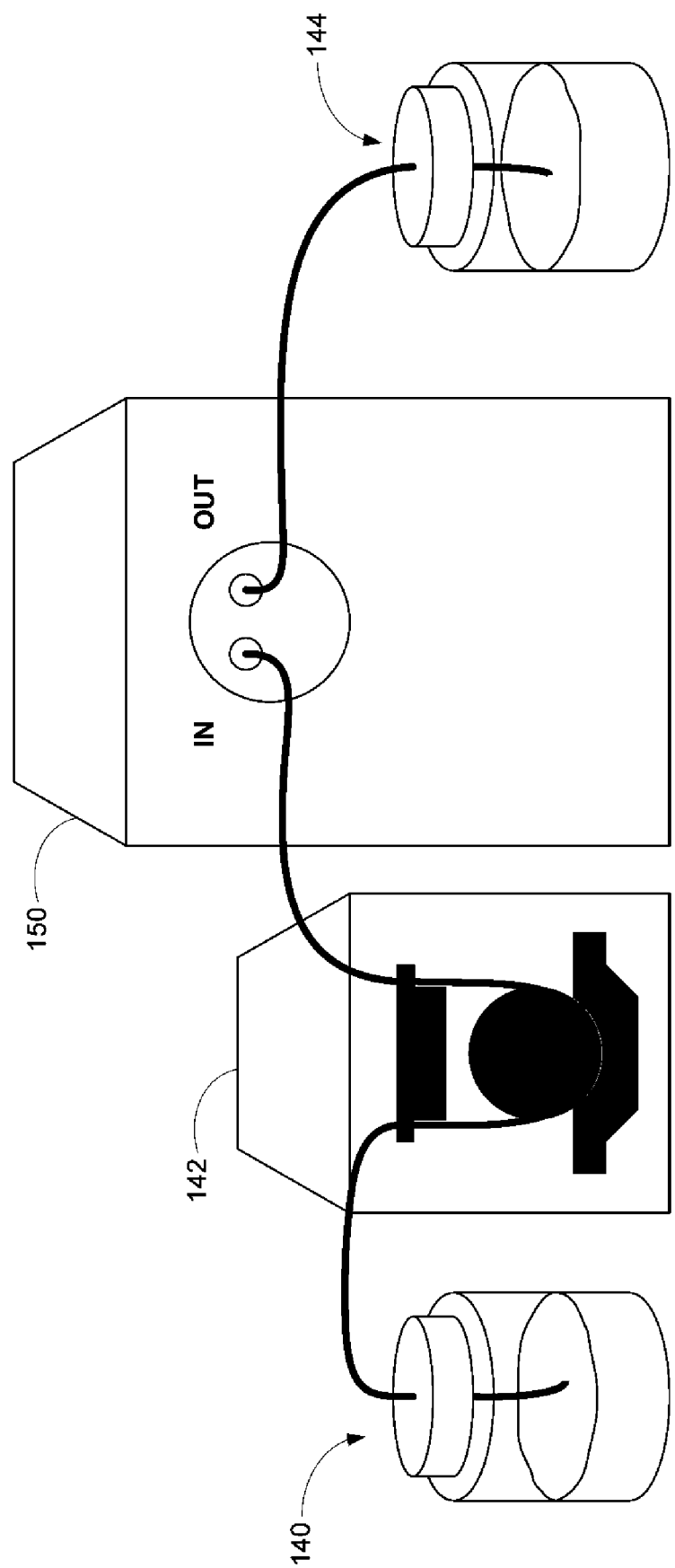
FIG. 11 illustrates an exemplary system for monitoring MMP activity in fluid removed from a subject.

The substrate then flows out of the cuvette and out of the detector via the discharge tube 124. As illustrated in FIG. 8, the substrate can flow to a collection device 140 for further study and measurements. Optionally, the measured substrate can be discarded. In one aspect, the discharged substrate can be collected and measured by a separate detector, such as shown in FIG. 11. As illustrated, a tubing is placed into the collection device 140 and is connected to a detector 150. A peristaltic pump 142, such as an S2-mini peristaltic pump provided by FIAlab Instruments, Inc. can be provided to pump the fluid from the collection device to and through the detector. The fluid passes through the detector, such as described above, and is discharged into a second collection device 144 for disposal.

Although described above with respect to a cleaved substrate that fluoresces, it is contemplated that the present systems and methods can be used to detect lack of fluorescence in the substrate. Thus, the described systems and methods can be used to detect any state change of a substrate. The substrate can have a first non-fluorescing state that can be altered by enzymatic activity within the subject's interstitial fluid to a second detectable state, such as described above. Optionally, the substrate fluoresces in its first state (i.e., a fluorogenic substrate is delivered into the interstitial fluid in its detectable state) and is altered to a non-fluorescing second state. The interaction with the compound of interest can cause a reduction in the amount of substrate that is in the detectable state. In one aspect, the reduction in the amount of detectable substrate is related to the amount of compound of interest available to interact with the delivered substrate. For example, the reduction in detectable substrate can be inversely proportional to the amount of compound of interest available to interact with the delivered substrate.

According to yet another aspect, a method is provided for real-time in vivo monitoring of a biological process. The method includes identifying a compound of interest that is located in the interstitium of the subject. The activity or presence of the compound is related to the in vivo biological process being monitored. The method can further include positioning a probe within the interstitium of the subject and infusing the interstitium of the subject through the probe with a fluorogenic substrate specific for the compound of interest. The method can also include receiving interstitial fluid, including the substrate, from the subject with the probe and detecting the received substrate to monitor the biological process in the subject.

In yet another aspect, provided are methods for in vivo measurement of MMP activity using the described systems. A family of proteolytic enzymes, the matrix metalloproteinases (MMPs) was first described in 1962 by Jerome Gross. He discovered the collagenolytic activity of tadpole tails during metamorphosis to adult frog. Since then, the field of ECM (extracellular matrix) degrading enzymes has grown considerably. MMPs function in normal physiological states such as embryonic development, ovulation, and wound healing and have been implicated in numerous pathological conditions. MMPs have been shown to degrade all extracellular matrix (ECM) components. Structurally, MMPs are comprised of a signal peptide, prodomain, catalytic domain, hinge region and hemopexin-like domain. Secreted in zymogen form, cleavage of the pro-domain is required for complete activation and subsequent proteolytic activity. There are approximately 25 known MMPs organized into 6 groups based on substrate specificity and structure. They are the collagenases (MMP-1, MMP-8, MMP-13, and MMP-18), gelatinases (MMP-2 and MMP-9), stromelysins (MMP-3 and MMP-10), matrilysins (MMP-7 and MMP-26), membrane-type MMPs (MMP-14, MMP-15, MMP-16, MMP-17, MMP-24, and MMP-25) and other MMPs (MMP-12, MMP-20, MMP-22, MMP-23 and MMP-28). One control point for net MMP proteolytic activity is the family of tissue inhibitors of metalloproteinases, or TIMPs.3, 5-8 To date, there are four TIMPs identified, with TIMP-4 being predominantly expressed in the myocardium. TIMPs bind to MMPs in a non-covalent 1:1 ratio, thereby preventing continued proteolytic activity. Discordance between MMPs and TIMPs can lead to increased ECM degradation and pathological conditions such as inflammation, tumor invasion, arthritis and cardiovascular disease.

A cause-effect relationship has been clearly established between MMP activation and adverse myocardial remodeling. Transgenic animal models have confirmed a relationship between MMP activation and LV remodeling. Kim et al. demonstrated that cardiac overexpression of human MMP-1 caused a significant loss of diastolic and systolic function similar to that of the human pathophysiology of heart failure. Likewise, it has been shown that the targeted deletion of MMP-9 attenuated LV dilation following myocardial infarction in mice. Further, Roten et al. demonstrated that deletion of TIMP-1 in mice caused changes in LV geometry without a pathological stimulus when compared to age matched control animals. The TIMP-1 deficient mouse was also shown to have increased LV remodeling following MI. Pharmacological MMP inhibition has been shown to attenuate infarct expansion and left ventricular (LV) dilation after myocardial infarction. Mukherjee et al demonstrated that MMP inhibition attenuated LV dilation post MI and reduced the degree of infarct expansion. In another study done by the applicants, it was shown that MMP inhibition caused significant attenuation in LV dilation post MI in pigs. While MMPs have been demonstrated to contribute to cardiovascular diseases, there has been no way to directly measure MMP activity in vivo.

The primary approaches used in the past for measuring MMP activation have been through collection of myocardial samples and the use of in vitro assay systems. These systems, however, do not provide a comprehensive measurement of MMP activity since endogenous regulatory mechanisms are removed.

The present systems and methods and system provide a reliable way to interrogate the interstitium. This approach provides a relative index of MMP activity within the interstitial space in vivo. The systems and methods can be used to determine the in vivo presence and/or activity and/or quantity of one or more enzymes, including, but not limited to, MMPs, in a subject's tissue by detecting activity of the one or more enzyme on a substrate introduced into the extracellular tissue of the subject.

It should be recognized that the present method and system can be utilized in a number of tissues including but not limited to cardiovascular, muscle, skin, liver, uterus, kidney, joints, etc, and utilized in normal and neoplastic disease states. Described herein are the in vivo characterization of the fluorogenic substrate and the utilization of the method and system in human subjects.

The applications of this method and system of the present invention include placement of the microdialysis system in any tissue structure that can be made accessible to a hypodermic needle. Thus, measurements can be readily obtained by microdialysis placement in the skin and muscle. Using a surgical approach, the microdialysis system can be placed in any anatomical structure. Examples of how surgical placement of the microdialysis system can be utilized in both experimental and clinical applications are provided in the subsequent sections.

Provided is a method of real-time in vivo measurement of matrix metalloproteinase (MMP) activity of a specific matrix metalloproteinase in a subject, comprising: a) contacting a tissue of the subject with a microdialysis probe; b) infusing the probe with a fluorogenic substrate specific for certain MMPs or group of MMPs; and c) measuring MMP activity of interstitial fluid contacted by the probe.

In the method and system, the measuring step can comprise measuring the fluorescence emitted by the fluorogenic substrate that has been cleaved by the MMP.

Thus, in one aspect, the method and system use on fluorogenic peptide substrates that exhibit intermolecular quenching. In these substrates, the peptide sequence separates a fluorescent donor group from an acceptor group that acts as a quencher of fluorescence. This phenomenon, in which excitation energy is transferred from an excited fluorescent donor to a quenching acceptor, is called resonance energy transfer. Cleavage of a peptide bond within the substrate leads to the separation of the donor-acceptor pair from the same molecule, thus allowing the increase of the fluorescence. The fluorescence increase is then proportional to the amount of peptide hydrolyzed. Several donor-acceptor pairs have been reported, including (i) o-aminobenzoic acid (Abz) as the donor and 2, 4 dinitrophenyl (Dnp) as the acceptor, (ii) 5-[(2'aminoethyl)-amino]naphtalenesulfonic acid (EDANS) as the donor and 4-[[4'-(dimethylamino)phenyl]azo]-benzoic acid (DABCYL) as the acceptor.

In the present method, the peptide substrates are specific for an MMP or a group of MMPs, such that the specific MMP (when present and active) cleaves the peptide between the fluorescent donor and the acceptor, thus producing a fluorescent signal.

In one aspect of the present method and system, the fluorogenic substrate is DNP-Pro-Leu-Gly-Leu-Trp-Ala-D-Arg-NH2 (SEQ ID NO:1) and the activities measured are those of MMP-1, 2, 3, 7 or 9.

In a further aspect of the present method and system, the fluorogenic substrate is DABCYL-GABA-Arg-Pro-Lys-Pro-Val-Glu-Nva-Trp-Arg-Glu(EDANS)-Ala-Lys-NH2 (SEQ ID NO:2) and the activities measured are those of MMP-3, 5, 9, 13.

In another aspect of the present method and system, the fluorogenic substrate is DNP-Pro-Leu-Ala-Leu-Trp-Arg-OH (SEQ ID NO:3) and the activity measured is that of MMP-1.

Still further, in one aspect of the present method and system, the fluorogenic substrate is DNP-Pro-Tyr-Ala-Tyr-Trp-Met-Arg-OH (SEQ ID NO:4) and the activity measured is that of MMP-3.

Still further, in one aspect of the present method and system, the fluorogenic substrate is DNP-Arg-Pro-Leu-Ala-Leu-Trp-Arg-Ser-OH (SEQ ID NO:5) and the activity measured is that of MMP-7.

Still further, in one aspect of the present method and system, the fluorogenic substrate is DNP-Pro-Leu-Ala-Tyr-Trp-Ala-Arg-OH (SEQ ID NO:6) and the activity measured is that of MMP-8.

Still further, in one aspect of the present method and system, the fluorogenic substrate is MCA-Pro-Cha-Gly-Nva-His-Ala-Dpa-NH2 (SEQ ID NO:7) and the activity measured is that of MMP-13.

Still further, in one aspect of the present method and system, the fluorogenic substrate is MCA-Pro-Leu-Ala-Cys(p-OMeBz)-Trp-Ala-Arg(Dpa)-NH2 (SEQ ID NO:8) and the activity measured is that of MMP-14.

Still further, in one aspect of the present method and system, the fluorogenic substrate is DNP-Pro-Leu-Gly-Met-Trp-Ser-Arg-OH (SEQ ID NO:9) and the activities measured are those of MMP-2, 9.

In another aspect of the present system and method, any combination of the described fluorogenic substrates can be used together to obtain real-time measurement of their respective MMPs in a single area to be assayed (e.g., an interstitial or extracellular space in the vicinity of the present microdialysis probe).

For example, the combination of substrates can be present in a single source (e.g., the infusate) to detect the respective MMP or group of MMPs that cleave the substrates. For example, the present method includes infusing a tissue, through the microdialysis probe, with one or more substrates selected from the group consisting of DNP-Pro-Leu-Gly-Leu-Trp-Ala-D-Arg-NH2 (SEQ ID NO:1), 1DABCYL-GABA-Arg-Pro-Lys-Pro-Val-Glu-Nva-Trp-Arg-Glu(EDANS)-Ala-Lys-NH2 (SEQ ID NO:2), DNP-Pro-Leu-Ala-Leu-Trp-Arg-OH (SEQ ID NO:3), DNP-Pro-Tyr-Ala-Tyr-Trp-Met-Arg-OH (SEQ ID NO:4), DNP-Arg-Pro-Leu-Ala-Leu-Trp-Arg-Ser-OH (SEQ ID NO:5), I DNP-Pro-Leu-Ala-Tyr-Trp-Ala-Arg-OH (SEQ ID NO:6), MCA-Pro-Cha-Gly-Nva-His-Ala-Dpa-NH2 (SEQ ID NO:7), MCA-Pro-Leu-Ala-Cys(p-OMeBz)-Trp-Ala-Arg(Dpa)-NH2 (SEQ ID NO:8) and DNP-Pro-Leu-Gly-Met-Trp-Ser-Arg-OH (SEQ ID NO:9). In this scenario, the activities measured are those of MMP-1, 2, 3, 7, 9 MMP-3, 5, 9, 13 or MMP-1 or MMP-3 or MMP-7 or MMP-8 or MMP-13 or MMP-14 or MMP-2, 9 depending on which combination of substrates is used. Table 3 shows the substrate specificity. In a further aspect, any sub combination of two or more substrates can be infused together, whether from a single source and single probe or from multiple probes supplied from multiple sources.

The uses of the present method and system reach as far as the presence of MMPs, since measurement in living intact tissue is accomplished by this method. The method is applicable in any tissue that can be reached with the microdialysis probe. With respect to clinical and research applications, the following are illustrative examples:

Application/Settings: Cardiovascular

Provided is a method of measuring MMP activity in real time in a subject with cardiovascular disease. Cardiovascular disease includes inter alia, ischemia reperfusion (I/R), hypertrophy, and heart failure.

Application/Settings: Cancer

Provided is a method of measuring MMP activity within the tumor to define the aggressive potential of the tumor. For example, a method of monitoring cancer therapy is provided, according to another aspect of the present invention, which includes administering cancer therapy to a subject having cancer. The cancer therapy causes death or injury of a tumor cell and the subsequent release of a compound from the dead or injured cell. The method further includes positioning a probe within the interstitium of the subject and infusing the interstitium, through the probe, with a fluorogenic substrate specific for the released compound. The method also includes receiving interstitial fluid, including the substrate, from the subject with the probe and detecting the received substrate to monitor the cancer therapy. In one aspect, the released compound is an MMP.

Application/Settings: Rheumatology/Inflammation

Provided is a method of measuring specific local levels of MMP activity in areas of inflammation. This method can be used to further define the nature of the inflammatory process.

For example, provided is a method of monitoring arthritis in a subject including positioning a probe within the joint fluid of the subject and infusing the joint fluid with a fluorogenic substrate specific for a compound of interest. The activity or presence of the compound is related to arthritis and the compound is located in the joint fluid. The substrate can be infused into the join fluid through the probe. The method can further comprise receiving interstitial fluid, including the substrate, from the subject with the probe and detecting the received substrate to monitor arthritis in the subject. The compound can be an MMP.

Application/Settings: Drug Discovery/Pharmacology

In all clinical settings, a rapid means by which to determine drug efficacy on a biological readout is highly desirable. Thus, a method for monitoring real time MMP activity during drug infusion is provided. Further, the present method and system provide for monitoring real time MMP activity with different therapeutic protocols.

In each of the above application settings, the systems and methods can be used to detect the activity of enzymes other than MMPs.

For example, a method of monitoring Aprotinin activity in a subject is provided, according to another aspect of the present invention. The method includes administering Aprotinin to the subject, positioning a probe within the interstitium of the subject, and infusing the interstitium of the subject with fluorogenic substrate specific for plasmin through the probe. The method further includes receiving interstitial fluid, including the substrate, from the subject with the probe. The method can also include detecting the received substrate to monitor Aprotinin activity in the subject.

A method is provided for detecting Aprotinin levels in a sample, according to another aspect of the present invention. The method can include contacting a sample suspected of having Aprotinin with a polypeptide comprising the sequence Ala-Leu-Lys-V', where V' is fluorophore that will not emit energy unless the bond between the Lys residue and the fluorophore is cleaved by a serine protease. The method can further comprise subjecting the sample to conditions suitable to allow Aprotinin to inhibit a serine protease inhibitor and detecting or measuring energy emitted by the donor fluorophore, where the presence or amount of the energy indicates the presence or amount of Aprotinin in the sample.

Also provided are methods of monitoring a modification in a biological process in a subject. Such a modification can be caused by a pharmacological agent. For example, a pharmacological agent can be administered to the subject to affect a modification of the biological process therein the subject. The subject's interstitium can be infused with a fluorogenic substrate. Within the interstitial fluid at least a portion of the fluorogenic substrate in can be altered. An alteration includes any change to the substrate that can increase the fluorescent signal or potential of the substrate or that can decrease the fluorescent signal or potential. Altered substrate can be received with interstitial fluid from the subject such that the received interstitial fluid comprises altered substrate. The altered substrate can be detected to monitor the modification of the biological process.

The biological process can be any type of enzymatic activity, for example, caused by one enzyme or a plurality of enzymes, for example as in a multiple enzyme signaling loop or process. In some aspects, the compound monitored is not an enzyme, but can alter the substrate to increase or decrease the fluorescence. Thus, the process can include any single or multiple component biological process in a subject. In one example, the biological process can be cellular death or injury. Cellular death or injury is a biological process that can release compounds into the interstitial fluid. In one aspect, the released compounds, including enzymes, can be monitored by the described systems and methods.

In some aspects, an increase in detected altered fluorogenic substrate can indicate the modification of the biological process by the administered agent. For example, a dead or dying cancer cell, caused by administration a chemotherapeutic agent or radiation, can cause increased release of compounds that can alter the substrate and thereby cause increased fluorescence in a sample that can be detected. Thus, cancer therapy, including chemotherapy or irradiation can be monitored in real-time using the described methods and systems.

In other aspects, a decrease in detected altered fluorogenic substrate can indicate the modification of the biological process by the administered agent. In these aspects, the administered pharmacological agent can act to inhibit the biological process and to thereby decrease the amount of detectable altered fluorogenic substrate. Thus, the described systems and method can be used to monitor inhibition of biological processes or portions thereof by pharmacological agents. For example, the enzymatic inhibitory activity of Aprotinin can be measured and monitored. In some aspects, the detectable state of the altered substrate is detected in real-time to indicate the modification of the biological process by the administered agent in real-time. Any type of detectable substrate, for example fluorescent or luminescent, that can be altered into a detectable state can be used.

Moreover, multiple substrates can be used in combination, wherein any combination of alterations can be used. In these aspects, the substrates can be specific for distinct biological processes that can be modified by distinct pharmacological agents.

In yet another aspect of the present invention, a composition is provided that comprises a synovial fluid and a fluorogenic substrate. In one aspect, the fluorogenic substrate can be modified into a detectable state by interaction with an enzyme located in the synovial fluid. Optionally, the fluorogenic substrate can be modified into a detectable state by interaction with a protein located in the synovial fluid. In yet another aspect, the fluorogenic substrate can be modified into a detectable state by interaction with a protein, enzyme, peptide, polypeptide, or nucleic acid located in the synovial fluid.

A composition is provided, according to yet another aspect of the present invention, which comprises a non-cardiac interstitial fluid and a fluorogenic substrate.

EXPERIMENTAL

The following examples are put forth so as to provide those of ordinary skill in the art with a complete disclosure and description of how the apparatuses, systems and/or methods claimed herein are made and evaluated, and are intended to be purely exemplary of the invention and are not intended to limit the scope of what the inventors regard as their invention. Efforts have been made to ensure accuracy with respect to numbers (e.g., frequency measurements, etc.), but some errors and deviations should be accounted for.

Example 1

Sterilization of System Components

In order to apply the above-described systems and methods in clinical applications, techniques and validation studies were used to develop a sterilization procedure for the microdialysis probe, tubing and connectors, and the fluorogenic substrate. Several considerations were taken into account: (1) the components were packaged in a way that was compatible with the sterilization procedure; (2) the packages were amenable to conventional surgical and labeling procedures; (3) the packaging were easily dispensable onto the operating table in a sterile manner and conforming to sterility practice guidelines; (4) the sterilization procedure meets all infection control and hospital quality assurance program guidelines; and (5) the sterilization procedure does not alter the performance characteristics of the microdialysis probe, tubing and connectors, or substrate.

The initial sterilization procedures entailed ethylene oxide sterilization using a conventional 15 minute gas/30 minute evacuation procedure. Through a stepwise set of studies, the gas time and evacuation time were increased. At each step, full tests on the performance characteristics of the microdialysis probe (cut off integrity, fluidics flow, microscopic study of membrane) were performed. The substrate was prepared in a lyophilized form and placed into sterilizable ampules. Following the sterilization cycle, the substrate was reconstituted with fluorescence characteristics determined (background emission, stability at 37° C. for up to 4 hours). In addition, complete calibration curves with known recombinant protein standards were performed at each sterilization cycle. If changes in fluorescence characteristics or calibration curve exceeded a variance of 10%, then revisions in the sterilization process were performed.

If the ethylene oxide sterilization procedure achieved adequate performance characteristics, then full quality control testing of the components was performed. This entailed full bacterial and fungal microbiology testing. The microdialysis probe was sectioned into six equivalent parts and plated in four different culture media to enhance bacterial/fungal growth. The plates were analyzed at 24-hour intervals for up to 28 days. Satisfactory sterilization was defined as no growth on any cultures for the 28-day period. While these sterilization tests were satisfactory, concerns remained about access of the ethylene oxide into the microdialysis membrane and substrate. Furthermore, storage and shelf life of the components may not be stable. Accordingly, a more rigorous sterilization method was developed.

For this process, the probes and tubing were placed in a sterilizable and disposable plastic case containing a labeling platform. The case was then sealed in sterile pouches and processed by gamma irradiation. A dosimetry record was maintained for each sterilized case and was processed by Steris Isomedix Services. These sterilized cases were contained within a sterilized packaging providing for double barrier protection. The dose of radiation was greater than 40 kGy. Sterilization records, dosimetry profiles, and lot number were maintained on each microdialysis package.

Through extensive validation testing and sterilization testing, as described above, this approach provided for optimal sterility and performance characteristics with a long shelf life (>6 months). The sterile case can be placed on the operating table and allow for easy access and assembly of the components. The microdialysis probe, tubing, connectors, microsyringe and substrate ampule can all be disposable. Thus, this platform provided for a sterilized, pre-packaged, disposable format.

Example 2

Algorithm for Computation of In Vivo Aprotinin Concentration

Figure 12:
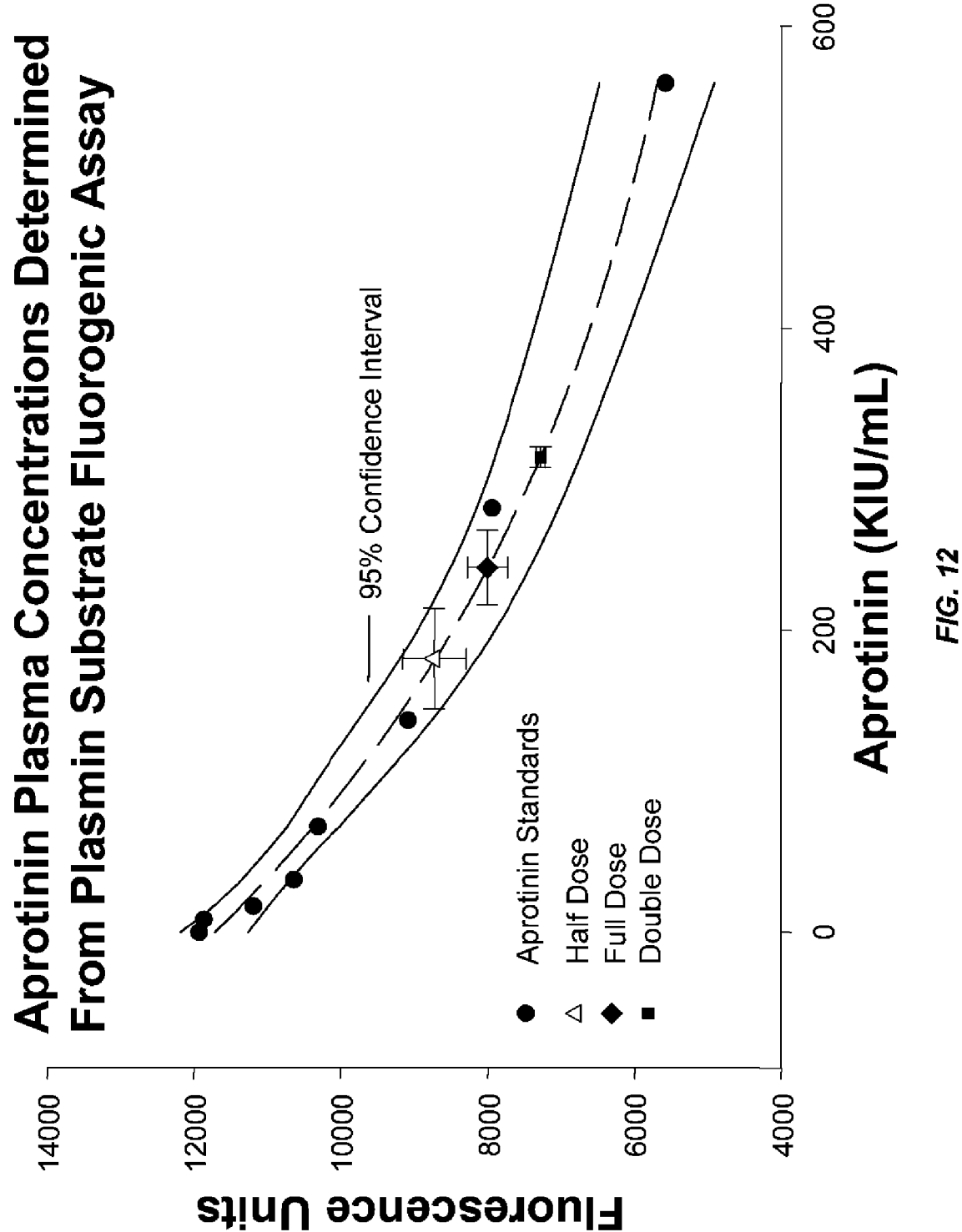
FIG. 12 is a graphical illustration showing Aprotinin plasma concentrations determined from a plasmin substrate fluorogenic assay.

A standardized algorithm for the computation of an in vivo aprotinin concentration was developed. A fluorogenic peptide construct was used, which can be cleaved by active plasmin. Using this peptide, actual concentrations of the serine protease inhibitor, aprotinin, were determined. For these studies, mice were systemically administered aprotinin at half (n=5), full (n=5), or double the computed Hammersmith dosing regimen. The dosing regimen is empirically based upon body weight and is what is currently used clinically. After 30 minutes of the aprotinin administration, blood samples were collected and incubated in the plasmin fluorogenic substrate and then the samples were subjected to fluorometric measurements. The fluorometric measurements from the plasma samples were plotted on the calibrated and validated curve for known concentrations of aprotinin. For the calibration, normal murine plasma was incubated with the plasmin substrate in the presence and absence of fixed concentrations of aprotinin. The standard curve is shown in FIG. 12 along with the 95% confidence interval. The intra-assay coefficient of variation was 5% and the inter-assay coefficient of variation was 6%. The mean fluorescence values and the mean computed aprotinin concentrations for each cohort of dosing cohorts were superimposed on the calibration curve.

Thus, a standardized algorithm was developed that allows for the computation of an in vivo aprotinin concentration. Coupling this validated fluorogenic system with microdialysis, as described herein enables a continuous, real time assessment of aprotinin levels within specific tissue compartments. This can be applied to the clinical context of cardiovascular surgery where aprotinin is commonly administered.

Example 3

In Vitro MMP Substrate Validation

An in vitro method was utilized to test and validate fluorogenic substrates by utilizing recombinant MMP standards and MMP inhibitors. A list of substrates that are commercially available with accompanying references are shown below:

TABLE 3

| Construct | SEQ ID NO: | Specificity |
|---|---|---|
| DNP-Pro-Leu-Gly-Leu-Trp-Ala-D-Arg-NH$_2$ | SEQ ID NO: 1 | MMP-1,2,3,7,9 |
| DABCYL-GABA-Arg-Pro-Lys-Pro-Val-Glu-Nva-Trp-Arg-Glu(EDANS)-Ala-Lys-NH$_2$ | SEQ ID NO: 2 | MMP-3,5,9,13 |
| DNP-Pro-Leu-Ala-Leu-Trp-Arg-OH | SEQ ID NO: 3 | MMP-1 |
| DNP-Pro-Tyr-Ala-Tyr-Trp-Met-Arg-OH | SEQ ID NO: 4 | MMP-3 |
| DNP-Arg-Pro-Leu-Ala-Leu-Trp-Arg-Ser-OH | SEQ ID NO: 5 | MMP-7 |
| DNP-Pro-Leu-Ala-Tyr-Trp-Ala-Arg-OH | SEQ ID NO: 6 | MMP-8 |

TABLE 3-continued

| Construct | SEQ ID NO: | Specificity |
| --- | --- | --- |
| MCA-Pro-Cha-Gly-Nva-His-Ala-Dpa-NH$_2$ | SEQ ID NO: 7 | MMP-13 |
| MCA-Pro-Leu-Ala-Cys(p-OMeBz)-Trp-Ala-Arg(Dpa)-NH$_2$ | SEQ ID NO: 8 | MMP-14 |
| DNP-Pro-Leu-Gly-Met-Trp-Ser-Arg-OH | SEQ ID NO: 9 | MMP-2,9 |

Figure 13:
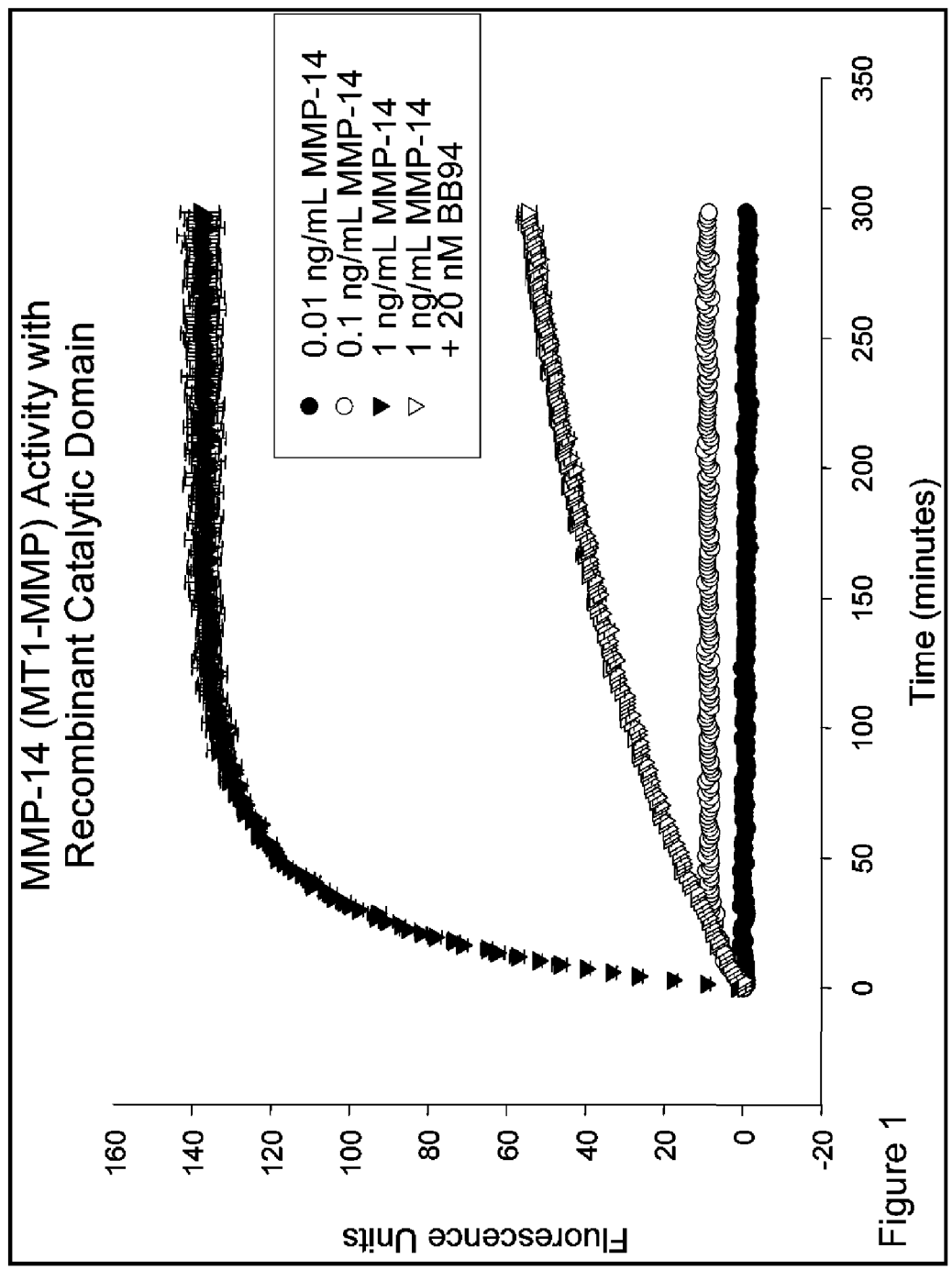
FIG. 13 is a graphical illustration showing a concentration dependent increase in fluorescence emission due to increasing concentration of MT1-MMP (MMP-14) recombinant catalytic domain.

Nva = L-norvaline
Dpa = 3-(2,4-dinitrophenyl)-L-2,3-diaminopropionyl
MCA = (7-methoxycoumarin-4-yl)acetyl
p-OmeBz = S-para-methoxybenzyl In Vitro Validation Results Examples of fluorogenic substrate specificity for MMPs are shown below. FIG. 13 shows a concentration dependent increase in fluorescence emission due to increasing concentration of MT1-MMP (MMP-14) recombinant catalytic domain. With the addition of BB94, a global MMP inhibitor, there is an abolishment of fluorescence emission.

Figure 14:
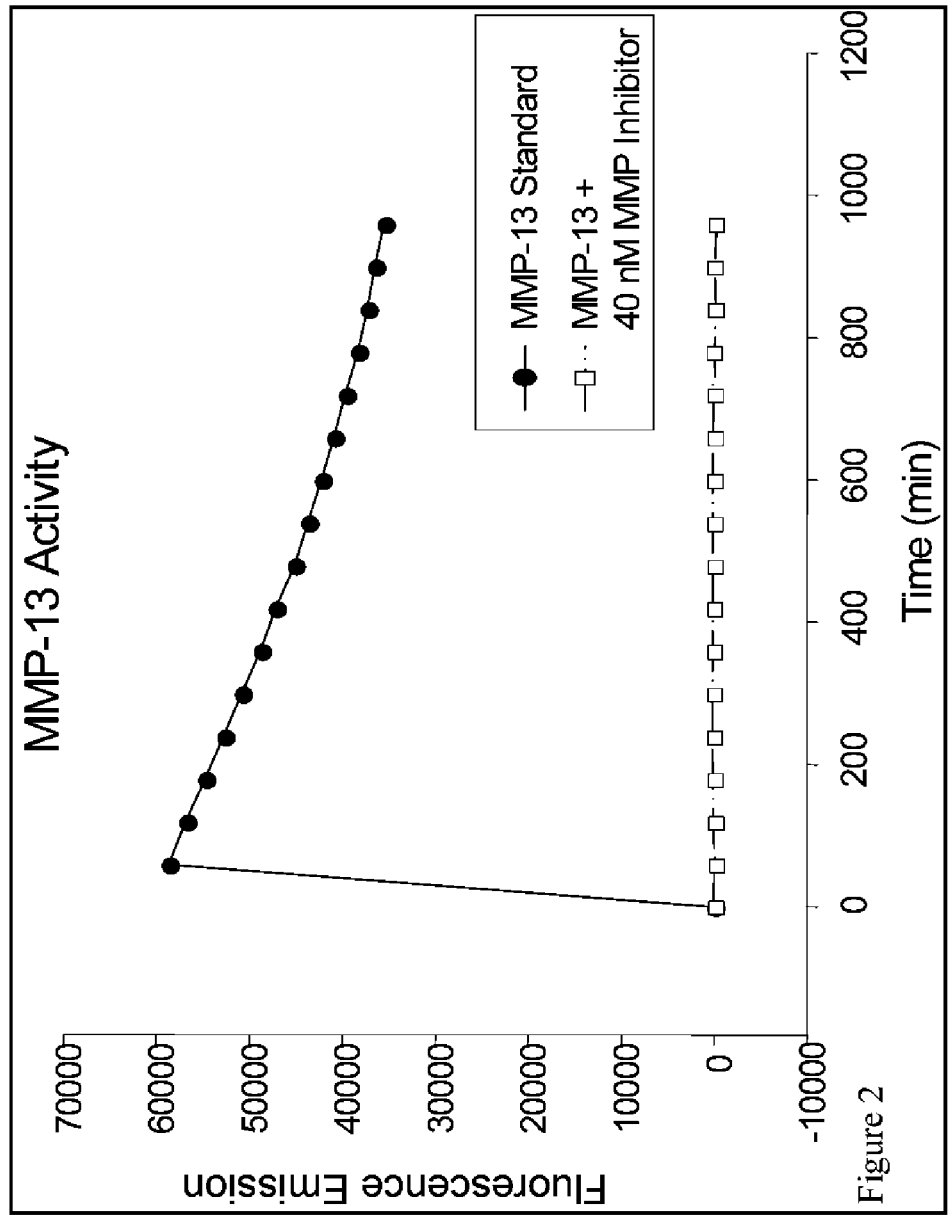
FIG. 14 is a graphical illustration showing that MMP-13 recombinant protein caused an increase in fluorescence emission that was abolished with the addition of BB94.

FIG. 14 shows that MMP-13 recombinant protein caused an increase in fluorescence emission that was abolished with the addition of BB94.

Figure 15:
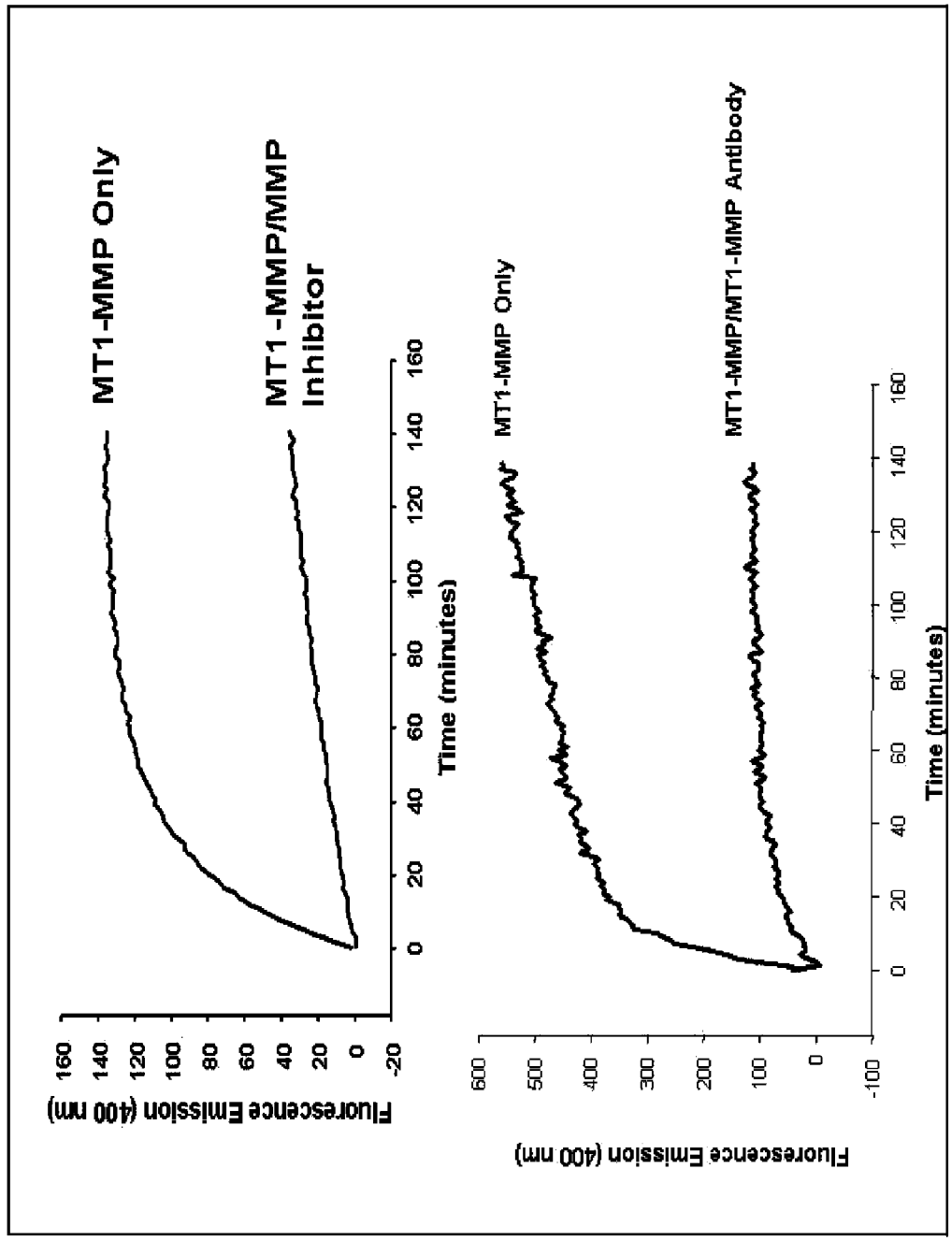
FIG. 15 is a graphical illustration showing that incubation with a broad-spectrum MMP inhibitor reduced fluorescence emission.

Several other in vitro validation studies were performed on the MT1-MMP specific fluorogenic substrate (30 mM, MCA-Pro-Leu-Ala-Cys(p-OmeBz)-Trp-Ala-Arg(Dpa)-NH2 (SEQ ID NO:8), Calbiochem) in order to demonstrate the specificity of the MT1-MMP substrate. Specifically, MT1-MMP substrate (7.5 mM) was injected into a 96-well polystyrene plate (Nalge Nunc International, Rochester, N.Y.) with a 1.0 ng/mL concentration of recombinant MT1-MMP catalytic domain (BIOMOL, Plymouth Meeting, Pa.) and fluorescence emission was recorded. A rapid rise in activity, as measured by fluorescence emission, plateaued around 90 minutes. Incubation with a broad-spectrum MMP inhibitor reduced fluorescence emission. (FIG. 15, top). In addition, full length MT1-MMP (pretreated with 10 mM p-aminophenylmercuric acetate) was incubated for 1 hour at 37° C. with or without an antibody specific for the catalytic domain of MT1-MMP (1000 ng/mL, Chemicon AB8102). After the incubation period, the MT1-MMP substrate was injected and fluorescence emission recorded. (FIG. 15, bottom) Co-incubation with the MT1-MMP antibody extinguished fluorescence emission.

Figure 16:
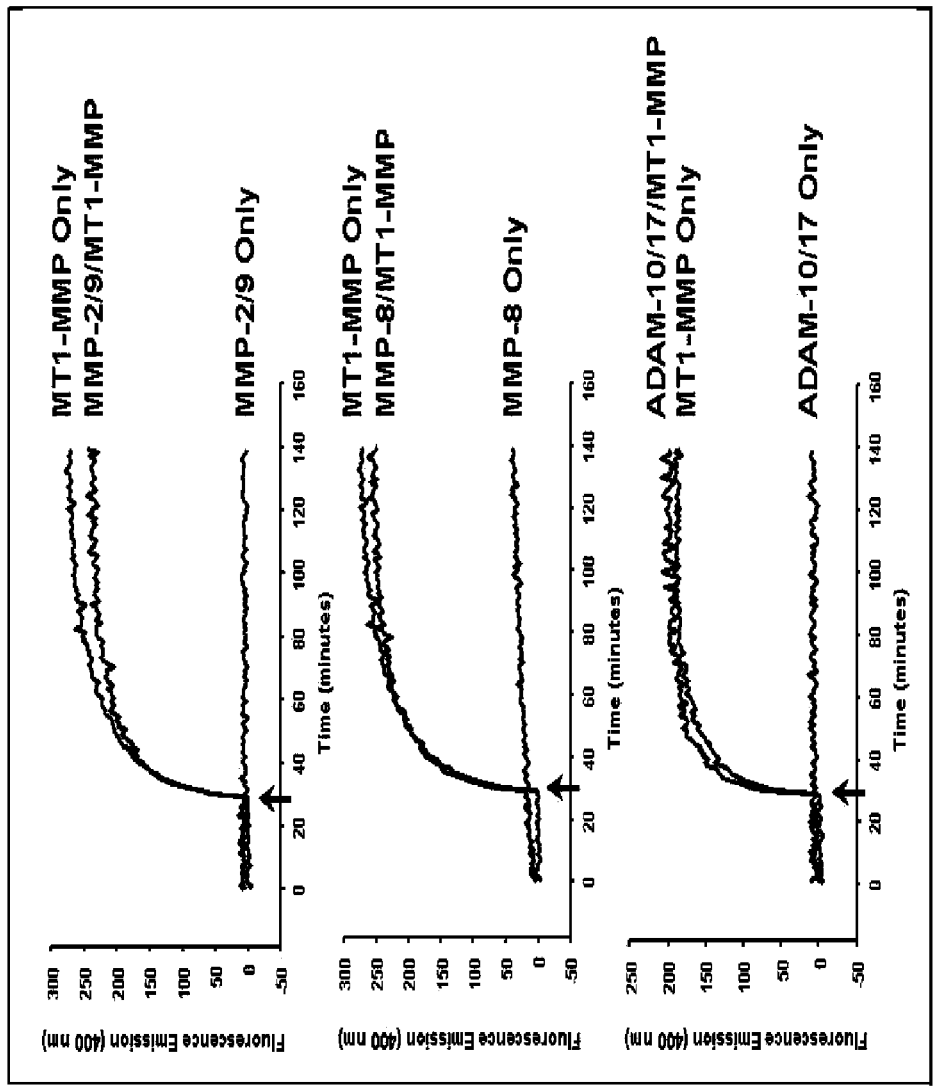
FIG. 16 is a graphical illustration showing results of injection of MT1-MMP catalytic domain (1000 ng/mL, BIOMOL, Plymouth Meeting, Pa.) into a 96-well polystyrene plate (Nalge Nunc International, Rochester, N.Y.) with a 30 μM mixture of MT1-MMP substrate only or MT1-MMP substrate with MMP-2/9 (500 ng/mL, Chemicon.

In an additional set of experiments (FIG. 16), MT1-MMP catalytic domain (1000 ng/mL, BIOMOL, Plymouth Meeting, Pa.) was injected into a 96-well polystyrene plate (Nalge Nunc International, Rochester, N.Y.) with a 30 mM mixture of MT1-MMP substrate only or MT1-MMP substrate with MMP-2/9 (500 ng/mL, Chemicon; FIG. 16, top), MMP-8 (10 ng/mL, Calbiochem; FIG. 16, middle), or a disintegrin and metalloproteinase (ADAM)-10 and -17 cocktail (200 ng/mL, R&D Systems; FIG. 16, bottom). Incubation with MMP-2/9, MMP-8, or ADAM-10 and 17 alone failed to cause fluorescence emission from the MT1-MMP substrate. However, injection of the MT1-MMP catalytic domain resulted in a rapid rise in fluorescence emission in all protease cocktails. Therefore, these in vitro assays demonstrate the relative specificity of the MT1-MMP substrate with respect to other MMP types and proteases such as ADAMs.

Figure 17:
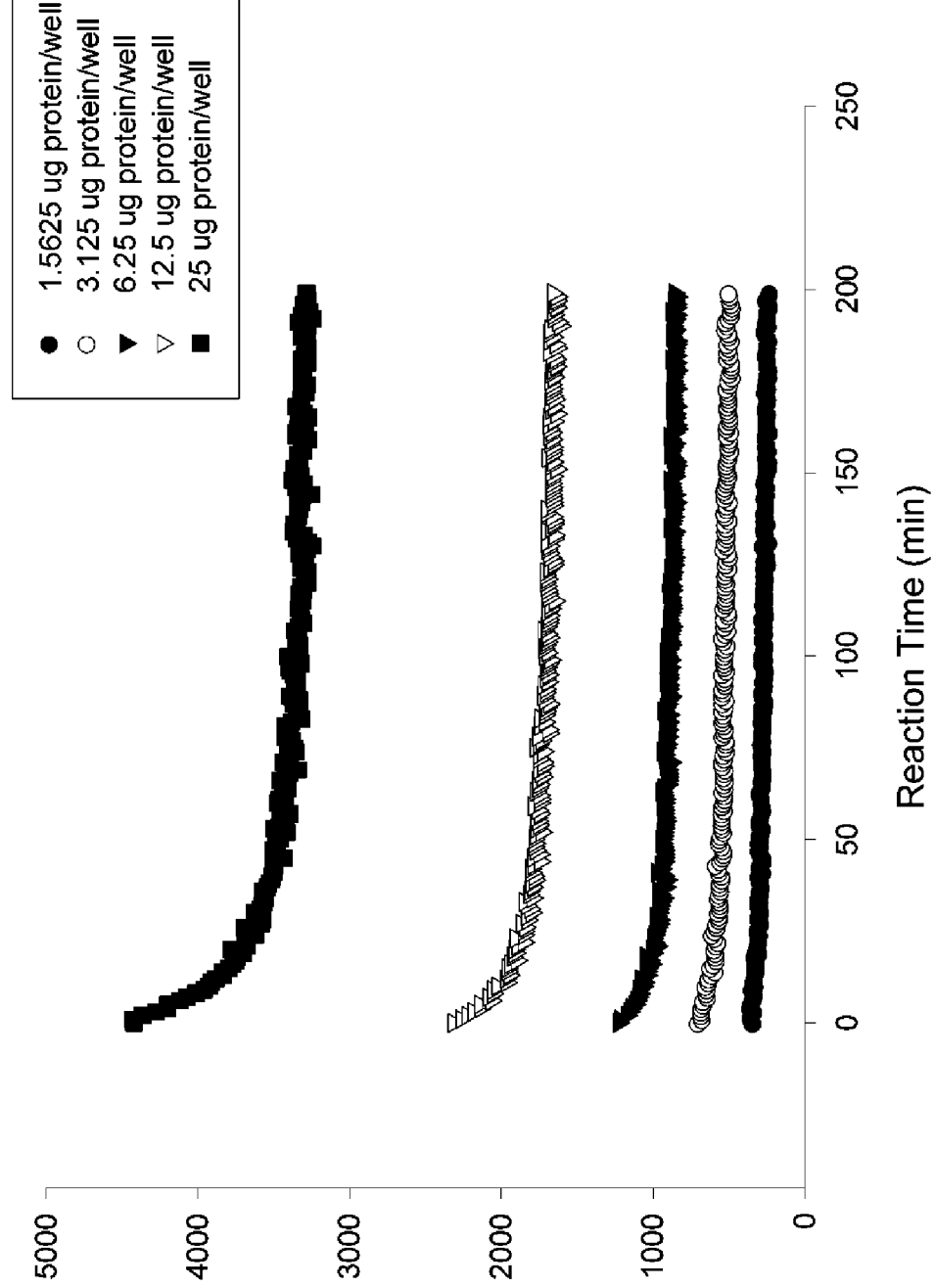
FIG. 17 is a graphical illustration showing a protein dependent increase in MMP-1, 2, 3, 7, 9 activity demonstrated in human myocardial extracts.

In addition, these substrates were used to examine MMP activity ex-vivo using myocardial samples from both human and animal specimens. The frozen myocardial tissue was submerged in 2 mL of ice-cold buffer (Cacodylic Acid, NaCl, ZnCl2, CaCl2, NaN3, 0.08% Triton X), homogenized, and spun at 8,000 G for 10 minutes at 4C. The supernatant was then measured, tested for protein concentration, aliquoted, and stored at −70° C. Final protein concentrations were diluted in a reaction buffer containing (0.05% Brij, 50 mM Tris-HCl, 0.2 M NaCl, 10 mM CaCl2, 50 mM ZnCl2) and the samples were loaded onto a 96-well microplate (Fluoro-Nunc® 96-Well Polystyrene Plates) and placed in a 37° C. temperature controlled unit allowing for continuous fluorescence measurements (FLUOstar® Galaxy, BMG Labtechnologies). Substrate (MMP Substrate, Fluorogenic, Calbiochem) was diluted in the same reaction buffer and loaded into the FLUOstar® for automatic injection (12 mM). The generic structure of this substrate is DNP-Pro-Leu-Gly-Leu-Trp-Ala-D-Arg-NH2 (SEQ ID NO:1) and has been demonstrated previously by in-vitro biochemical analysis to be cleaved selectively by MMPs 1, 2, 3, 7, 9. Excitation was set to (280 nm) and emission was set to (360 nm) and readings were taken every 2 minutes following the addition of the substrate. The reaction was allowed to proceed to 200 recordings (398 minutes). This reaction using the MMP-1, 2, 3, 7, 9 specific substrate was linear with increasing concentrations. A protein dependent increase in MMP-1, 2, 3, 7, 9 activity could be demonstrated in human myocardial extracts (FIG. 17).

Figure 18:
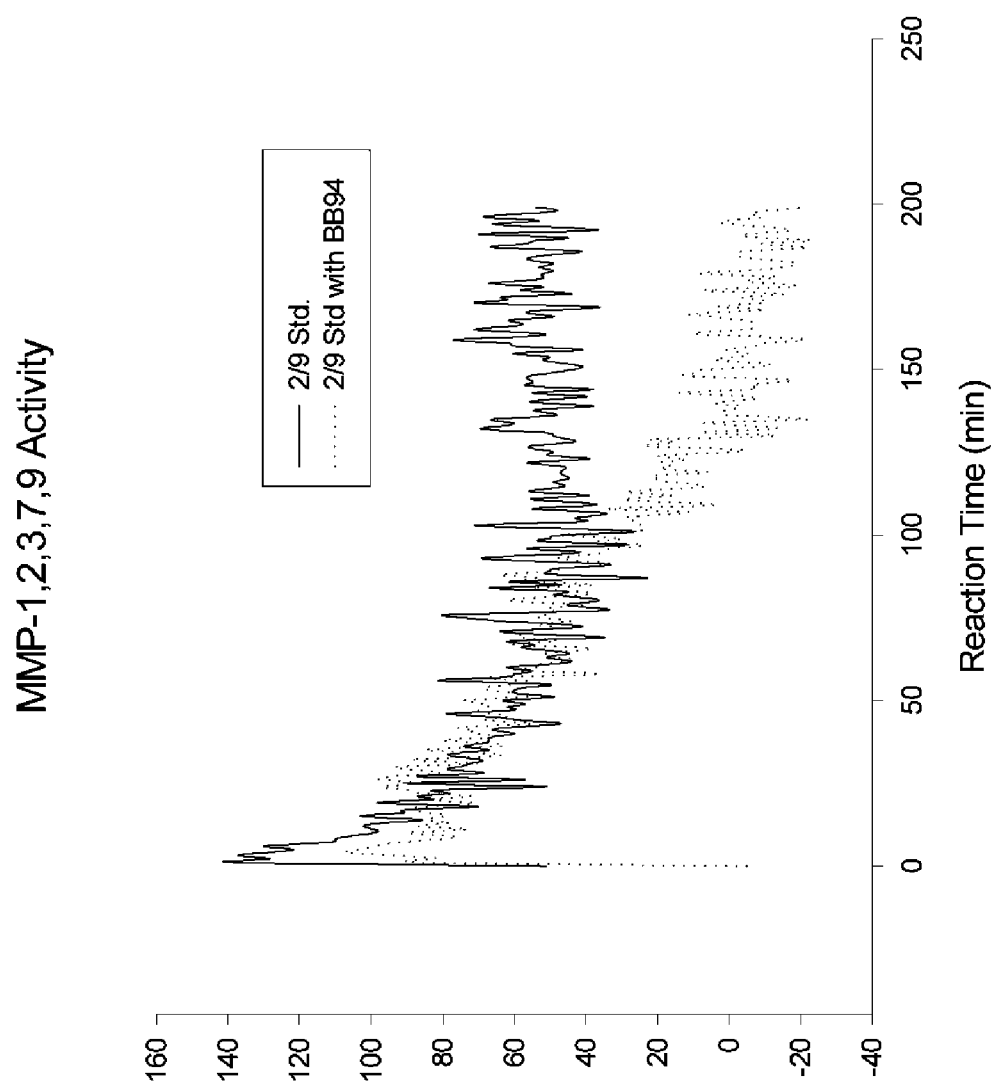
FIG. 18 is a graphical illustration showing results of inhibition with the MMP selective inhibitor (BB94, 10 mM).

In addition, this reaction could be significantly inhibited with the MMP selective inhibitor (BB94, 10 mM) (FIG. 18).

Figure 19:
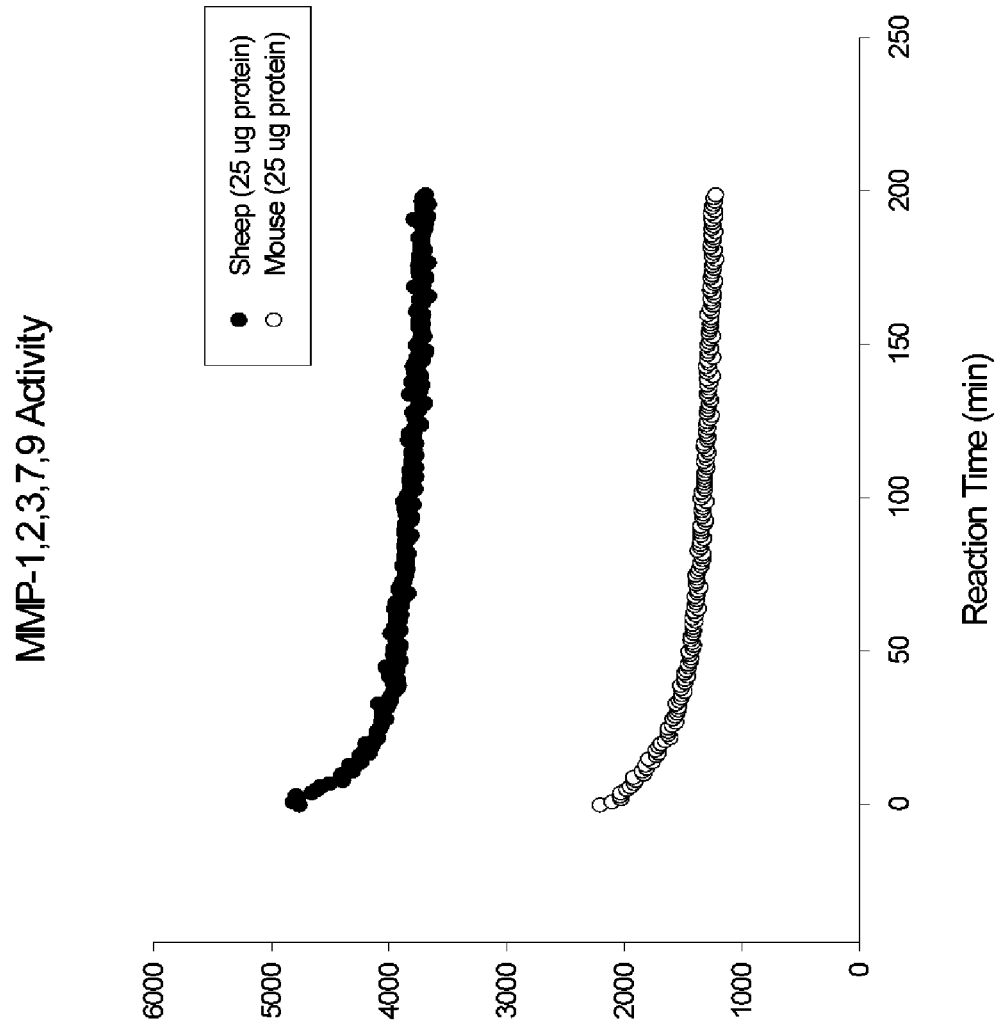
FIG. 19 is a graphical illustration showing that MMP-1, 2, 3, 7, 9 myocardial activity could be detected in sheep and mouse myocardial samples.

MMP-1, 2, 3, 7, 9 myocardial activity could be detected in sheep and mouse myocardial samples as shown in (FIG. 19).

Thus, a selective and sensitive method for directly measuring MMP-1, 2, 3, 7, 9 myocardial ex-vivo activity was developed. This method allows for measurement of MMP-1, 2, 3, 7, 9 activity in crude myocardial homogenates and therefore provides an index of actual MMP-1, 2, 3, 7, 9 activity in the presence of endogenous MMP inhibitors such as TIMPs. This is desirable since measuring relative MMP-1, 2, 3, 7, 9 protein abundance in purified and detergent treated samples does not indicate the proteolytic activity of these MMPs.

Figure 20:
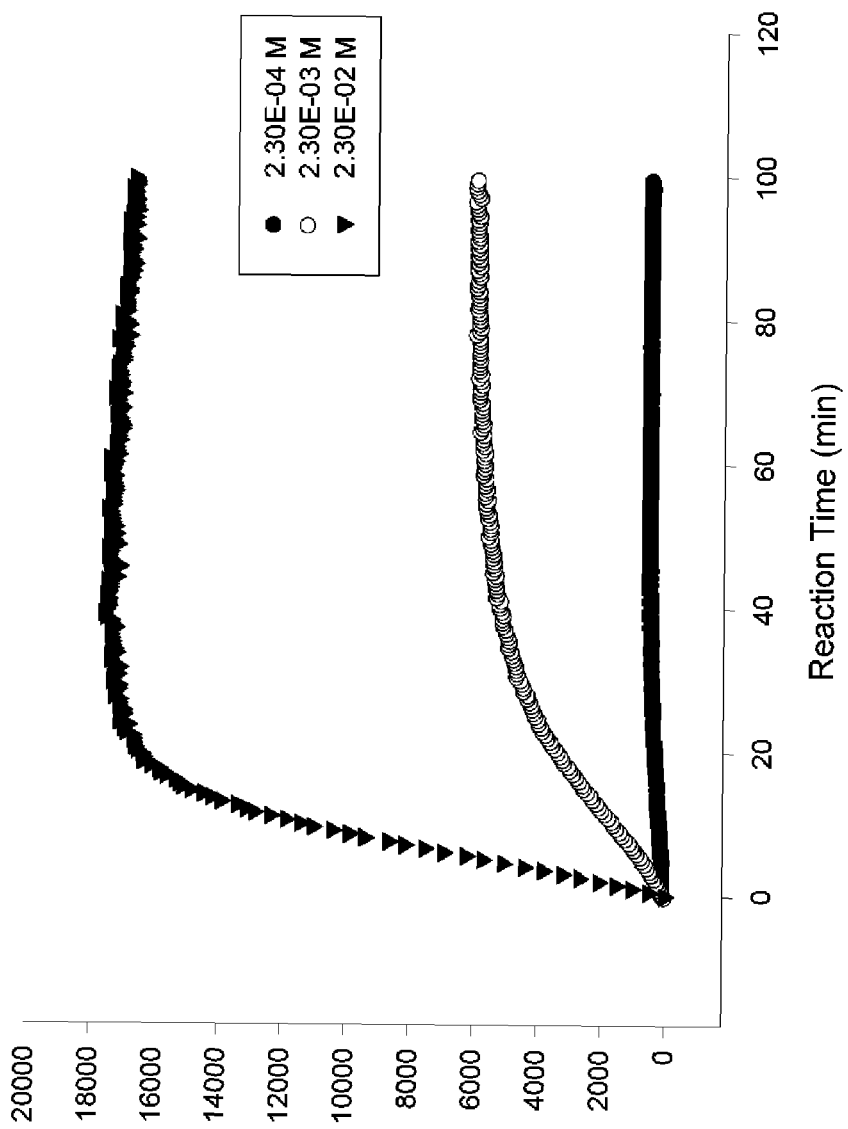
FIG. 20 is a graphical illustration showing that a reaction using the MMP-14 specific substrate was linear with increasing concentrations of a recombinant MMP-14 catalytic domain (2.3 E-2-2.3 E-4 M, Chemicon).

A similar experiment was done utilizing the fluorogenic substrate specific for MT1-MMP (MMP-14). Substrate (MMP-14 Substrate I, Fluorogenic, Calbiochem) was diluted in the same reaction buffer and loaded into the FLUOstar® for automatic injection (10 µM). The generic structure of this substrate is MCA-Pro-Leu-Ala-Cys(p-OmeBz)-Trp-Ala-Arg(Dpa)-NH2 (SEQ ID NO:8) and has been demonstrated previously by in-vitro biochemical analysis to be cleaved selectively by MMP-14.1 Excitation was set to (330 nm) and emission was set to (405 nm) and readings were taken every 2 minutes following the addition of the substrate. The reaction was allowed to proceed in which 200 recordings (398 minutes) were collected. This reaction using the MMP-14 specific substrate was linear with increasing concentrations of a recombinant MMP-14 catalytic domain (2.3 E-2-2.3 E-4 M, Chemicon) (FIG. 20).

Figure 21:
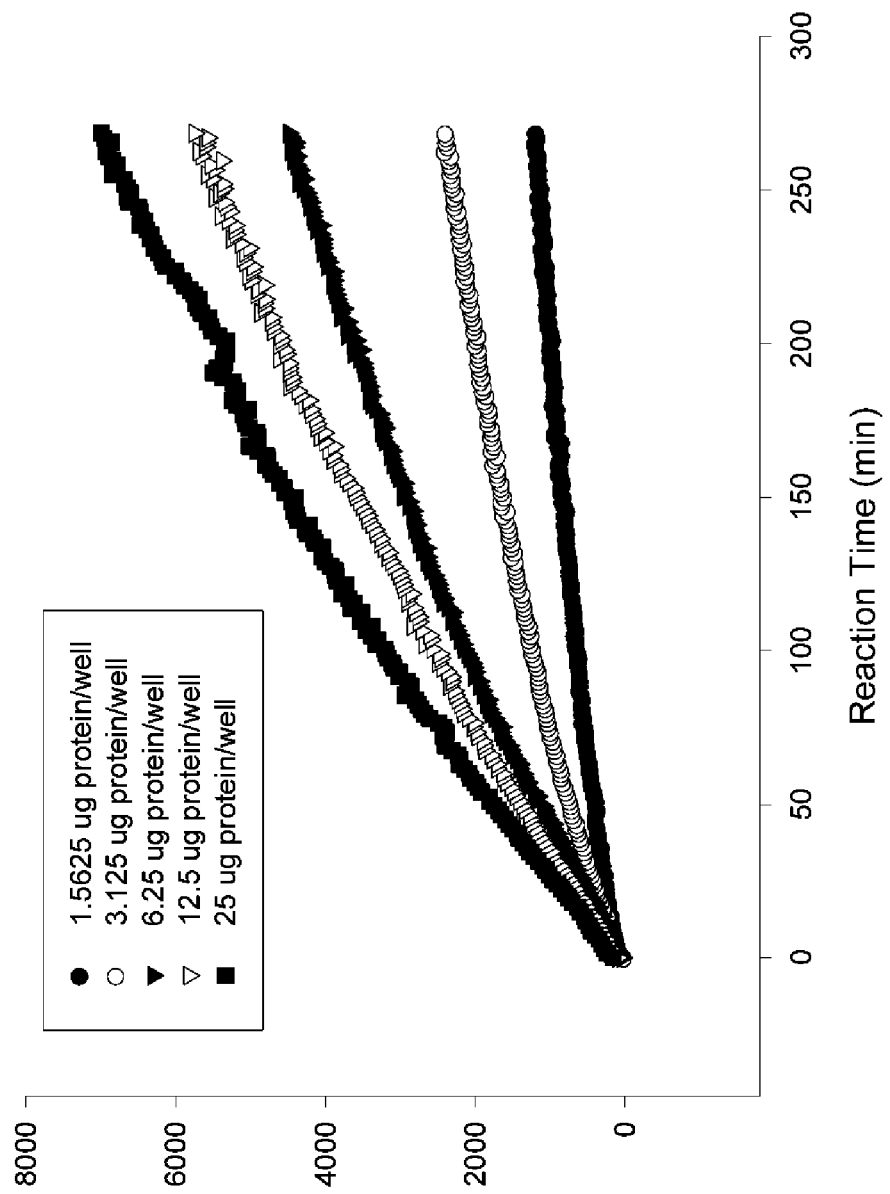
FIG. 21 is a graphical illustration showing a protein dependent increase in MMP-14 activity demonstrated in human myocardial extracts.

A protein dependent increase in MMP-14 activity could be demonstrated in human myocardial extracts (FIG. 21).

Figure 22:
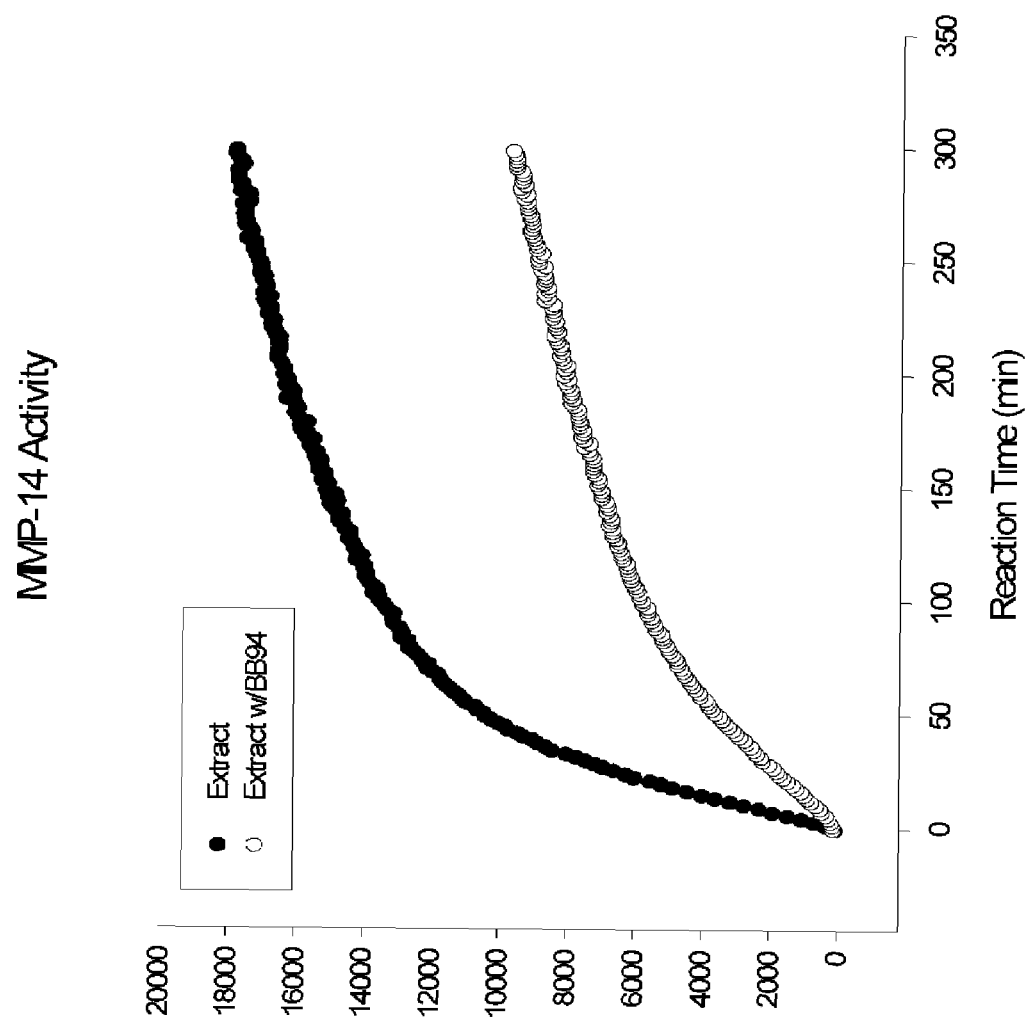
FIG. 22 is a graphical illustration showing inhibition with the MMP selective inhibitor (BB94, 10 mM).

In addition, this reaction could be significantly inhibited with the MMP selective inhibitor (BB94, 10 mM) (FIG. 22).

Figure 23:
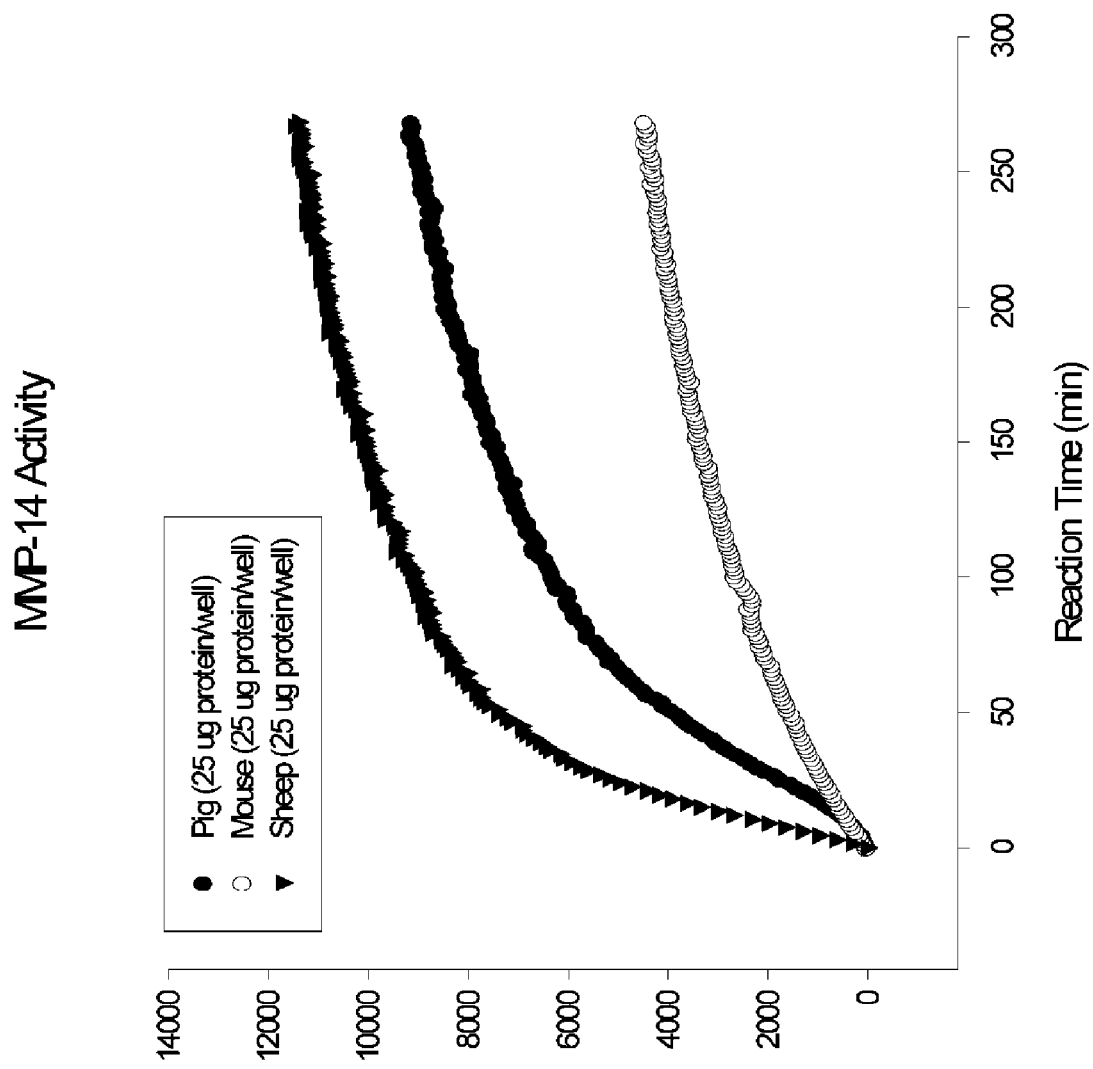
FIG. 23 is a graphical illustration showing MMP-14 myocardial activity detected in porcine, sheep and mouse myocardial samples.

MMP-14 myocardial activity could be detected in porcine, sheep and mouse myocardial samples as shown in (FIG. 23).

Thus, a selective and sensitive method for directly measuring MMP-14 myocardial ex-vivo activity was developed. This method allows for measurement of MMP-14 activity in crude myocardial homogenates and therefore provides an index of actual MMP-14 activity in the presence of endogenous MMP inhibitors such as TIMPs. This is an important advance since measuring relative MMP-14 protein abundance in purified and detergent treated samples does not indicate the proteolytic activity of this membrane bound MMP. This fluorogenic assay provides a means by which to directly determine MMP-14 activity that may be operative at the sarcolemmal-interstitial interface.

Example 4

Method and System for Real Time In Vivo Measurement of MMP Activity in Pigs and Humans A 4 mm-long membrane (20 kDa; outer diameter of probe shaft, 0.77 mm; outer diameter of probe membrane, 0.5 mm; CMA/Microdialysis, North Chelmsford, Mass.) was inserted in the left ventricular apical midmyocardium. The inlet tube of the probe was connected to a 23G×1" aluminum hub blunt needle (Tyco Healthcare Group, Mansfield, Mass.) connected to a 3 mL BD Luer-Lok™ disposable syringe with BD Luer-Lok™ tip (BD, Franklin Lakes, N.J.) by 0.65 mm OD×0.12 mm ID PEEK blue tubing (Bioanalytical Systems, Inc., West Lafayette, Ind.). The syringe was housed in a Baby Bee Syringe Drive and controlled by the MD-1020 Bee Hive Controller (Bioanalytical Systems, Inc., West Lafayette, Ind.). The MMP substrate specific for MMP-2/9 (Calbiochem, La Jolla, Calif.) at a concentration of 60 mM was loaded into the syringe which is covered in aluminum foil (to protect from the light). The substrate is infused at a rate of 5 mL/minute. The outlet tube of the probe was connected to the PEEK tubing.

Figure 24:
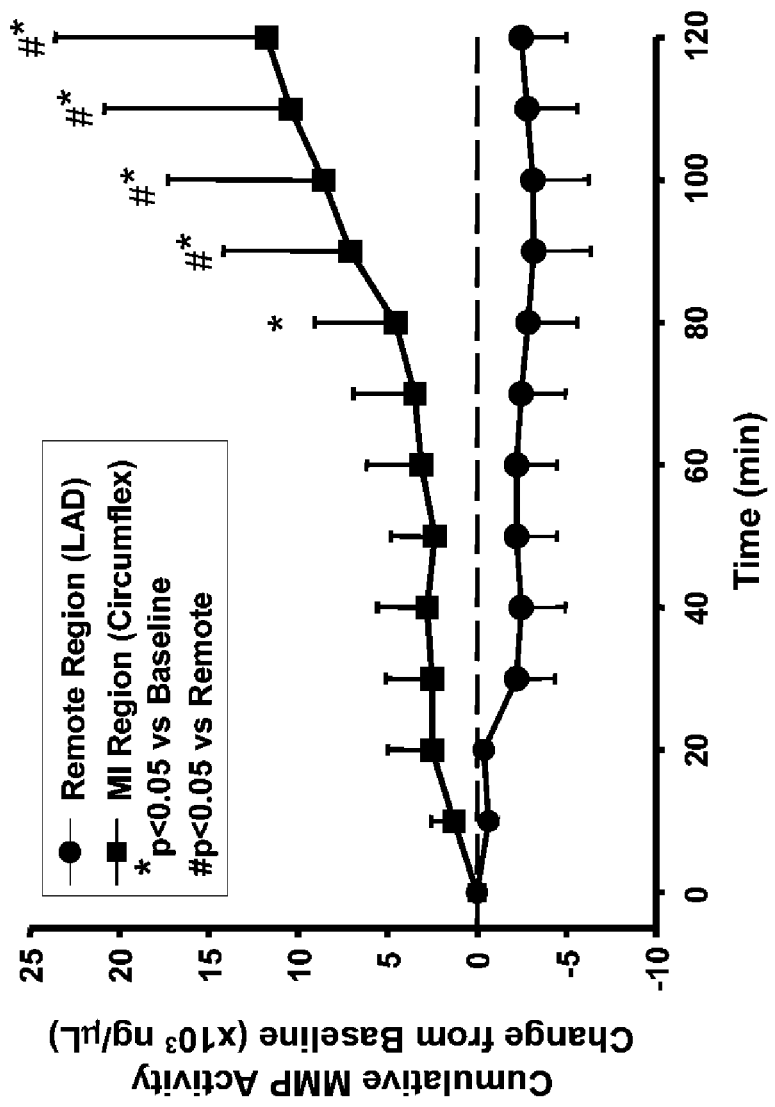
FIG. 24 is a graphical illustration showing measurement of MMP activity in porcine myocardium during ischemia.
Figure 25:
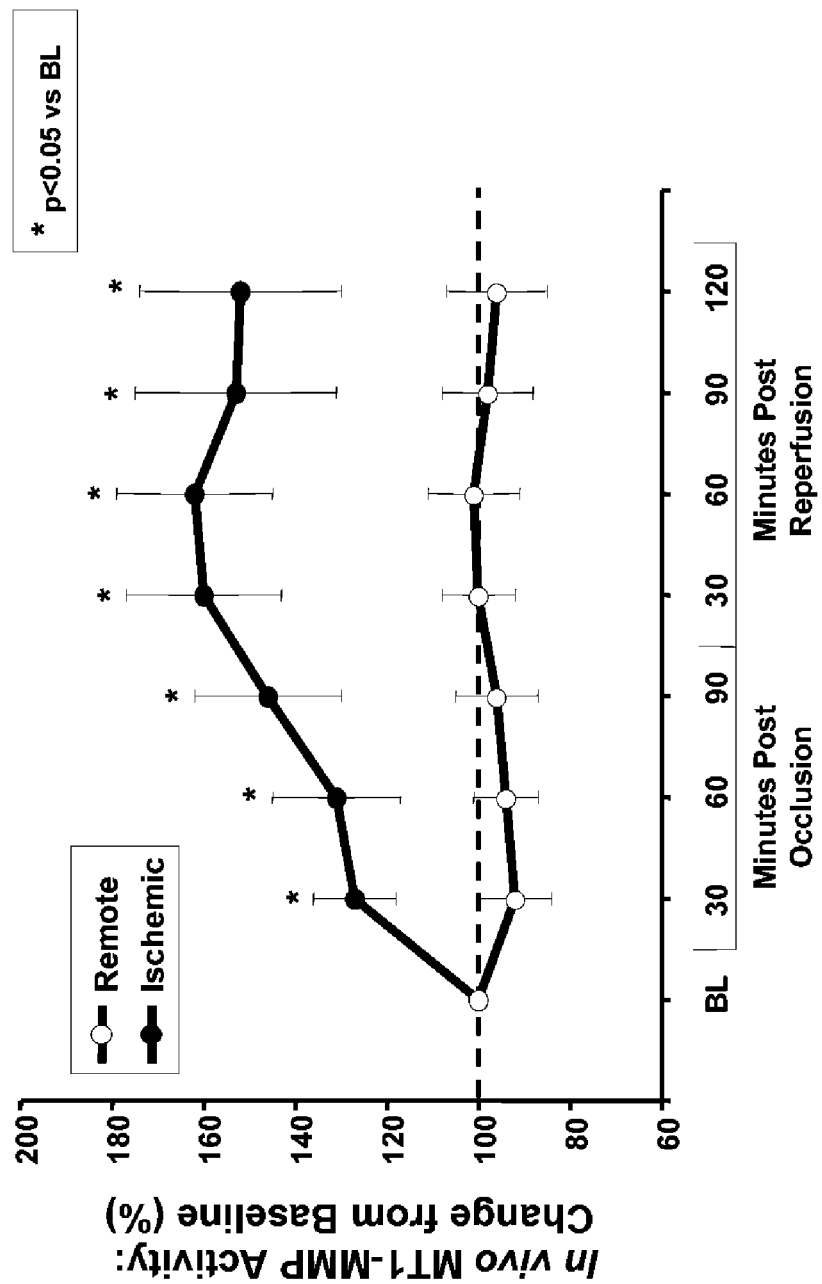
FIG. 25 is a graphical illustration showing MT1-MMP activity measured by utilizing substrate for MT1-MMP.

This technique was utilized to measure MMP activity in porcine myocardium during ischemia as shown in FIG. 24. It was discovered that cumulative MMP activity is significantly increased after 80 minutes of ischemia in the ischemic region of the myocardium. In the normally perfused myocardium, there is no increase in MMP activity. In a second study, selective MMP activity was measured by utilizing the substrate for MT1-MMP FIG. 25. Here, it was shown that MT1-MMP activity was increased during ischemia and reperfusion in the ischemic myocardium, but that no change in MT1-MMP activity occurs in the remote myocardium. This demonstrates the selectivity and specificity of this system in measuring MMP activity in vivo.

The dialysate upon which the fluorescence was being read was collected over a 30 minute period. In order to measure changes in real-time, a new technique was developed. Instead of collecting the returned dialysate for 30 minutes at a time, the fluorescence was read in real time by connecting the outlet tubing of the probe through the inlet port of the FIAlab PMT-FL and into the 10 mL cuvette.

The FIAlab PMT-FL Detector (FIAlab Instruments, Inc., Bellevue, Wash.) is a flow-through fluorescence detector. It utilizes a photon counting photomultiplier tube (PMT) that is exceptionally sensitive to low emission. The UV light source used was the Model D-1000CE Standard Fiber Optic UV Source. Its wavelength range is 190-410 nm. (Analytical Instruments Systems, Inc., Flemington, N.J.). Connecting the UV light source to the flow-through fluorescence detector is a 600 mm SMA fiber optic cable (Oceanoptics, Inc, Dunedin, Fla.). Inside the PMT-FL, the UV light passes through the excitation filter (280 nm), exciting the extracellular fluid (with cleaved substrate included) within the 10 mL cuvette, and photons are transmitted to the PMT. In the PMT, the photons were multiplied and transferred to a computer. A modem cable with DB9 female to DB25 male connected the PMT-FL to the laptop computer. The software analysis package (FIAlab ver. 5) then allowed for real-time detection of changes in fluorescence.

Figure 26:
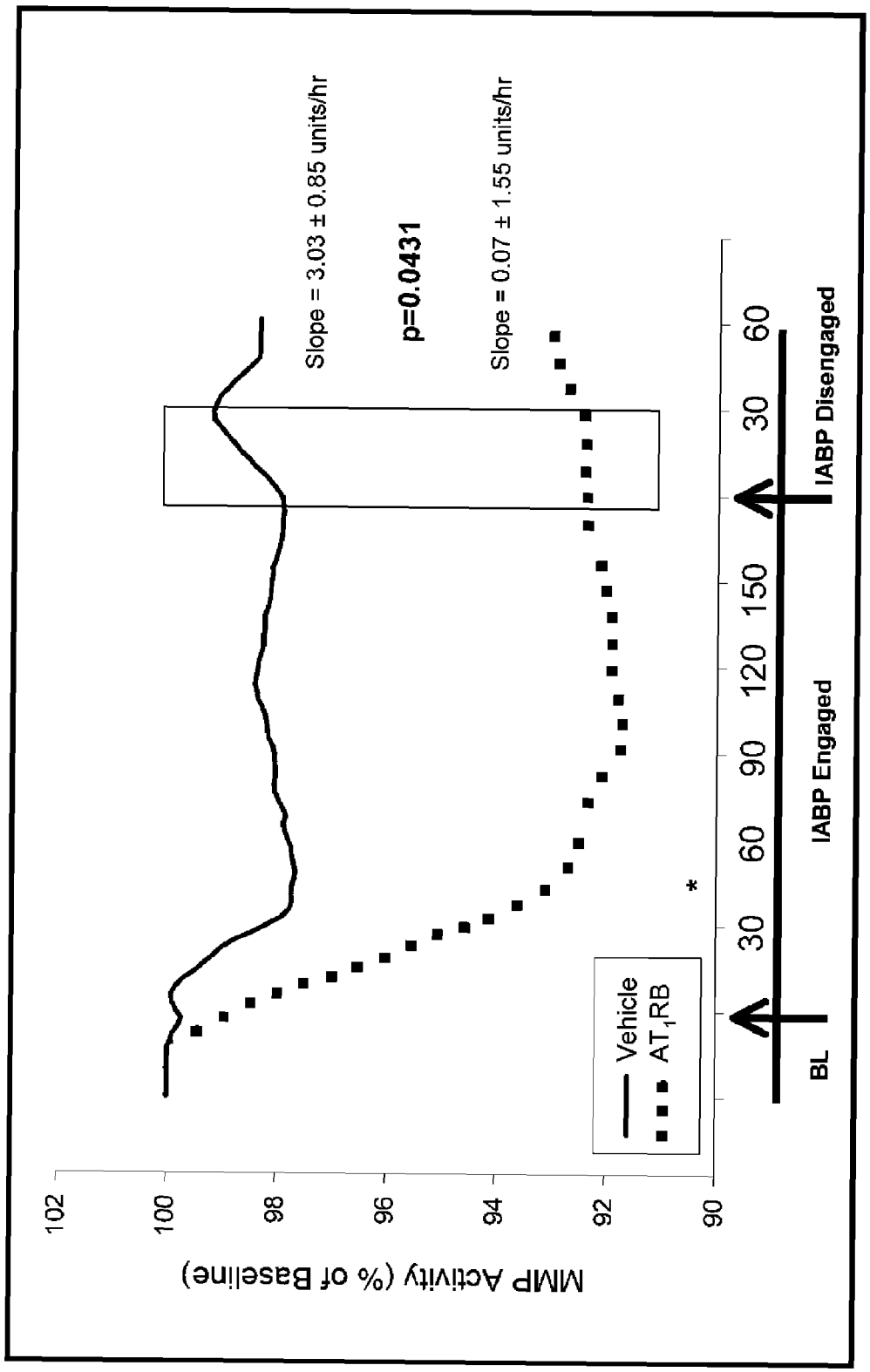
FIG. 26 is a graphical illustration showing reduction of MMP activity during acute pressure overload and a surge in MMP activity when the increased overload is removed.

With this system, measurement of MMP activity in the setting of acute pressure overload was accomplished. The data demonstrated that MMP activity is reduced during acute pressure overload and there is a surge in MMP activity when the increased overload is removed. (FIG. 26). In addition, it was demonstrated that the angiotensin type 1 receptor might be responsible for a reduction in this surge.

Exemplary materials and methods for use with the systems and methods include those detailed below.

Myocardial Interstitial MMPs: For the determination of myocardial interstitial MMPs, Yorkshire pigs (n~17, 35 to 40 kg, Hambone Farms, Orangeburg, S.C.) can be used.

Instrumentation: Pigs were sedated with diazepam (200 mg po) and general anesthesia was induced using inhaled isoflurane (2%), sufentanyl (2 ~g/kg IV), etomidate (0.3 mg/kg IV), and vecuronium (10 mg IV) through an ear vein. The animal was then placed on the operating table, an open tracheostomy was performed, and mechanical ventilation was initiated to maintain arterial CO2 between 35 to 45 mm Hg and pH 7.35 to 7.45. The right common carotid artery was accessed to transduce arterial blood pressure, and the right internal jugular vein was cannulated for maintenance of anesthesia and fluids (0.9% normal saline, 10 cc/kg/h). A balloon-tipped multi lumen thermodilution catheter (7.5 F, Baxter Healthcare Corp) was placed in the pulmonary artery via the left external jugular vein. The bladder was instrumented with a catheter for monitoring of urine output.

Before entering the chest, animals were premedicated with lidocaine (100 mg IV followed by 10 mg/h infusion), bretyllium (250 mg IV), and magnesium sulfate (2 g IV). Median sternotomy was performed and a precalibrated microtipped pressure transducer (7.5 F, Millar Instruments Inc) was placed through the apex of the LV through a stab incision and sutured into place. Next, 4 sonomicrometry crystals (2 mm, Sonometrics, Ontario) were placed at the endocardial surface of the apex, the LV mid-posterior wall, the anterior wall between the first and second diagonal branches of the left anterior descending artery, and on the epicardial surface of the anterior wall directly overlying the endocardial crystal in that location. A pacemaker lead was sutured to the left atrium, and the animals were atrially paced throughout the procedure at a target rate of 125 bpm. Through a purse-string suture in the ascending aorta or through the left internal iliac artery, an intra-aortic balloon catheter (IABP, Datascope, Montvale, N.J.) was positioned in the descending thoracic aorta a minimum of 4 centimeters from the diaphragmatic division of the aorta. This approach did not affect hemodynamics or cardiac output. The animal was given heparin (150 U/kg IV) before placement of the balloon pump. Finally, 2 microdialysis catheters were inserted into the mid-myocardium of the anterior wall of the LV through a break-away sheath and connected to a custom-made system to measure real-time MMP activity.

Microdialysis: Microdialysis probes with a molecular weight cutoff of 20 kDa and an outer diameter of 0.5 mm were placed in the LV. The molecular weight cutoff of the microdialysis probe prevented any MMP species from traversing the membrane. A fluorogenic substrate specific for MMP-1, 2, 3, 7, and 9 (Calbiochem, La Jolla, Calif.) at a concentration of 60 ~mol/L was stored in a 2.5 mL Bee Stinger® Gastight Syringe (Bioanalytical Systems, Inc) and infused at a rate of 5 ~L/min through the 2 probes by the Baby Bee® Syringe Drive controlled by the MD-1020 Bee Hive Controller (Bioanalytical Systems, Inc). Fluorescence emitted via substrate cleavage deter-mined MMP activity. Substrate was allowed to equilibrate for 20 minutes before the beginning of the protocol. All tubing and syringes were protected from light. The specificity of this substrate was determined and performed as described for these fluorogenic substrates previously. Specifically, this substrate was incubated with MMP-2/9 recombinant protein (500 ng/mL, Chemicon) and demonstrated steady-state fluorescence emission by 60 minutes. With the addition of a broad spectrum MMP inhibitor (BB-94, 10 mmol/L, British Biotech), fluorescence emission was abolished.

Real-time Activity: One of the 2 probes was used to determine real-time MMP activity during the protocol. The dialysate that returned through the probe was connected to a FIAlab PMT-FL Detector (FIAlab Instruments, Inc). The dialysate traveled into the fluorescence detector where an UV light (Model D-1000CE, Analytical Instruments Systems, Inc, Flemington, N.J.) and a 280 nm excitation filter excited the sample. The light then passed through a 360 nm 10 nm bandpass emission filter into the photomultiplier tube. The fluorescence detector was connected to a laptop computer and software (FIAlab ver. 5) allowed for the real-time detection of changes in fluorescence.

Cumulative Activity: The remaining probe was used to validate this novel real-time activity detection system. Dialysate returning from this probe was collected into amber microcentrifuge tubes at 30-minute intervals throughout the protocol. After each interval, the tube was stored on ice. On completion, 100 ~L of each dialysate sample was added to a 96-well polystyrene plate (Nalge Nunc International) and read at an excitation wavelength of 280 nm and an emission wavelength of 360 nm on the FLUOstar® Galaxy fluorescent microplate reader (BMG Labtechnologies, Durham, N.C.).

Protocol: After instrumentation was completed and the microdialysis catheters were equilibrated, a 30-minute baseline period was begun. At the end of the baseline time point, a full hemodynamic profile was obtained, including measurement of LV and aortic pressures, pulmonary pressures, pulmonary capillary wedge pressure (PCWP), cardiac output (in triplicate), and urine output. In addition, blood was collected for measurement of plasma renin activity (PRA) as described previously. In a subset of animals, LV myocardial biopsies were taken at baseline, after the 180 minutes of IABP engagement, and at the end of the protocol. MMP fluorogenic substrate was collected from both microdialysis catheters. Pressure waveforms and sonomicrometric crystal signals were digitized on computer for subsequent analysis at a sampling frequency of 100 Hz (Sonolab, Sonometrics).

After baseline measurements, pigs were randomized to an angio-tensin receptor blocker (AT1RB, Valsartan) or vehicle (normal saline). The AT1RB was given as a bolus of 1 mg/kg over 1 to 2 minutes, followed by an infusion of 3 ng/kg/h, which was continued throughout the protocol. This dose was previously found to have no effect on mean arterial pressure, yet still inhibited the angiotensin pressor response.

After randomization, the intra-aortic balloon pump was activated and augmented so that the balloon inflated during systole and deflated during diastole, creating a noticeable increase in LV peak pressure as seen on the pressure waveform. Hemodynamic and sonomicrometry crystal tracings were digitally recorded at 30-minute intervals for 180 minutes along with blood and microdialysis effluent collection. The balloon pump was then disengaged, and recordings were performed for an additional 60 minutes.

In Vivo/In Vitro Validation Studies: In order to further examine the relationship between real-time MMP activity and other biochemical assays, zymographic studies as well as in vitro MMP activity assays were used.

Gelatin Zymography: LV myocardial extracts (10 g protein) were subjected to electrophoresis followed by gelatin (Novex 10% zymogram gel, 0.1% gelatin, Invitrogen) zymography. The size-fractionated MMP proteolytic regions were quantified by densitometry (Gel Pro Analyzer, Media Cybernetics).

In Vitro MMP Activity: In a subset of animals, tissue was collected at the termination of the protocol, was homogenized, and was subjected to in vitro MMP activity detection using the same MMP-1, 2, 3, 7, and 9 fluorogenic substrate used in the in vivo real-time assay. Twenty micrograms of protein were loaded into a 96-well polystyrene plate (Nalge Nunc International, Rochester, N.Y.) and were injected with 60 ~mol/L of MMP fluorogenic substrate. The reaction was allowed to proceed for 30 minutes at 37° C. and fluorescence units were read on the FLUOstar® Galaxy fluorescent microplate reader (280 and 360 nm, excitation and emission; BMG Labtechnologies). MMP-2/9 standards (1000 to 31.25 ~g/mL); pretreated with APMA) were also incubated with the substrate to generate a standard curve.

Data Analysis: Hemodynamics and cardiac output were compared at each time point, and digitized sonomicrometric signals were analyzed to measure the distance between each crystal at end-systole and end-diastole and averaged more than 4 consecutive beats. These measurements were used to determine LV end-systolic and end-diastolic dimension and wall thickness, segmental shortening, and wall thickening. Peak circumferential wall stress was calculated as previously described using hemodynamic and sonomicrometry data. Statistical analysis was performed using unpaired t-tests comparing each time point to baseline values and corrected for number of comparisons. Pair-wise comparisons were made between treatment groups at specific time points using paired t-tests. In addition, the 95% limit of agreement was determined using the Bland and Altman method for assessing agreement between 2 methods of clinical measurement. All statistical analysis was done using the STATA statistical software package (Statacorp). Values of P~0.05 were considered to be statistically significant.

Cardiopulmonary Bypass. Patients: Twenty patients undergoing elective coronary artery bypass surgery requiring CPB were studied. Initial cardioplegia was accomplished with antegrade administration of 200 to 250 mL of normothermic cardioplegic solution containing 4 parts blood to 1 part D5W 0.2 NaCl containing 29 mL of tromethamine buffer, 34 mL of adenosine citrate phosphate dextrose, and 30 mEq/L of KCL. This was followed immediately by retrograde administration of 1000 mL of hypothermic (5° C.) 4:1 blood:crystalloid cardioplegic solution. At 20-minute intervals cardioplegia was maintained with retrograde administration of 200 to 500 mL of the cardioplegic solution with a lower KCl concentration (15 mEq/L). Before removal of the crossclamp, a 500- to 750-mL dose of terminal normothermic cardioplegic solution was given. At the termination of CPB, heparin was neutralized with protamine in a 1:1 ratio.

A probe containing a 4 mm long membrane was used (20 kDa; outer diameter of probe shaft, 0.77 mm; outer diameter of probe membrane, 0.5 mm; CMA/Microdialysis, North Chelmsford, Mass.). The probe was placed into the LV apical midmyocardium and prepared for dialysate collection. A radial artery was catheterized and used to obtain systemic samples. Systemic and myocardial interstitial samples were collected at baseline and up to 30 minutes post-CPB.

ET Analytical Measurements: Plasma and dialysate samples were first eluted over a cation exchange column (C-18 Sep-Pak; Waters Associates, Milford, Mass.) and then dried by vacuum centrifugation. The samples were reconstituted in 0.02 mol/L borate buffer, and a high-sensitivity radioimmunoassay was performed (RPA 545, Amersham, Arlington Heights, Ill.). After incubation of samples with 125I-labeled ET and ET specific antibody, a charged secondary antibody was added. Bound and free labels were magnetically separated. Two sets of standards were constructed to support the range of ET within the 2 sample sets: 0.003 to 1.0 fmol/mL for the interstitial samples and 2.0 to 32.0 fmol/mL for the plasma samples. Although past studies have reported ET levels in picograms per milliliter, the present study as well as more recent reports have used a high-sensitivity assay that allows for ET measurements to be reported within the fentomolar range. A standard curve used for the plasma and microdialysis samples, which demonstrated the high sensitivity and operating range of this assay system. The interassay variation was 7% and 2% for the plasma and microdialysis ET measurements, respectively. The plasma ET concentrations were corrected for potential hemodilution artifact by using changes in hematocrit.

Microdialysis Calibration: The first set of calibration experiments determined the relative recovery of ET in the microdialysis system using a 125I-ET tracer. The relative recovery of ET at a flow rate of 2.5 ~L/min was calculated to be 15%~1%, and this value was used as the correction factor for recovery of myocardial interstitial samples. A second set of validation experiments were performed in vivo in an anesthetized pig preparation described previously. Adult pigs (n~3, 25 kg, Hambone Farms, Orangeburg, S.C.) were anesthetized with isoflurane (3%), microdialysis probes placed, and ET microdialysis measurements performed for up to 6 hours. ET values at 1- and 6-hour time points were 24~7 and 25~8 fmol./mL, respectively (P~0.82). Thus, this microdialysis technique yielded reproducible interstitial ET values over time. To confirm that probe placement did not impede diffusion as well as reached a steady state within the interstitial compartment, a 125I-ET solution (20 fmol/mL, 2.5 uL/min, Amersham) was infused and dialysate radioactivity determined. At the end of the 125I-ET infusion period, the dialysate was immediately changed (using a servo-control system, CMA) to buffer and collection continued. 125I-ET reached steady-state levels by approximately 30 minutes. These results indicated a balance between the rate of 125I-ET infusion and the return of radiolabeled ET in the dialysate. With termination of the 125I-ET infusion, the dialysate concentration of radiolabeled ET fell in a time-dependent manner. After these experiments, the tissue was harvested and sections taken at 2-mm intervals from the probe tip. All the radioactive ET-1 remained compartmentalized within a 4-mm radius around the probe, as no 125I-ET was detected in samples taken from greater distances. Thus, the radiolabeled ET remained within the interstitial space surrounding the microdialysis probe and could be modeled as a closed compartment system.

Data Analysis: Plasma and interstitial ET levels at each time point were evaluated with a 2-way analysis of variance (ANOVA). If the ANOVA revealed significant differences, individual group means were compared by pairwise adjusted Bonferroni probabilities. All statistical procedures were performed with the BMDP statistical software package (BMDP Statistical Software Inc, Los Angeles, Calif.). Patient characteristics and perioperative data are presented as mean ~SD. For categorical data such as graft number and incidence of pharmacologic support, a chi-square analysis was performed. All analytical parameters are presented as mean ~SEM.

Myocardial Infarction: Mature pigs (n 5 20, Yorkshire, 35-40 kg, Hambone Farms) were instrumented to obtain indexes of LV global and regional function as well as for the measurement of myocardial interstitial MMPs. Anesthesia was initially induced with intravenous administration of 50 mg etomidate (Amidate, Elkins-Sinn), and an endotracheal tube was placed. A loading dose of 50 mg sufentanil (Elkins-Sinn) was then administered, and a maintenance infusion of lactated Ringer solution (400 ml/h) and morphine 60 mg/h, Elkins-Sinn) was initiated. A continuous infusion of tubocurarine (3 mg/h, Bristol-Myers-Squibb) and lidocaine (120 mg/h, Elkins-Sinn) was established. In preliminary studies, this anesthetic protocol provided a deep anesthetic plane and stable hemodynamic profiles for at least 8 hours.

After a surgical plane of anesthesia was established, an arterial line (7-Fr) was placed in the right carotid artery, and a multilumened thermodilution catheter (7.5-Fr, Baxter Healthcare; Irvine, Calif.) was positioned in the pulmonary artery from the right external jugular vein. The fluid-filled aortic and pulmonary artery catheters were connected to externally calibrated transducers (Statham P231D, Gould; Oxnard, Calif.). A sternotomy was performed, and a vascular ligature was placed around the inferior vena cava to perform transient caval occlusion. A precalibrated microtipped transducer (7.5-Fr, Millar Instruments; Houston, Tex.) was placed in the LV through the apex and sutured in place. Two pairs of piezoelectric crystals (2 mm, Sonometrics; Ontario, Canada) were positioned within the midmyocardium to measure segmental wall motion. The first crystal pair was placed between the first and second diagonal branches of the left anterior descending artery. The second crystal pair was placed between the first (OM1) and second obtuse marginal (OM2) branches of the circumflex coronary artery. The pressure waveforms and crystal signals were digitized on a computer for subsequent analysis at a sampling frequency of 250 Hz (Pentium Processor, Dell; Round Rock, Tex.). A microdialysis probe was inserted in the midmyocardial region between each pair of crystals, sutured in place, and prepared as described in Myocardial interstitial MMP measurements by microdialysis. Snare occluders were then loosely placed around the OM1 and OM2 branches. After instrumentation and a 60-min equilibration period, baseline measurements were recorded. These measurements included heart rate, cardiac output, stroke volume, aortic pressure, LV end-systolic and -diastolic pressure, peak rate of pressure development (1 dP/dt), and LV regional segmental shortening. To more carefully determine regional myocardial performance, LV end-diastolic pressure and segmental shortening values obtained during caval occlusion and re-lease were subjected to regression analysis. From the regression analysis, the slope of the regional preload re-cruitable stroke-work (PRSW) relationship was computed.

After the microdialysis systems were equilibrated, baseline interstitial fluid was collected, and baseline hemodynamics were obtained, regional ischemia was induced through closure of the OM1 and OM2 ligatures. This region of the LV was chosen for ischemic injury because it does not provide blood supply to a major myocardial conduction pathway and, therefore, did not result in atrioventricular block or refractory arrhythmogenesis. LV function and microdialysis samples were collected for up to 3 hours after coronary ligation. A 3-h total ischemic period was chosen because it has been previously demonstrated to result in permanent myocyte injury and infarction. In the present study, blood samples were collected at baseline and at each hour after occlusion to measure troponin-I levels, a specific marker of myocyte injury and infarction. In preliminary studies, selective coronary ligation of the OM1 and OM2 branches for 3 h resulted in an infarct size of 25 6 3% based on the triphenyltetrazolium chloride staining technique. Moreover, core temperature was rigidly maintained at 37° C. during the entire 3-h occlusion period because small fluctuations in temperature have been previously demonstrated to influence infarct size in swine. None of the animals used in this study required electrical cardioversion after coronary occlusion. At the conclusion of the 3-h study period, the LV was quickly harvested and placed in ice-cold Krebs solution. The LV free wall was dissected into the ischemic region, the border region, and the remote region. The border region was defined as a 0.5-cm perimeter surrounding the infarcted region. The myocardial samples were then flash-frozen in liquid nitrogen for subsequent zymographic analysis.

Myocardial interstitial MMP measurements by microdialysis: The microdialysis system used in the present study was adapted from previously described techniques to measure bioactive peptides. In the first set of experiments, the microdialysis probe contained a 4-mm-long membrane with a 100-kDa molecular mass cutoff (CMA12, CMA/Microdialysis; North Chelmsford, Mass.). The pore size of the dialysis membrane allowed for traversal of MMPs, which are predominantly below this molecular weight cutoff. A Krebs buffer solution containing 0.5% BSA was perfused through the probe using a computer-controlled syringe pump at 2.5 ml/min (Baby Bee and Beehive Controller, CMA/Microdialysis). After a 60-min infusion period in which the interstitial fluid equilibrated with the dialysate, the dialysate was collected into chilled microtubes and flash-frozen. The long-term placement of the microdialysis probes within the mid-myocardium produced no effect on LV regional function, as assessed by sonomicrometry. A previously per-formed post-mortem study of myocardial sections containing the probe showed no extravasations of blood cells or inflammatory response after long-term placement (0.3 h). A flow rate of 2.5 ml/min was chosen for this system based on initial measurements using an in vitro calibration system. For this in vitro approach, the microdialysis probe was immersed in a Krebs solution containing purified gelatinase (MMP-2 and MMP-9, 1.25 mg/m, Chemicon International; Temecula, Calif.), and dialysate was collected every 60 min using a flow rate of 1-5 ml/min. The immersion solution and the dialysate were subjected to zymographic analysis as described in MMP zymography and presented in detail previously. For the microdialysates collected in vivo, these samples were stored at 270° C. until the time of zymo-graphic analysis.

In a second set of studies, interstitial myocardial MMP activity was directly quantified using a MMP fluorogenic substrate. For these studies, microdialysis probes containing a 20-kDa molecular mass cutoff (CMA/20, CMA/Microdialysis) membrane were placed within the mid-myocardium. This molecular mass cutoff effectively excluded MMP species from directly traversing from the interstitial space into the microdialysis membrane. Instead, the micro-dialysis infusate contained a quenched fluorogenic substrate (50 mM DNP-Pro-Leu-Gly-Leu-Gly-Met-Trp-Ser-Arg-OH; Calbiochem) specific for the gelatinases MMP-2 and MMP-9. Initial in vitro studies were performed in which the concentration of the MMP substrate contained within the microdialysate was varied (10-200 mM) and infused at 2.5 ml/min in an immersion solution containing purified MMP-2/9 (50 mM, 37° C.). The entire microdialysis system was protected from ambient light, and the dialysate was collected at 10-min intervals into chilled amber tubes and immediately processed for fluorimetry measurements. The samples were read using excitation and emission wavelengths of 280 and 360 nm, respectively (Gilford Fluoro IV; Oberlin, Ohio). A time-dependent increase in relative fluorescence was observed, which plateaued by 60 min of infusion. This MMP substrate did not autofluoresce, and no fluorescence could be detected in the absence of MMP in the immersion solution. For the in vivo studies, the MMP substrate was infused for 60 min to reach equilibrium, and baseline interstitial MMP fluorescent proteolytic activity was deter-mined. The interstitial fluorescent measurements were converted to nanograms per microliter of MMP-2/9 activity based on the in vitro calibration curves. In preliminary studies, coinfusion of the MMP substrate and a broad spectrum MMP inhibitor (5 mM galardin, British Biotech) abolished all fluorescent activity in the interstitial microdialysate samples. To compare the relative changes in MMP interstitial activity after coronary occlusion, the time-dependent change in fluorescent activity from baseline values was computed for the ischemic and remote regions.

MMP Zymography: LV MMP gelatinase activity and abundance were examined by substrate-specific zymography. The LV myocardial extracts (5 mg total protein) were subjected to electrophoresis followed by zymography. The microdialysate (5 ml) was suspended in 5 ml of electrophoresis buffer (10% SDS, 4% sucrose, 0.25 M TriszHCl, and 0.1% bromophenol blue; pH 6.8) and subjected to zymographic analysis. To provide an internal control with respect to the zymographic activity, cell culture media samples from a cultured human fibrosarcoma HT 1080 cell line were included. The zymograms were digitized, and the size-fractionated banding pattern, which indicated MMP proteolytic activity, was determined by quantitated image analysis (Gel Pro Analyzer, Media Cybernetics; Silver Spring, Md.). The lysis areas were measured by two-dimensional inte-grated optical density computations and expressed in pixels.

Data Analysis: Changes in LV regional function, hemodynamics, and MMP levels after the induction of an MI were initially compared with baseline values by ANOVA. This approach was based on using a two-way ANOVA for repeated measures. The main treatment effects were myocardial region (MI and remote regions) and time post-MI. Specific comparisons between baseline and post-MI values were per-formed by a Bonferroni adjusted t-test. Cumulative changes in fluorescent activity obtained in the MMP substrate studies were subjected to a two-way ANOVA for repeated measures. Statistical analysis was performed using statistical software programs (BMDP Statistical Software, University of California Press; Los Angeles, Calif.).

Coronary revascularization: This method and system were used in the human subjects undergoing coronary revascularization with cardiopulmonary bypass (CPB).

Example 5

Identification of Fluorogenic Substrates

The described fluorogenic microdialysis system has been used with proteolytic substrates such as those for MMPs, an in particular membrane bound MMPs, which would not otherwise be possible to measure. However, new insights gained from MT1-MMP degradomics, show that differential substrate processing by MT1-MMP occurs.

One such processing pathway is that of transforming growth factor (TGF), which is implicated in cancer, cardiovascular disease and inflammation to cause organ failure secondary to fibrosis. TGF signaling causes stimulation of collagen synthetic pathways which would favor matrix accumulation. TGF is synthesized as an inactive precursor comprised of mature TGF growth factor and its amino-terminal prodomain (also called the latency associated peptide; LAP). This inactive precursor is bound to a latency-associated TGF binding protein (LTBP) through disulfide bonds that form between the LAP and a cysteine rich motif found within LTBP. The most commonly studied type of LTBP, is LTBP-1. This large latent complex functions to target TGF to the ECM. Full activation and release of TGF into the interstitium requires specific proteolysis of LTBP-1. Accordingly, a specific cleavage site for MT1-MMP was identified within LTBP-1, which in yields the appropriate LTBP-1 fragments causing TGF release.

The first step was to obtain the full length sequence for LTBP-1 (NCBI; AA130290.1) and to then perform initial sequence recognition for MT1-MMP proteolytic regions. This was further enhanced by MT1-MMP substrate binding/cleavage sites identified by Kridel and coworkers. In this past study, unique substrate binding sties were identified for MT1-MMP, which were not recognized or proteolytically processed by other MMP types, such as MMP-9. Utilizing these published results, a series of peptide mimics were assessed for there ability to be cleaved by MT1-MMP and ranked for specificity. Three peptides were selected from these reported results based on the highest catalytic efficiency ratio for MT1-MMP. These catalytic ratios were based upon the specificity of MT1-MMP to recognize and cleave this sequence as opposed to other MMPs with similar recognition domains (ie MMP-9). The peptides were: A176: SGRSENIRTA, A42: SGRIGFLRTA, and B175A: SGAAMHMYTA. These potential peptides were then utilized in our laboratory for further in-silico mapping and alignments. The peptides were aligned to each individual sequence of interest to identify potential binding/cleavage sites using the CLUSTAL W+alignment algorithm with the BLOSSUM scoring matrix.

Figure 27:
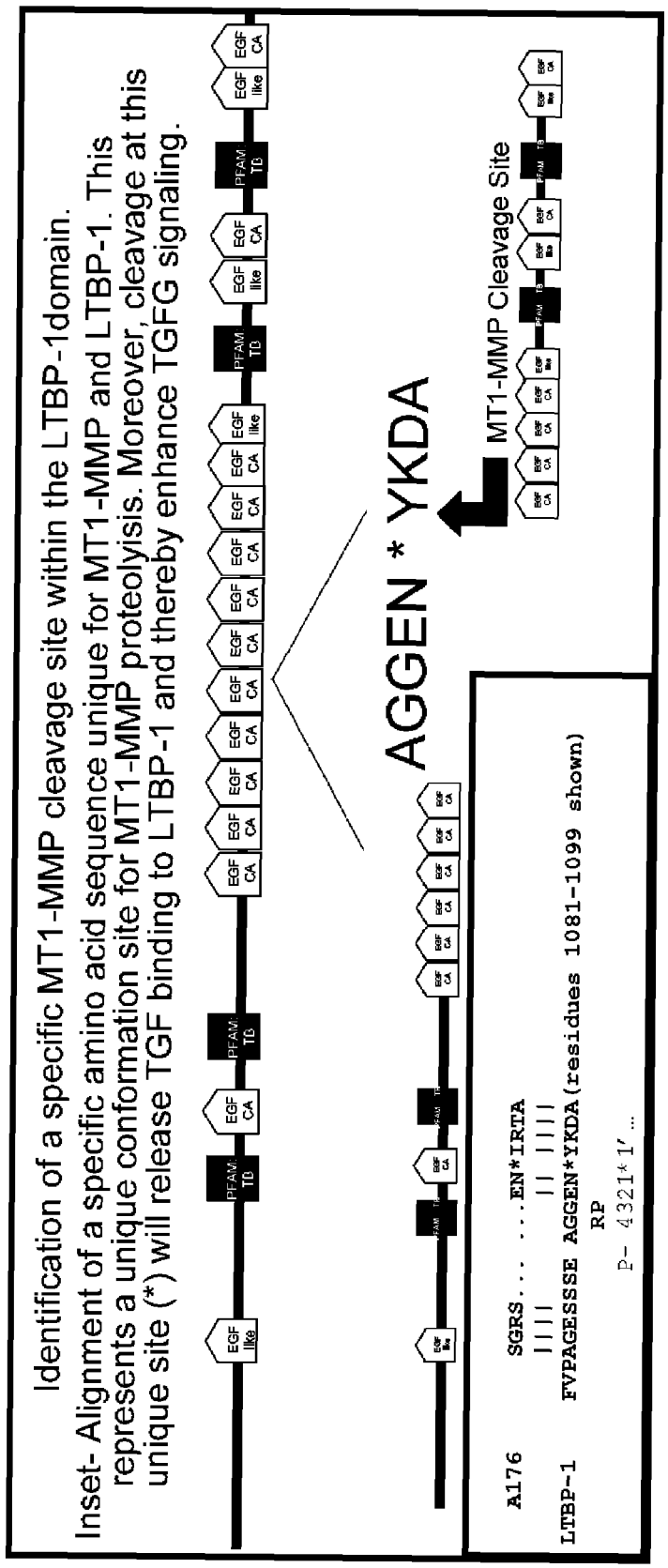
FIG. 27 illustrates identification of a specific MT1-MMP cleavage site within the LTBP-1 domain. The inset shows alignment of a specific amino acid sequence unique for MT-MMP and LTBP-1. This represents a unique conformation site for MT1-MMP proteolysis. Moreover, cleavage at this site (*) released TGF binding to LTBP-1 and thereby enhances TGF signaling.

Proteins demonstrating positive peptide alignment were analyzed for domain structure using the Simple Modular Architecture Research Tool (SMART) to assess the significance of the putative cleavage site. All three peptides failed to align significantly with other similar proteins such as the BNP-precursor, ET-1 precursor, and LAP proteins. Similarly, peptides A42 and B175A also failed to align with LTBP-1. Conversely, peptide A176 demonstrated significant concordance with LTBP-1 and the amino acid residue concordance is shown in FIG. 27. The sequence alignment generated a high concordance match to the A176 peptide. Importantly, there is significant alignment of the last 6 residues which defines the region where MT1-MMP catalytic activity would occur (the site of cleavage depicted as a star). Of particular interest is the lysine residue (K) preceded by a hydrophobic residue (Y), which in turn is preceded by two identical residue matches. The lysine/arginine at position 1098 is used for MT1-MMP specific cleavage and identifies that a unique proteolytic site, specific for MT1-MMP exists within the LTBP-1 structure. More importantly, this cleavage site results in the disruption of TGF binding, and thereby releases TGF into the interstitium for interaction with the TGF receptors. This MT1-MMP cleavage site for LTBP-1 falls within a Ca2+-binding EGF-like protein:protein interaction domain of LTBP-1 (residues 1076-1117).

Figure 28:
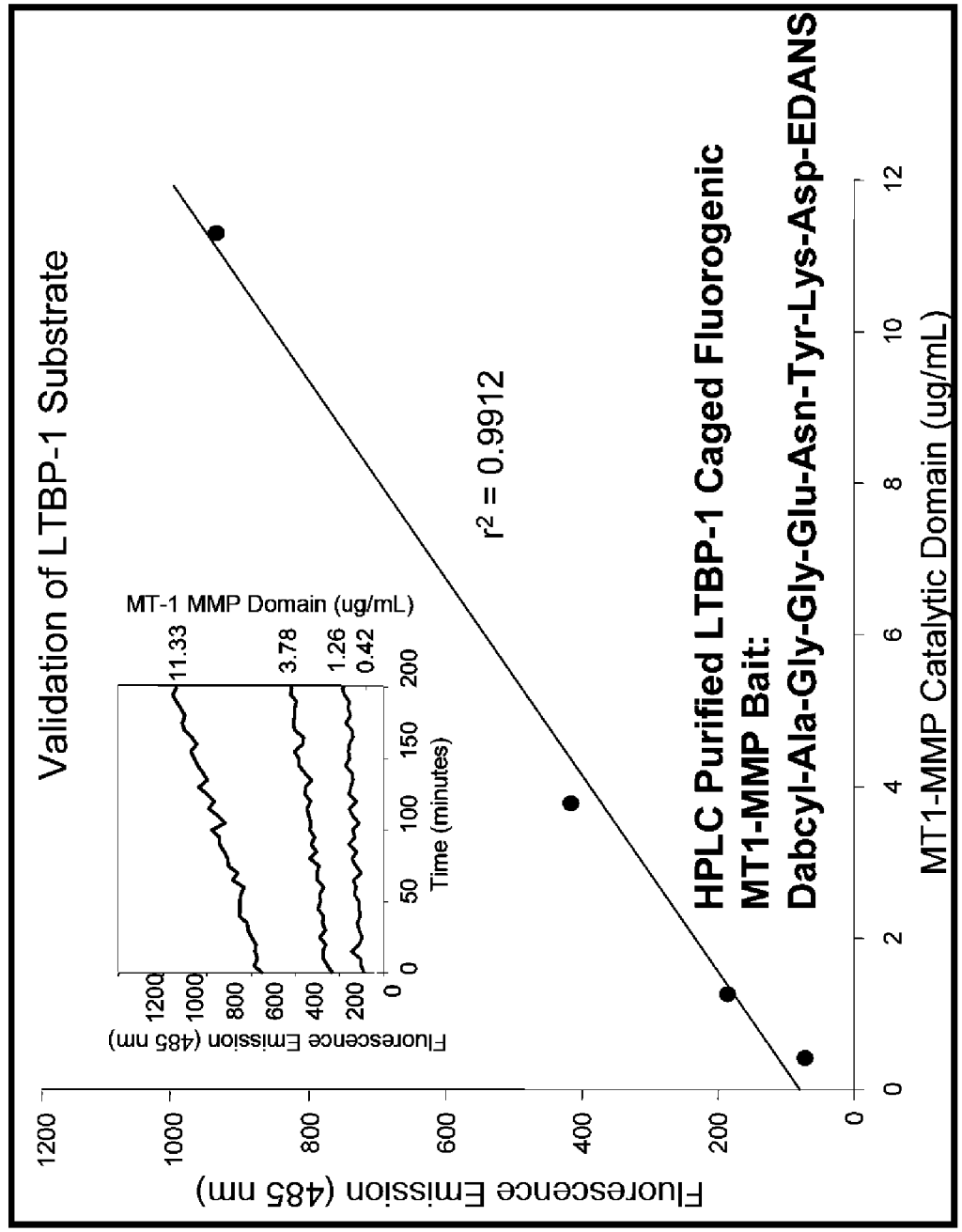
FIG. 28 graphically illustrates validation of an LTBP-1 substrate.

Previous studies have identified mutations within a similar type of domain in fibrillin-1, an LTBP-1 homologue, implicated in Marfan Syndrome (MFS). Furthermore, MFS has been associated with the over-stimulation of TGF-Beta signaling as a result of fibrillin-1 mutation. Using this unique sequence, a fluorogenic peptide was constructed and validated. This peptide sequence was synthesized in a caged fluorogenic construct (AnaSpec Inc, CA; newly assigned peptide name:SCJJ-1) with a certified HPLC purity of >98% FIG. 28. Using the incubation conditions and fluorescent equipment described in the previous section, and a specific excitation/emission wavelength (340/483 nm), 15 uM of LTBP-1 was exposed to increasing concentrations of the MT1-MMP catalytic domain FIG. 28.

A clear fluorescent signal was detected with increasing concentrations of MT1-MMP which was highly linear. Co-incubation with the MT1-MMP selective inhibitor (0007258; 5 pM), the global MMP inhibitor (BB94, 1 uM) or MT1-MMP blocking antibody (1 mg/mL, AB8102) extinguished all fluorescent activity. Incubation with an MMP-2/-9 catalytic domain cocktail (10 ug/mL) caused no fluorescent emission from the LTBP-1 substrate. Thus, an LTBP-1 peptide sequence constructed and validated that is specifically cleaved by MT1-MMP.

Various publications were referenced in preparation of this application. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of real-time in vivo monitoring of a biological process, comprising:
   identifying a compound of interest that is located in the non-cardiac interstitium of the subject, wherein the activity or presence of the compound is related to the in vivo biological process being monitored;
   positioning a probe within the non-cardiac interstitium of the subject;
   infusing the interstitium of the subject with a fluorogenic substrate specific for the compound of interest wherein the substrate is infused therethrough the probe;
   receiving interstitial fluid from the subject with the probe, wherein the interstitial fluid comprises the substrate; and
   detecting the received substrate to monitor the biological process in the subject.

2. The method of claim 1, wherein the biological process monitored is death or injury of a cell.

3. The method of claim 1, wherein the non-cardiac interstitium is located in the joint of a subject.

4. The method of claim 1, wherein the biological process is cancer, the method further comprising, prior to positioning the probe within the interstitium of the subject, administering cancer therapy to the subject having cancer wherein the administered therapy causes death or injury of a tumor cell and the subsequent release of identified compound from the dead or injured cell.

5. The method of claim 1 further comprising, prior to positioning the probe within the interstitium of the subject, administering a pharmaceutical agent to the subject wherein the pharmaceutical agent modifies the biological process therein the subject, wherein the fluorogenic substrate is configured to be altered to a detectable state by the biological process, wherein the detectable state of the fluorogenic substrate indicates the modification of the biological process by the administered agent, wherein the modification is used to monitor the therapeutic regimen in subject.

6. The method of claim 5, wherein an increase in detected fluorogenic substrate indicates the modification of the biological process by the administered agent.

7. The method of claim 5, wherein a decrease in detected fluorogenic substrate indicated the modification of the biological process by the administered agent.

8. The method of claim 7, wherein the pharmaceutical agent acts to inhibit the biological process.

9. The method of claim 8, wherein the pharmaceutical agent is Aprotinin.

10. The method of claim 1 further comprising, prior to positioning the probe within the interstitium of the subject,
    administering a pharmacological agent to the subject to effect a modification of the biological process therein the subject, wherein at least a portion of the fluorogenic substrate is altered in the interstitium of the subject, wherein the received substrate is the altered fluorogenic substrate, and
    determining the modification of the biological process which is indicative of the pharmacological activity of the administered pharmacological agent via detection of the received substrate.

11. The method of claim 1 further comprising, prior to positioning the probe within the interstitium of the subject, administering a pharmaceutical agent to the subject to effect a modification of the biological process therein the subject, wherein at least a portion of the fluorogenic substrate is altered in the interstitium of the subject, wherein the received substrate is the altered fluorogenic substrate, wherein detecting the modification in the biological process is monitored via detecting the received substrate.

12. The method of claim 11, wherein an increase in detected altered fluorogenic substrate indicates the modification of the biological process by the administered agent.

13. The method of claim 11, wherein a decrease in detected altered fluorogenic substrate indicated the modification of the biological process by the administered agent.

14. The method of claim 13, wherein the pharmaceutical agent acts to inhibit the biological process and to thereby decrease the amount of detectable altered fluorogenic substrate.

15. The method of claim 14, wherein the pharmaceutical agent is Aprotinin.

16. The method of claim 11, wherein the detectable state of the fluorogenic substrate is detected in real-time to indicate the modification of the biological process by the administered agent in real-time.

17. The method of claim 1 further comprising, prior to positioning the probe within the interstitium of the subject, administering Aprotinin to the subject, wherein at least a portion of the fluorogenic substrate is altered in the interstitium of the subject, wherein the received substrate is the altered fluorogenic substrate, wherein detecting the received substrate is accomplished by detecting or measuring energy emitted by the altered fluorogenic substrate, the presence or amount of said energy indicating Aprotinin activity in the subject.

18. The method of claim 17, wherein the detected or measured energy is monitored over time and wherein a decrease in the detected or measured energy emitted indicates increased Aprotinin activity in the subject.

19. The method of claim 17, wherein the detected or measured energy is monitored over time and wherein an increase in the detected or measured energy emitted indicates decreased Aprotinin activity in the subject.

20. The method of claim 17, wherein the fluorogenic substrate comprises a polypeptide comprising the sequence Ala-Leu-Lys-V', wherein V' is a fluorophore.

21. The method of claim 20, wherein the fluorophore emits energy upon cleavage of the bond between the Lys residue and the fluorophore by a serine protease.

22. The method of claim 21, wherein the serine protease is plasmin.

23. The method of claim 17, wherein the fluorophore is 7-amido-4- (trifluoromethyl)coumarin.

24. The method of claim 1, wherein the biological process monitored is cardiovascular disease.

25. The method of claim 24, wherein the cardiovascular disease is ischemia reperfusion (I/R).

26. The method of claim 24, wherein the cardiovascular disease is hypertrophy.

27. The method of claim 24, wherein the cardiovascular disease is heart failure.

28. The method of claim 1, wherein the biological process is monitored during a therapeutic protocol.

29. The method of claim 1, wherein the biological process is monitored during drug infusion.

* * * * *